US008053463B2

(12) United States Patent
Lin et al.

(10) Patent No.: US 8,053,463 B2
(45) Date of Patent: *Nov. 8, 2011

(54) PPAR ACTIVE COMPOUNDS

(75) Inventors: Jack Lin, Hercules, CA (US);
Byunghun Lee, Marina, CA (US);
Shenghua Shi, San Diego, CA (US);
Chao Zhang, Moraga, CA (US); Dean R. Artis, Kensington, CA (US); Prabha N. Ibrahim, Mountain View, CA (US);
Weiru Wang, Lafayette, CA (US);
Rebecca Zuckerman, Alameda, CA (US)

(73) Assignee: Plexxikon Inc., Berkeley, CA (US)

( * ) Notice: Subject to any disclaimer, the term of this patent is extended or adjusted under 35 U.S.C. 154(b) by 520 days.

This patent is subject to a terminal disclaimer.

(21) Appl. No.: 12/043,069

(22) Filed: Mar. 5, 2008

(65) Prior Publication Data
US 2008/0255201 A1   Oct. 16, 2008

Related U.S. Application Data

(60) Provisional application No. 60/893,871, filed on Mar. 8, 2007.

(51) Int. Cl.
C07D 209/04 (2006.01)
C07D 401/02 (2006.01)
A61K 31/454 (2006.01)
A61K 31/404 (2006.01)

(52) U.S. Cl. ........................ 514/415; 548/452
(58) Field of Classification Search ............... 548/452; 514/415
See application file for complete search history.

(56) References Cited

U.S. PATENT DOCUMENTS

| | | | |
|---|---|---|---|
| 3,489,767 A | 1/1970 | Yamamoto et al. |
| 3,511,841 A | 5/1970 | Archer et al. |
| 3,557,142 A | 1/1971 | Bell et al. |
| 4,150,949 A | 4/1979 | Smith |
| 4,564,610 A | 1/1986 | Rahtz et al. |
| 4,568,649 A | 2/1986 | Bertoglio-Matte |
| 4,626,513 A | 12/1986 | Burton et al. |
| 5,075,313 A | 12/1991 | Yu et al. |
| 5,466,689 A | 11/1995 | Yamamoto et al. |
| 5,747,276 A | 5/1998 | Hoch et al. |
| 5,760,040 A | 6/1998 | Yoshida et al. |
| 5,763,198 A | 6/1998 | Hirth et al. |
| 5,840,485 A | 11/1998 | Lebl et al. |
| 5,877,007 A | 3/1999 | Housey |
| 6,090,912 A | 7/2000 | Lebl et al. |
| 6,178,384 B1 | 1/2001 | Kolossvary |
| 6,243,980 B1 | 6/2001 | Bronstein et al. |
| 6,288,234 B1 | 9/2001 | Griffin |
| 6,294,330 B1 | 9/2001 | Michnick et al. |
| 6,329,389 B1 | 12/2001 | Suzuki et al. |
| 6,331,537 B1 | 12/2001 | Hamilton et al. |
| 6,337,344 B1 | 1/2002 | Defossa et al. |
| 6,395,768 B1 | 5/2002 | Pappolla et al. |
| 6,608,059 B1 | 8/2003 | Daines et al. |
| 6,635,655 B1 | 10/2003 | Jayyosi et al. |
| 6,869,975 B2 | 3/2005 | Abe et al. |
| 7,202,266 B2 | 4/2007 | Arnold et al. |
| 7,259,175 B2 | 8/2007 | Conner et al. |
| 7,348,338 B2 | 3/2008 | Arnold et al. |
| 7,476,746 B2 | 1/2009 | Artis et al. |
| 7,572,806 B2 | 8/2009 | Arnold et al. |
| 2003/0216452 A1 | 11/2003 | Sredy et al. |
| 2004/0006071 A1 | 1/2004 | Simoneau et al. |
| 2004/0077595 A1 | 4/2004 | Cheng et al. |
| 2005/0004115 A1 | 1/2005 | Sharma et al. |
| 2006/0111426 A1 | 5/2006 | Bonnert et al. |
| 2007/0072904 A1 | 3/2007 | Lin et al. |
| 2007/0149603 A1 | 6/2007 | Arnold et al. |
| 2008/0045581 A1 | 2/2008 | Arnold et al. |

FOREIGN PATENT DOCUMENTS

| | | |
|---|---|---|
| EP | 0 154 734 | 8/1990 |
| EP | 0 610 793 A1 | 8/1994 |
| EP | 0 620 214 | 10/1994 |
| EP | 1 219 595 | 7/2002 |
| EP | 1 267 111 | 12/2002 |
| EP | 1 285 908 | 2/2003 |

(Continued)

OTHER PUBLICATIONS

Berger, J. and Wagner, J.A., Physiological and Therapeutic Roles of Peroxisome Proliferator-Activated Receptors, *Diabetes Tech. & Ther.*, 4:163-174 (2002).

(Continued)

*Primary Examiner* — Kahsay T Habte
(74) *Attorney, Agent, or Firm* — Stephen E. Reiter; Foley & Lardner LLP

(57) ABSTRACT

Compounds are described that are active on at least one of PPARα, PPARδ, and PPARγ, which are useful for therapeutic and/or prophylactic methods involving modulation of at least one of PPARα, PPARδ, and PPARγ, wherein the compounds have the formula:

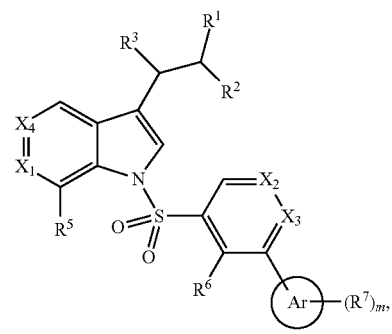

wherein:
$X_2$ and $X_3$ are independently CH or N; and
one of $X_1$ and $X_4$ is N or $CR^4$ and the other of $X_1$ and $X_4$ is N or CH.

8 Claims, No Drawings

FOREIGN PATENT DOCUMENTS

| | | |
|---|---|---|
| EP | 1 661 879 | 5/2006 |
| GB | 1 128 607 | 9/1968 |
| GB | 1 241 637 | 8/1971 |
| GB | 2 407 318 | 4/2005 |
| RU | 2240793 | 11/2004 |
| WO | WO-91/13060 | 9/1991 |
| WO | WO-93/02050 | 2/1993 |
| WO | WO-96/04906 | 2/1996 |
| WO | WO-99/58503 | 11/1999 |
| WO | WO-00/64876 | 11/2000 |
| WO | WO-01/38305 | 5/2001 |
| WO | WO-02/30863 | 4/2002 |
| WO | WO 02/062774 | 8/2002 |
| WO | WO-03/064387 | 8/2003 |
| WO | WO-03/105847 | 12/2003 |
| WO | WO 2004/005253 | 1/2004 |
| WO | WO-2004/007439 | 1/2004 |
| WO | WO-2004/007451 | 1/2004 |
| WO | WO-2004/020409 | 3/2004 |
| WO | WO-2004/056740 | 7/2004 |
| WO | WO-2004/058164 | 7/2004 |
| WO | WO-2004/063190 | 7/2004 |
| WO | WO-2004/092131 | 10/2004 |
| WO | WO-2004/094372 | 11/2004 |
| WO | WO 2005/009958 | 2/2005 |
| WO | WO-2005/037763 | 4/2005 |
| WO | WO-2005/040112 | 5/2005 |
| WO | WO-2005/040114 | 5/2005 |
| WO | WO-2005/044787 | 5/2005 |
| WO | WO-2005/054176 | 6/2005 |
| WO | WO-2005/056522 | 6/2005 |
| WO | WO-2005/060958 | 7/2005 |
| WO | WO-2005/092131 | 10/2005 |
| WO | WO-2005/121141 | 12/2005 |
| WO | WO 2007/030559 | 3/2007 |
| WO | WO 2007/030574 | 3/2007 |

OTHER PUBLICATIONS

Breidert et al., Protective action of the peroxisome proliferator-activated receptor-γ agonist pioglitazone in a mouse model of Parkinson's disease, *Journal of Neurochemistry*, 82:615 (2002).

Combs et al., Inflammatory Mechanisms in Alzheimer's Disease: Inhibition of β-Amyloid-Stimulated Proinflammatory Responses and Neurotoxicity by PPARγ Agonists, *Journal of Neuroscience* 20(2):558 (2000).

Cronet et al., Structure of the PPARα and —γ Ligand Binding Domain in Complex with AZ 242; Ligand Selectivity and Agonist Activation in the PPAR Family, *Structure* (Camb.), 9:699-706 (2001).

Fajas et al., The Organization, Promoter Analysis, and Expression of the Human PPARγ Gene, *J. Biol. Chem.*, 272:18779-18789 (1997).

Feinstein, D.L., Contrasting the neuroprotective and gliotoxic effects of PPARγ agonists, *Drug Discovery Today: Therapeutic Strategies*, 1(1):29-34 (2004).

Fu et al., Oleylethanolamide regulates feeding and body weight through activation of the nuclear receptor PPAR-α, *Nature*, 425:9093 (2003).

Kota et al., An overview on biological mechanisms of PPARδ *Pharmacological Research*, 51:85-94 (2005).

Liebowitz et al., Activation of PPARδ alters lipid metabolism in db/db mice, *FEBS Lett.*, 473:333-336 (2000).

Lohray et al., (−)3-[4-[2-(Phenoxazin-10-yl)ethoxy]phenyl]-2-ethoxypropanoic Acid [(−)DRF 2725]: A Dual PPAR Agonist with Potent Antihyperglycemic and Lipid Modulating Activity, *J. Med. Chem.*, 44:2675-2678 (2001).

Lovett-Racke et al., Peroxisome Proliferator-Activated Receptor α Agonists as Therapy for Autoimmune Disease, *Journal of Immunology*, 172:5790-5798 (2004).

Malhotra et al., Potential therapeutic role of peroxisome proliferator activated receptor-γ agonists in psoriasis, *Expert Opinions in Pharmacotherapy*, 6(9):1455-1461 (2005).

Morgensen et al., Design and Synthesis of Novel PPARα/γ/δ Triple Activators Using a Known PPARα/γ Dual Activator as Structural Template, *Bioorg. & Med. Chem. Lett.*, 13:257-260 (2002).

Miyaura, N. and Suzuki, A., Palladium-Catalyzed Cross-Coupling Reactions of Organoboron Compounds, *Chem. Rev.* 95:2457 (1995).

Oliver et al., A selective peroxisome proliferator-activated receptor δ agonist promotes reverse cholesterol transport, *Proc. Natl. Acad. Sci.*, 98:5306-5311 (2001).

Patel et al., Activation of Peroxisome Proliferator-Activated Receptors in Human Airway Smooth Muscle Cells Has a Superior Anti-inflammatory Profile to Corticosteroids: Relevance for Chronic Obstructive Pulmonary Disease Therapy, *Journal of Immunology*, 2003, 170:2663-2669.

Sastre et al., Nonsteroidal Anti-Inflammatory Drugs and Peroxisome Proliferator-Activated Receptor-γ Agonists Modulate Immunostimulated Processing of Amyloid Precurser Protein through Regulation of β-Secretase, *Journal of Neuroscience*, 23(30):9796 (2003).

Sauerberg et al., Novel Tricyclic-α-alkyloxyphenylpropionic Acids: Dual PPAR α/γ Agonists with Hypolipidemic and Antidiabetic Activity, *J. Med. Chem.* 45:789-804 (2002).

Storer et al., Peroxisome proliferator-activated receptor-gamma agonists inhibit the activation of microglia and astrocytes: Implications for multiple sclerosis, *Journal of Neuroimmunology*, 161:113-122 (2005).

Yousef, J. and Badr, M., Role of Peroxisome Proliferator-Activated Receptors in Inflammation Control, *Journal of Biomedicine and Biotechnology*, (3):156-166 (2004).

U.S. Appl. No. 11/289,751, filed Nov. 29, 2005.
U.S. Appl. No. 11/517,010, filed Sep. 6, 2006.
U.S. Appl. No. 11/517,573, filed Sep. 6, 2006.
U.S. Appl. No. 11/679,792, filed Feb. 27, 2007.
U.S. Appl. No. 11/679,738, filed Feb. 27, 2007.
U.S. Appl. No. 11/679,777, filed Feb. 27, 2007.

Acton et al., Benzoyl 2-methyl indoles as selective PPARγ modulators. Bioorganic & Medicinal Chemistry Letters, 15(2):357-362, 2005.

Aldred, et al., "Peroxisome proliferator-activated receptor gamma is frequently downregulated in a diversity of sporadic nonmedullary thyroid carcinomas," Oncogene 22:3412-3416 (2003).

Alfthan, Surface Plasmon Resonance Biosensors as a Tool in Antibody Engineering, Biosensors & Bioelectronics 13:653-63 (1998).

Al-Obeidi, Peptide and Peptidomimetic Libraries—Molecular Diversity and Drug Design, Mol Biotechnol, 9(3):205-223 (1998).

Amersdorfer and Marks, Phage Libraries for Generation of Anti-Botulinum scFv Antibodies, Methods in Molecular Biology, 145:219-40 (2001).

Azimov, et al., Nucleophilic Substitution Reactions in 6-Chlor-5-Azaindolines, Chem. Heterocycl. Compd., 17(12):1208-1216 (1981).

Bagshaw and Harris, Measurement of Ligand Binding to Proteins, Spectrophotometry and Spectrofluorometry: A Practical Approach, 4:91-114 (1987).

Bagshawe K.D., Antibody-Directed Enzyme Prodrug Therapy: A Review, Drug Dev. Res., 34:220-230, (1995).

Bartlett et al., CAVEAT: A Program to facilitate the structure-derived design of biologically active molecules, In Molecular Recognition: Chemical and Biological Problems, The Proceedings of an International Symposium, University of Exeter, Apr. 1989, Royal Society of Chemistry, Cambridge, 182-196 (1989).

Basanagoudar and Siddappa, Synthesis of indole-3-propionic acids and 3-(3-aminopropyl) indoles., Journal of the Karnatak University, 17:33-42, 1972. Abstract, XP-002483945.

Bell, Spectroscopy in Biochemistry, CRC Press 1:155-194 (1981).

Belletire, J.L., Acylcyanamides: Versatile Synthetic Intermediates, Synthetic Communications, 18:2063-2071 (1988).

Benani et al., Activation of peroxisome proliferator-activated receptor alpha in rat spinal cord after peripheral noxious stimulation, Neurosci Lett., 369(1):59-63, (2004).

Bernotas, et al, 1-(2-aminoethyl)-3-(arylsulfonyl)-1H-indoles as novel 5-HT6 receptor ligands, Bioorg Med Chem Lett, (2004), 14:5499-5502.

Bertolini et al., A New Rational Hypothesis for the Pharmacophore of the Active Metabolite of Leflunomide, a Potent Immunosuppressive Drug, J. Med. Chem., 40:2011-2016, (1997).

Bhagavathula et al., BP-1107[{2-[4-(2,4-Dioxo-thiazolidin-5-ylmethyl)-phenoxy]-ethyl}methyl-amide]: A Novel Synthetic Thiazolidinedione That Inhibits Epidermal Hyperplasia in Psoriatic Skin-Severe-Combined Immunodeficient Mouse Transplants after Topical Application, J Pharmacol Exp Ther., 315(3):996-1004, (2005).

Boehm, et al., Novel Inhibitors of DNA Gyrase: 3D Structure Based Biased Needle Screening, Hit Validation by Biophysical Methods, and 3D Guided Optimization. A Promising Alternative to Random Screening, J. Med. Chem, 43:2664-2674 (2000).

Bohacek, et al., Multiple Highly Diverse Structures Complementary to Enzyme Binding Sites: Results of Extensive Application of a de Novo Design Method Incorporating Combinatorial Growth, J. Am. Chem. Soc., 116:5560-5571 (1994).

Böhm, On the Use of LUDI to Search the Fine Chemicals Directory for Ligands of Proteins of Known Three-Dimensional Structure, J. Comp. Aided Molec. Design, 8:623-632 (1994).

Bolger and Sherman, Computer Modeling of Combining Site Structure of Anti-Hapten Monoclonal Antibodies, Methods Enz., 203:21-45 (1991).

Bourdais et al., Derives sulfures d'indole V(*). Indolethiols-3 et leurs thioethers aminoethyliques et carboxymethyliques. Eur. J. Med. Chem., 9(3): 269-273, 1974.

Brenner et al., Encoded Combinatorial Chemistry, Proc. Natl. Acad. Sci. USA, 89:5381-5383 (1992).

Buchan and Hassall, PPAR agonists as direct modulators of the vessel wall in cardiovascular disease. Med. Res. Rev. 20(5): 350-366, 2000.

Buchheit, et al., The Serotonin 5-HT4 Receptor. 2. Structure—Activity Studies of the Indole Carbazimidamide Class of Agonists, J. Med. Chem., 38:2331-2338 (1995).

Burstein et al., Use of the peroxisome proliferator-activated receptor (PPAR) ligand troglitazone as treatment for refractory breast cancer: a phase II study, Breast Cancer Res. Treat., 79(3):391-7, (2003).

Burstein, S., PPAR: A nuclear receptor with affinity for cannabinoids, Life Sci., 77(14):1674-84, (2005).

Bychikhina, et al., Electrophilic Substitution Reactions in 1-Benzyle-6-Methoxy-7-Cyano-5-Azaindole and 6-Oxo-5-Azaindoline, Chemistry of Heterocyclic Compounds, 18:268-271 (1982).

Camacho et al., Peroxisome Proliferator-Activated Receptor Induces a Clearance Mechanism for the Amyloid-β Peptide, J Neurosci., 24(48):10908-17, (2004).

Cancer (online), (retrieved Feb. 13, 2008). Retrieved from the internet, URL:http://www.nim.nih.gov/medlineplus/cancer.html.

Cancer (online), retrieved from http://en.wikipedia.org/wiki/Cancer (retrieved Jul. 6, 2007).

Cancer [online], [retrieved on Jul. 6, 2007). Retrieved from the Internet,URL: http://www.nlm.nih.gov/medlineplus/cancer.html.

Cantello, et al., [a-(Heterocyclylamino)alkoxy]benzyl]-2,4-thiazolidinediones as Potent Antihyperglycemic Agents, J. Med. Chem., 37:3977-3985 (1994).

Cao, et al., Dual Probes for the Dopamine Transporter and Receptors: Novel Piperazinyl Alkyl-bis(4 19-fluorophenyl)amine Analogues as Potential Cocaine-Abuse Therapeutic Agents, J. Med. Chem., 46:2589-2598 (2003).

Carell et al., New Promise in Combinatorial Chemistry: Synthesis, Characterization, and Screening of Small-Molecule Libraries Solution, Chem. Biol., 3:171-183 (1995).

Chabala, Solid-Phase Combinatorial Chemistry and Novel Tagging Methods for Identifying Leads, Curr Opin Biotechnol, 6(6):633-9 (1995).

Chang et al., Substituted imidazoles as glucagons receptor antagonists. Bioorganic and Medicinal Chem. Lett., 11:2549-2553, 2001.

Chawla et al., PPAR dependent and independent effects on macrophage-gene expression in lipid metabolism and inflammation, Nat Med, 7(1):48-52, (2001).

Checovich et al., Fluorescence Polarization—a New Tool for Cell and Molecular Biology, Nature, 375:254-256 (1995).

ChemDiv, Inc. Product Library, File CHEMCATS, Accession No. 2003:2296132, XP-002385890, Apr. 25, 2003.

Chemical Library Supplier: Ambinter, XP-002385889, May 12, 2004.

Chen, N. and Han, X., Dual Function of Troglitazone in ICAM-1 Gene Expression in Human Vascular Endothelium, Biochem Biophys Res Commun., 282(3):717-22, (2001).

Cheung, et al., Synthesis of 2-chloro-5,7-dihydro-6H-pyrrolo[2,3-d]pyrimidin-6-one, Tetrahedron Letters, 42:999-1001 (2001).

Chong, et al., Molecular dynamics and free-energy calculations applied to affinity maturation in antibody 48G7, PNAS, 96:14330-14335 (1999).

Clark et al., PRO_LIGAND: An Approach to De Novo Molecular Design. 1. Application to the Design of Organic Molecules, J. Comp. Aided Molec. Design, 9:13-32 (1995).

Clark et al., The Nuclear Receptor PPAR and Immunoregulation: PPAR Mediates Inhibition of Helper T Cell Responses, J Immunol., 164(3):1364-71, (2000).

Coe et al., Solution Phase Combinatorial Chemistry, Mol Divers., 4(1):31-38 (1998-99).

Colitis (online), retrieved from http://www.nim.nih.gov/medlineplus/colitis.html (retrieved Dec. 19, 2007).

Colitis [online], [retrieved on Mar. 13, 2008]. Retrieved from the Internet, URL: http://www.nlm.nih.gov/medlineplus/ency/article/000259.htm.

Collagenous Colitis [online], [retrieved on Mar. 13, 2008]. Retrieved from the Internet, URL: http://digestive.niddk.nih.gov/ddiseases/pubs/collagenouscolitis/index.htm.

Collot et al., Heck cross-coupling reaction of 3-iodoindazoles with methyl acrylate: a mild and flexible strategy to design 2-azatryptamines. Tetrahedron Letters, 41(22): 4363-4366, 2000. Abstract, XP-002483946.

Colman, Structure-Based Drug Design, Current Opinion in Struc. Biol., 4: 868-874 (1994).

Communication dated Nov. 19, 2008 in related EP application 05852496.

Communication dated Feb. 29, 2008 in related EP application 05852496.

Communication dated Feb. 5, 2010 in related EP application 04778641.

Communication dated Apr. 30, 2010 in related EP application 08731467.

Communication dated Jun. 24, 2009 in related EP application 05852496.

Communication dated Jul. 28, 2009 in related EP application 05852598.

Communication dated Aug. 14, 2009 in related EP application 06803059.

Cornell, et al., A Second Generation Force Field for the Simulation of Proteins, Nucleic Acids, and Organic Molecules, J. Am. Chem. Soc., 117:5179-5197 (1995).

Corton et al., Perioxisome Proliferator-Activated Receptors, Mediators of Phthalate Ester-Induced Effects in the Male Reproductive Tract, Toxicological Sciences, 83:4-7, (2005).

Cremlyn and Hornby, Sulphonohydrazides and Related Compounds. Part XI. Some Substituted Aryl Ether Sulphonohydrazides, J. of Chem. Soc. C., 1341-1345 (1969).

Cross et al., Selective thromboxane synthetase inhibitors. 2. 3-(1H-imidazol-1-ylmethyl)-2-methyl-1H-indole-l-propanoic acid and analogues, J Med Chem, 29(3):342-346, 1986.

Cuzzocrea et al., Reduction in the Evolution of Murine Type II Collagen-Induced Arthritis by Treatment With Rosiglitazone, a Ligand of the Peroxisome Proliferator-Activated Receptor, Arthritis Rheum, 48(12):3544-56, (2003).

Cwirla et al., Peptides on Phage: A Vast Library of Peptides for Identifying Ligands, Biochemistry, 87:6378-6382 (1990).

Dandliker, et al., Equalibrium and Kinetic Inhibition Assays Based Upon Fluorescence Polarization, Methods in Enzymology, 74:300-334 (1981).

Davis et al., A convenient synthesis of bisindoyl- and indolylaryl-maleic anhydrides, Tetahedron Letters, 31:2353-2356, 1990.

Dharancy et al., Impaired Expression of the Peroxisome Proliferator-Activated Receptor Alpha During Hepatitis C Virus Infection, Gastroenterology, 128(2):334-42, (2005).

Diab, et al. Peroxisome Proliferator-Activated Receptor Agonist 15-Deoxy-(12,14-Prostaglandin J2 Ameliorates Experimental Autoimmune Encephalomyelitis, J. Immunol., 168:2508-2515, (2002).

Diabetes Mellitus (online), retrieved from http://www.merck.com/mmpe/print/sec12/ch158b.html (retrieved Apr. 17, 2007).

Diabetes(online), Retrieved on Mar. 13, 2008). Retrieved from the internet, URL:http://www.merck.com/mmpe/print/sec12/ch158b.html.

Dinh and Armstrong, Synthesis of Ketones and Aldehydes via Reactions of Weinreb-Type Amides on Solid Support, Tet. Lett., 37:1161-1164 (1996).

Dolle and Nelson, Comprehensive survey of Combinatorial library synthesis: 1998, J Comb Chem, 1(4):235-82 (1999).

Donini and Kollman, Calculation and Prediction of Binding Free Energies for the Matrix Metalloproteinases, J. Med. Chem., 43:4180-4188 (2000).

Downs, et al., Similarity Searching and Clustering of Chemical-Structure Databases Using Molecular Property Data, J. Chem. Inf. Comput. Sci., 34:1094-1102 (1994).

Eczema (online), (retrieved on Mar. 13, 2008). Retrieved from the internet, URL: http://www.nim.nih.gov/medlineplus/eczema.html. Eczema (online), retrieved from http://www.nim.nih.gov/medlineplus/eczema.html (retrieved Dec. 19, 2007).

Eils, et al., Complete Regioselectivity in Staurosporine Chromophore Formation, Synthesis, 2:275-281 (1998).

Eliseev and Lehn, Dynamic Combinatorial Chemistry: Evolutionary Formation and Screening of Molecular Libraries, Current Topics in Microbiology & Immunology, 243:159-172 (1999).

Enjalbal et al., Mass Spectrometry in Combinatorial Chemistry, Mass Spectrometry Reviews, 19:139-161 (2000).

FDA Clinical Trials [online], [retrieved on Mar. 13, 2008]. Retrieved from the Internet, URL: http://www.fda.gov/oashi/clinicaltrials/default.html.

Feinstein, et al., Peroxisome Proliferator-Activated Receptor Agonists Prevent Experimental Autoimmune Encephalomyelitis, Ann. Neurol., 51:694-702, (2002).

Felder, E.R., The Challenge of Preparing and Testing Combinatorial Compound Libraries in the Fast Lane, at the Front End of Drug Development, Chimia 48:531-541 (1994).

Filla, et al., Novel Potent 5-HT1F Receptor Agonists: Structure-Activity Studies of a Series of Substituted N-[3-Methyl-4-piperidinyl)-1H-pyrrolo[3,2-b]pyridine-5-yl]amides, J. Med. Chem., 46:3060-3071 (2003).

Fivash et al., BIAcore for Macromolecular Interaction, Current Opinion in Biotechnology, 9:97-101 (1998).

Freidinger RM., Nonpeptidic Ligands for Peptide and Protein Receptors, Current Opinion in Chemical Biology, 3:395-406 (1999).

Frolund, et al., Novel Class of Potent 4-Arylalkyl Substituted 3-Isoxazolol GABAA Antagonists: Synthesis, Pharmacology, and Molecular Modeling, J. Med. Chem., 45:2454-2468 (2002).

Gallop et al., Applications of Combinatorial Technologies to Drug Discovery. 1. Background and Peptide Combinatorial Libraries, J. Med. Chem., 37:1233-1251 (1994).

Galun et al., Ethers of indoxylic acid, J. Heterocyclic Chem., 16:221-224, 1979.

Garcia et al., A Novel synthesis of 3-cyanoindoles and a new route to indole-3-carboxylic acid derivatives, Tetrahedron Letters, 26(15):1827-1830, 1985.

Gingras and Harpp, A Practical, One-Step Synthesis of Primary Thiols Under Mild and Neutral Conditions Using Bis(Triorganotin) Sulfades, Tet. Lett., 31(10):1397-1400 (1990).

Glintborg et al., Pioglitazone Treatment Increases Spontaneous Growth Hormone (GH) Secretion and Stimulated GH Levels in Polycystic Ovary Syndrome, J Clin Endocrinol Metab, 90(10):5605-12, (2005).

Golub et al., Molecular classification of cancer: Class discovery and class prediction by gene expression monitoring. Science, 286: 531-537, 1999.

Goodford, P., A Computational Procedure for Determining Energetically Favorable Binding Sites on Biologically Important Macromolecules, J. Med. Chem., 28:849-857 (1985).

Goodsell and Olson, Automated Docking of Substrates to Proteins by Simulated Annealing, Proteins: Structure, Function, and Genetics 8:195-202 (1990).

Gordon and Ford, Detection of Peroxides and Their Removal, The Chemist's Companion: A Handbook of Practical Data, Techniques, and References p. 437 (1972).

Gordon et al., Applications of Combinatorial Technologies to Drug Discovery. 2. Combinatorial Organic Synthesis, Library Screening Strategies, and Future Directions, J. Med. Chem., 37:1385-1401 (1994).

Gram H., Phage Display in Proteolysis and Signal Transduction, Combinatorial Chemistry & High Throughput Screening, 2:19-28 (1999).

Granneman et al., Member of the Peroxisome Proliferator-Activated Receptor Family of Transcription Factors Is Differentially Expressed by Oligodendrocytes, J Neurosci Res., 51(5):563-73, (1998).

Gravert and Janda, Synthesis on Soluble Polymers: New Reactions and the Construction of Small Molecules, Curr Opin Chem Biol, 1(1):107-113 (1997).

Guida, C., Software for Structure-Based Drug Design, Current Opinion in Struc. Biol., 4:777-781 (1994).

Guo et al., A new total synthesis of chuangxinmycin and the study of its stereoisomers. CAPLUS, 1988:454536.

Hague, et al., Potent, Low-Molecular-Weight Non-Peptide Inhibitors of Malarial Aspartyl Protease Plasmepsin II, J. Med. Chem., 42:1428-1440 (1999).

Hanselman et al., A cDNA-Dependant Scintillation Proximity Assay for Quantifying Apolipoprotein A1, J. Lipid Res., 38:2365-2373 (1997).

Harris, S.G. and Phipps, R.P., The nuclear receptor PPAR gamma is expressed by mouse T lymphocytes and PPAR gamma agonists induce apoptosis, Eur J Immunol., 31(4):1098-1105 (2001).

Heck, et al., Conversion of Primary Amides to Nitriles by Aldehyde-Catalyzed Water Transfer, J. Org. Chem., 61:6486-6487 (1996).

Heim and Tsien, Engineering Green Fluorescent Protein for Improved Brightness, Longer Wavelengths and Fluorescence Resonance Energy Transfer, Curr. Biol., 6:178-182 (1996).

Helberger, et al., Zur Kenntnis Organischer Sulfosauren V. Mitteilung: Synthesen des 1, 4-butansultons, Justus Liebigs Ann Chem, (1954), 586:158-163.

Heneka et al., Acute treatment with the PPAR agonist pioglitazone and ibuprofen reduces glial inflammation and Aβ1-42 levels in APPV717I transgenic mice, Brain., 128(Pt 6):1442-53, (2005).

Heneka et al., Peroxisome Proliferator-Activated Receptor Ligands Reduce Neuronal Inducible Nitric Oxide Synthase Expression and Cell Death in Vivo, J. Neurosci., 20:6862-6867, (2000).

Holzapfel et al, The synthesis of a keto-a-amino acid, a key intermediate in the synthesis of monatin, a new natural sweetener, Synthetic Communications, 23(18): 2511-26, 1993.

Hortelano et al., Contribution of Cyclopentenone Prostaglandins to the Resolution of Inflammation Through the Potentiation of Apoptosis in Activated Macrophages, J Immunol., 165(11):6525-31, (2000).

Houghten et al., Generation and Use of Synthetic Peptide Combinatorial Libraries for Basic Research and Drug Discovery, Nature, 354:84-86 (1991).

Houghten, Peptide Libraries: Criteria and Trends, Trends in Genetics, 9(7):235-239 (1993).

Houghton, Parallel Array and Mixture-Based Synthetic Combinatorial Chemistry: Tools for the Next Millennium, Annu Rev Pharmacol Toxicol, 40:273-282 (2000).

Hughes-Jones, et al., Synthesis of Rh Fv Phage-Antibodies Using VH and VL Germline Genes, British Journal of Haematology, 105:811-816 (1999).

Hurd and Bauer, A Novel Rearrangement of Hydroxamic Acids Using Sulfonyl Chlorides, J. Am. Chem., 76:2791-2792 (1954).

Imamoto, et al., A One-Flask Conversion of Carboxylic Acids into Nitriles, Synthesis, 142-143 (1983).

International Preliminary Report on Patentability dated Jan. 23, 2006 in related application PCT/US2004/023234.

International Preliminary Report on Patentability dated Mar. 11, 2008 in related application PCT/US2006/034747.

International Preliminary Report on Patentability dated Jun. 5, 2007 in related application PCT/US2005/043271.
International Preliminary Report on Patentability dated Jun. 5, 2007 in related application PCT/US2005/043412.
International Preliminary Report on Patentability dated Sep. 8, 2009 in related application PCT/US2008/055955.
International Search Report dated Nov. 1, 2004 in related application PCT/US2004/023234.
International Search Report dated Apr. 27, 2007 in related application PCT/US2006/034747.
International Search Report dated Jul. 19, 2006 in related application PCT/US2005/043271.
International Search Report dated Jul. 19, 2006 in related application PCT/US2005/043412.
International Search Report dated Jul. 21, 2008 in related application PCT/US2008/055955.
Jackson et al., Peroxisome Proliferator-Activated Receptor Activators Target Human Endothelial Cells to Inhibit Leukocyte-Endothelial Cell Interatcion, Arterioscler Thromb Vasc Biol., 19:2094-104, (1999).
Jarvis and Patrick, Clustering Using a Similarity Measure Based on Shared Near Neighbors, IEEE Transactions on Computers, 11:1025-1034 (1973).
Jiang et al., PPAR agonists inhibit production of monocyte inflammatory cytokines, Nature, 391(6662):82-6, (1998).
Joseph-McCarthy D., Computational Approaches to Structure-Based Ligand Design, Pharmacology & Therapeutics, 84:179-191 (1999).
Juby, et al., Preparation and Antiinflammatory Properties of Some 1-Substituted 3-(5-Tetrazolylmethyl) Indoles and Homologs, J. of Med. Chem., 12:396-401 (1969).
Kahl et al., A Multiple-Approach Scintillation Proximity Assay to Measure the Association Between Ras and Raf, Anal. Biochem., 243:282-283 (1996).
Kawahito et al., 15-deoxy-(12,14-PGJ2 induces synoviocyte apoptosis and suppresses adjuvant-induced arthritis in rats, J Clin Invest., 106(2):189-97, (2000).
Ketcha et al., Synthesis of alkyl-substituted N-protected indoles via acylation and reductive deoxygenation. J. Organic Chemistry, 54(18): 4350-4356, 1989.
Kim and Kahn, A Merger of Rational Drug Design and Combinatorial Chemistry: Development and Application of Peptide Secondary Structure Mimetics, Combinatorial Chemistry & High Throughput Screening, 3:167-183 (2000).
Kim et al., Effects of peroxisome proliferator-activated receptor agonists on LPS-induced neuronal death in mixed cortical neurons: associated with iNOS and COX-2, Brain Res., 941(1-2):1-10, (2002).
Kim et al., p38 kinase mediates nitric oxide-induced apoptosis of chondrocytes through the inhibition of protein kinase C by blocking autophosphorylation, Cell Death Differ., 12, 201-212, (2005).
Kintscher et al., Peroxisome proliferator-activated receptor and retinoid X receptor ligands inhibit monocyte chemotactic protein-1-directed migration of monocytes. Eur J Pharmacol., 401(3):259-70, (2000).
Kirkpatrick et al., Structure-Based Drug Design: Combinatorial Chemistry and Molecular Modeling, Combinatorial Chemistry & High Throughput Screening, 2:211-221 (1999).
Kitamura, et al., Synthesis of Quinolines and 2H-Dihydropyrroles by Nucleophilic Substitution at the Nitrogen Atom of Oxime Derivatives, Synthesis, 15:2415-2426 (2003).
Kubinyi H., Editor, 3D QSAR in drug design, Theory methods and applications, Springer, (1998), vol. 2-3, TOC and pp. 243-244.
Kundu et al., Combinatorial Chemistry: Polymer Supported Synthesis of Peptide and Non-Peptide Libraries, Progress in Drug Research, 53:89-156 (1999).
Kuntz et al., A Geometric Approach to Macromolecule-Ligand Interactions, J. Mol. Biol., 161:269-288 (1982).
Kuntz et al., Structure-Based Molecular Design, Acc. Chem. Res., 27:117-123 (1994).
Kuwano et al, Highly enantioselective synthesis of chiral 3-substitued indulines by catalytic asymmetric hydrogenation of indoles, Organic Letters, 6(13): 2213-2215, 2004. XP-002483944.
Lala et al, Role of nitric oxide in tumor progression: Lessons from experimental tumors, Cancer and Metastasis Reviews, 17(1):91-106, 1998.
Lam et al., A New Type of Synthetic Peptide Library for Identifying Ligand-Binding Activity, Nature, 354:82-84 (1991).
Lance and Williams, A General Theory of Classificatory Sorting Strategies 1. Hierarchical Systems, The Computer Journ., 9:373-380 (1967).
Lebl et al., One-Bead-One-Structure Combinational Libraries, Biopolymers, 37:177-198 (1995).
Levkovskaya et al., Synthesis of (3-Indolylsulfanyl)alkanecarboxylic acids, Russian Journal of Organic Chemistry, 38(11): 1641-1646, 2002.
Liparoto and Ciardelli, Biosensor Analysis of the Interleukin-2 Receptor Complex, Journal of Molecular Recognition, 12:316-321 (1999).
Lipinski et al., Experimental and Computational Approaches to Estimate Solubility and Permeability in Drug Discovery and Development Settings, Advanced Drug Delivery Reviews, 23:3-25 (1997).
Lipschultz et al., Experimental Design for Analysis of Complex Kinetics Using Surface Plasmon Resonance, Methods, 20(3):310-318 (2000).
Lo Verme et al., The Nuclear Receptor Peroxisome Proliferator-Activated Receptor-a Mediates the Anti-Inflammatory Actions of Palmitoylethanolamide, Mol Pharmacol., 67(1):15-9, (2005).
Lynch, et al., Pyrazolo[3,4-b]pyridines: Syntheses, reactions and nuclear magnetic resonance spectra, Canadian Journ. Of Chem., 66:420-428 (1988).
Madden et al., Synthetic Combinatorial Libraries: Views on Techniques and Their Application, Perspectives in Drug Discovery and Design, 2:269-282 (1995).
Mahindroo et al., Novel indole-based peroxisome proliferator-activated receptor agonists: Design, SAR, structural biology, and biological activities, J Med Chem, 48:8194-8208, 2005.
Malmborg and Borrebaeck, BIAcore As a Tool in Antibody Engineering, Journal of Immunological Methods, 183:7-13 (1995).
Malmqvist et al, Biomolecular Interaction Analysis: Affinity Biosensor Technologies for Functional Analysis of Proteins, Current Opinion in Chemical Biology, 1:378-383 (1997).
Malmqvist, M., Biacore: An Affinity Biosensor System for Characterization of Biomolecular Interactions, Biochemical Society Transactions, 27:335-340 (1999).
Markiewicz et al., Synthetic Oligonucleotide Combinatorial Libraries and Their Applications, II Farmaco, 55:174-177 (2000).
Martin, Y., Computer-Assisted Rational Drug Design, Methods Enz., 203:587-613 (1991).
Marx, et al., Macrophages in Human Atheroma Contain PPAR Differentiation-Dependent Peroxisomal Proliferator-Activated Receptor (PPAR) Expression and Reduction of MMP-9 Activity through PPAR Activation in Mononuclear Phagocytes in Vitro, Am J Path, 153(1):17-23, 1998.
Massova and Kollman, Computational Alanine Scanning to Probe Protein 13 Protein Interactions: A Novel Approach to Evaluate Binding Free Energies, Journ. of Amer. Chem. Soc., 121(36):8133-8143 (1999).
Mazéas, et al., Synthesis of New Melatoninergic Ligands Including Azaindole Moiety, Heterocycles, 50:1065-1080 (1999).
McGovern, et al., A Common Mechanism Underlying Promiscuous Inhibitors from Virtual and High Throughput Screening, J. Med. Chem., 45:1712-1722 (2002).
Meng et al., Automated Docking With Grid-Based Energy Evaluation, J. Compt. Chem., 13:505:524 (1992).
Merritt, A., 1Colution Phase Combinatorial Chemistry, Comb Chem High Throughput Screen, 1(2):57-72 (1998).
Miller et al., FLOG: A System to Select Quasi-Flexible Ligands Complementary to a Receptor of Known Three-Dimensional Structure, J. Comp. Aided Molec. Design, 8:153-174 (1994).
Miranker and Karplus, Functionality Maps of Binding Sites: Simultaneous Search Method, Proteins: Structure, Function, and Genetics, 11:29-34 (1991).
Mitra et al., Fluorescence Resonance Energy Transfer Between Blue-Emitting and Red-Shifted Excitation Derivatives of the Green Fluorescent Protein, Gene, 173:13-17 (1996).

Molina, et al., One Pot Conversion of Alkyl Halides into Thiols Under Mild Conditions, Tetrahedron Lett., 26:469-472 (1985).

Muto et al., Pioglitazone improves the phenotype and molecular defects of a targeted Pkd1 mutant, Human Molecular Genetics, 11(15):1731-1742, (2002).

Nagatsu et al., Changes in cytokines and neurotrophins in Parkinson's disease, J Neural Transm Suppl. (60):277-90, (2000).

Natarajan, C. and Bright, J.J., Peroxisome proliferator-activated receptor-gamma agonists inhibit experimental allergic encephalomyelitis by blocking IL-12 production, IL-12 signaling and Th1 differentiation, Genes Immun., 3:59-70, (2002).

Neidle and Jenkins, Molecular Modeling to Study DNA Interaction by Anti-Tumor Drugs, Methods Enz., 203:433-458 (1991).

Nichols et al., Development of a Scintillation Proximity Assay for Peroxisome Proliferator-Activated Receptor γ Ligand Binding Domain, Anal. Biochem., 257:112-119 (1998).

Niino, et al., Amelioration of experimental autoimmune encephalomyelitis in C57BL/6 mice by an agonist of peroxisome proliferator-activated receptor, J Neuroimmunol, 116:40-48, (2001).

Nolte, et al., Ligand Binding and Co-Activator Assembly of the Peroxisome Proliferator-Activated Receptor, Nature, 395:137-143 (1998).

Notice of Allowance dated Nov. 1, 2006 in U.S. Appl. No. 10/893,134.

Notice of Allowance dated May 8, 2007 in U.S. Appl. No. 10/937,791.

Notice of Allowance dated Sep. 14, 2007 in U.S. Appl. No. 10/937,791.

Okamoto et al., Inhibition of NF-B signaling by fenofibrate, a peroxisome proliferator-activated receptor-a ligand, presents a therapeutic strategy for rheumatoid arthritis, Clin Exp Rheumatol, 23:323-30, (2005).

O'Shannessy and Winzor, Interpretation of Deviations From Pseudo-First-Order Kinetic Behavior in the Characterization of Ligand Binding by Biosensor Technology, Analytical Biochemistry, 236:275-283 (1996).

O'Shannessy, D., Determination of Kinetic Rate and Equilibrium Binding Constants for Macromolecular Interactions: a Critique of the Surface Plasmon Resonance Literature, Current Opinions in Biotechnology, 5:65-71 (1994).

Oster and Harris, Generation and Reactions of the Dianion of 3-Hydroxy-5-methylisoxazole, a Convenient β-Keto Amide Synthon. Total Synthesis of Muscimol, J. Org. Chem., 48:4307-4311 (1983).

Padilla et al., Human B Lymphocytes and B Lymphomas Express PPAR and Are Killed by PPAR Agonists, Clin Immunol, 103(1):22-33, (2002).

Parker et al., Development of High Throughput Screening Assays Using Fluorescence Polarization: Nuclear Receptor-Ligand-Binding and Kinase/Phosphatase Assays, J Biomol Screen, 5:77-88 (2000).

Pearlman and Charifson, Are Free Energy Calculations Useful in Practice? A Comparison with Rapid Scoring Functions for the p38 MAP Kinase Protein System, J. Med. Chem., 44:3417-3423 (2001).

Perrin D., Nucleic Acids for Recognition and Catalysis: Landmarks, Limitations, and Looking to the Future, Combinatorial Chemistry & High Throughput Screening, 3:243-269 (2000).

Peters et al., Growth, Adipose, Brain, and Skin Alterations Resulting from Targeted Disruption of the Mouse Peroxisome Proliferator-Activated Receptor β(d), Mol Cell Biol. 20(14):5119-28, (2000).

Plunkett and Ellman, A Silicon-Based Linker for Traceless Solid-Phase Synthesis, J. Org. Chem., 60:6006-6007 (1995).

Poul et al., Selection of Tumor-Specific Internalizing Human Antibodies From Phage Libraries, J Mol Biol, 301:1149-1161 (2000).

Price et al, Summary Report on the ISOBM TD-4 Workshop: Analysis of 56 Monoclonal Antibodies Against the MUC1 Mucin, Tumour Biology, 19(1):1-20 (1998).

Raulin, J., Human immunodeficiency virus and host cell lipids. Interesting pathways in research for a new HIV therapy, Prog Lipid Res, 41:27-65, (2002).

Ricote et al, The peroxisome proliferator-activated receptor is a negative regulator of macrophage activation, Nature, 391:79-82, (1998).

Ripka, et al., Aspartic Protease Inhibitors Designed from Computer-Generated Templates Bind as Predicted, Org. Lett., 15:2309-2312 (2001).

Rybczynski et al, Benzoxazinones as PPARγ agonists.2.SAR of the amide substituent and in vivo results in a type 2 diabetes model, J Med Chem, (2004), 47:196-209.

Sakamoto, et al., Condensed Heteroaromatic Ring Systems. Part 24.1,2 Synthesis of Rigidin, a Pyrrolo[2,3-d]Pyrimidine Marine Alkaloid, J. Chem. Soc., 5:459-464 (1996).

Scholtz, M., Das Verhalten des Methyl-indols gegen Aldehyde und Ameisensäure, Chem. Ber. 46:2139-2146 (1913).

Schweizer and Hindsgaul, Combinatorial Synthesis of Carbohydrates, Curr Opin Chem Biol, 3(3):291-298 (1999).

Seehra et al., Preparation of indole derivatives as phospholipase enzyme inhibitors for treatment of inflammatory conditions, CAPLUS, (2007), 2003:1275.

Seela, et al., 7-Desaza-Isostere von 2'-Desoxyxanthosin und 2'-Desoxyspongosin—Synthese via Glycosylierung von 2,4-Dichlor-7H-pyrrolo[2,3-d]pyrimidin, Liebigs Ann. Chem., 312-320 (1985).

Seethala, R. and Prabhavathi, B., Homogenous Assays: AlphaScreen, Handbook of Drug Screening, Marcel Dekker, New York, pp. 106-110 (2001).

Selvin, P., Fluorescence Resonance Energy Transfer, Meth. in Enzymology, 246:300-334 (1995).

Shang-Shing et al., "Synthetic applications of Tricarbonyl(phenylsulfonyl)-cyclohexadienyl iron(I) complex." Tetrahedron Letters, 37(30):5373-5376, 1996.

Sheets et al., Efficient Construction of a Large Nonimmune Phage Antibody Library: the Production of High-Affinity Human Single-Chain Antibodies to Protein Antigens, (published erratum) Proc Natl Acad Sci USA, 95:6157-6162 (1998).

Shu et al., Activation of PPARa Reduces Secretion of Matrix Metalloproteinase 9 but Not Interleukin 8 from Human Monocytic THP-1 Cells, Biochem Biophys Res Commun., 267(1):345-9, (2000).

Siegel et al., "Mass Spectral Analysis of a Protein Complex Using Single-Chain Antibodies Selected on a Peptide Target: Applications to Functional Genomics," Journal of Molecular Biology 302:285-293 (2000).

Silverman, The Org. Chem. of Drug Design and Drug Action, Academic Press, Inc., San Diego, 1992, pp. 4-51.

Slomiany, Bronislaw L. & Slomiany, Amalie, Role of epidermal growth factor receptor transactivation in PPAR-dependent suppression of *Helicobacter pylori* interference with gastric mucin synthesis, Inflammopharmacology, 12(2):177-88, (2004).

Staels et al., Activation of human aortic smooth-muscle cells is inhibited by PPARa but not by PPAR activators, Nature 393:790-793, (1998).

Sun, C., Recent Advances in Liquid-Phase Combinatorial Chemistry, Combinatorial Chemistry & High Throughput Screening, 2:299-318 (1999).

Sun, et al., Design, Synthesis, and Evaluations of Substituted 3-[3- or 4-Carboxyethylpyrrol-2-yl)methylidenyl]indolin-2-ones as Inhibitors of VEGF, FGF, and PDGF Receptor Tyrosine Kinases, J. Med. Chem, 42:5120-5130 (1999).

Supplementary Search Report dated Jun. 25, 2008 in related EP application 04778641.

Trost et al., 2-Alkoxybenzo-1,3-dithiole 1,1,3,3-tetraoxide: A carbonyl 1,1-dipole synthon. J. Am. Chem. Soc., 106(8): 2469-2471, 1984.

Undenfriend et al., Scintillation Proximity Assay: A Sensitive and Continuous Isotopic Method for Monitoring Ligand/Receptor and Antigen/Antibody Interactions, Anal. Biochem, 161:494-500 (1987).

US Notice of Allowance dated Nov. 17, 2008 in related U.S. Appl. No. 11/289,656.

US Notice of Allowance dated Dec. 29, 2009 in related U.S. Appl. No. 11/679,738.

US Notice of Allowance dated Apr. 7, 2009 in related U.S. Appl. No. 12/001,026.

US Notice of Allowance dated Sep. 10, 2008 in related U.S. Appl. No. 11/679,777.

US Notice of Allowance dated Sep. 24, 2008 in related U.S. Appl. No. 11/679,792.
US Office Action dated Aug. 29, 2008 in related U.S. Appl. No. 11/679,738.
US Office Action dated Jan. 16, 2009 in related U.S. Appl. No. 11/517,573.
US Office Action dated Jan. 21, 2009 in related U.S. Appl. No. 12/001,026.
US Office Action dated Jan. 22, 2010 in related U.S. Appl. No. 11/517,573.
US Office Action dated Jan. 24, 2006 in related U.S. Appl. No. 10/937,791.
US Office Action dated Oct. 16, 2007 in related U.S. Appl. No. 11/289,781.
US Office Action dated Nov. 21, 2007 in related U.S. Appl. No. 11/289,656.
US Office Action dated Nov. 4, 2009 in related U.S. Appl. No. 11/289,781.
US Office Action dated Dec. 12, 2005 in related U.S. Appl. No. 10/893,134.
US Office Action dated Dec. 19, 2007 in related U.S. Appl. No. 11/517,573.
US Office Action dated Dec. 27, 2007 in related U.S. Appl. No. 11/679,738.
US Office Action dated Feb. 13, 2007 in related U.S. Appl. No. 10/937,791.
US Office Action dated Feb. 24, 2009 in related U.S. Appl. No. 11/289,781.
US Office Action dated Feb. 5, 2009 in related U.S. Appl. No. 11/679,738.
US Office Action dated Mar. 18, 2008 in related U.S. Appl. No. 11/289,781.
US Office Action dated Mar. 26, 2008 in related U.S. Appl. No. 11/69,777.
US Office Action dated Mar. 4, 2010 in related U.S. Appl. No. 11/289,781.
US Office Action dated Apr. 1, 2008 in related U.S. Appl. No. 11/679,792.
US Office Action dated May 26, 2009 in related U.S. Appl. No. 11/517,573.
US Office Action dated May 30, 2008 in related U.S. Appl. No. 11/289,656.
US Office Action dated Jun. 23, 2008 in related U.S. Appl. No. 11/517,573.
US Office Action dated Jun. 26, 2006 in related U.S. Appl. No. 10/893,134.
US Office Action dated Jul. 10, 2007 in related U.S. Appl. No. 11/517,573.
US Office Action dated Jul. 10, 2008 in related U.S. Appl. No. 11/679,738.
US Office Action dated Jul. 11, 2006 in related U.S. Appl. No. 10/937,791.
US Office Action dated Jul. 29, 2008 in related U.S. Appl. No. 12/001,026.
US Office Action dated Sep. 17, 2008 in related U.S. Appl. No. 11/289,781.
US Office Action dated Sep. 21, 2005 in related U.S. Appl. No. 10/893,134.
Van Regenmortel, Use of Biosensors to Characterize Recombinant Proteins, Developments in Biological Standardization, 83:143-51 (1994).
VanZandt et al., Discovery of 3-[(4,5,7-Trifluorobenzothiazol-2-yl)methyl]indole-N-acetic acid (Lidorestat) and congeners as highly potent and selective inhibitors of aldose reductase for treatment of chronic diabetic complications. J.Med.Chem., 48:3141-3152, 2005.
Vely, et al., BIAcore Analysis to Test Phosphopeptide-SH2 Domain Interactions, Methods in Molecular Biology, 121:313-321 (2000).
Weidner-Wells, et al., "The Synthesis and Antimicrobial Evaluation of a New Series of Isoxazolinyl Oxazolidinones," Bioorg. & Med. Chem. Lett. 14:3069-3072 (2004).
Wessjohann, Synthesis of Natural-Product-Based Compound Libraries, Curr Opin Chem Biol, 4(3):303-309 (2000).
Willett, P., "Chemical Similarity Searching," J. Chem. Inf. Comput. Sci. 38:983-996 (1998).
Wilson and Hyslop, "Application of the Grignard Reaction to some Acetylenic Compounds. Part I. Preparation of Diacetylenic Glycols," J. Chem. Soc. 2612-2618 (1923).
Woods et al., Localization of PPARd in murine central nervous system: expression in oligodentrocytes and neurons, Brain Res. 975:10-21, (2003).
Xu et al., Structural basis for antagonist-mediated recruitment of nuclear co-repressors by PPARa, Nature, 415:813-817, (2002).
Xu, et al., "Molecular Recognition of Fatty Acids by Peroxisome Proliferator-Activated Receptors," Molecular Cell 3:397-403 (1999).
Yamasaki et al., Functional changes in rheumatoid fibroblast-like synovial cells through activation of peroxisome proliferator-activated receptor mediated signalling pathway, Clin Exp Immunol., 129:379-84, (2002).
Yato et al., Reduction of carboxylic esters with triethyl silane in the combined use of titanium tetrachloride and trimethylsilyl trifluoromethanesulfonate, Tetrahedron, 57:5353-5359, 2001.
Zhang et al., Differential Regulation of Chemokine Gene Expression by 15-Deoxy-(12,14 Prostaglandin J21,2, J Immunol., 166:7104-11, (2001).

PPAR ACTIVE COMPOUNDS

RELATED PATENT APPLICATIONS

This application claims priority to U.S. Provisional App. No. 60/893,871, entitled "PPAR Active Compounds", filed Mar. 8, 2007, which is incorporated herein by reference in its entirety all purposes.

FIELD OF THE INVENTION

The present invention relates to the field of modulators for members of the family of nuclear receptors identified as peroxisome proliferator-activated receptors.

BACKGROUND OF THE INVENTION

The following description is provided solely to assist the understanding of the reader. None of the references cited or information provided is admitted to be prior art to the present invention. Each of the references cited herein is incorporated by reference in its entirety, to the same extent as if each reference were individually indicated to be incorporated by reference herein in its entirety.

The peroxisome proliferator-activated receptors (PPARs) form a subfamily in the nuclear receptor superfamily. Three isoforms, encoded by separate genes, have been identified thus far: PPARγ, PPARα, and PPARδ.

There are two PPARγ isoforms expressed at the protein level in mouse and human, γ1 and γ2. They differ only in that the latter has 30 additional amino acids at its N terminus due to differential promoter usage within the same gene, and subsequent alternative RNA processing. PPARγ2 is expressed primarily in adipose tissue, while PPARγ1 is expressed in a broad range of tissues.

Murine PPARα was the first member of this nuclear receptor subclass to be cloned; it has since been cloned from humans. PPARα is expressed in numerous metabolically active tissues, including liver, kidney, heart, skeletal muscle, and brown fat. It is also present in monocytes, vascular endothelium, and vascular smooth muscle cells. Activation of PPARα induces hepatic peroxisome proliferation, hepatomegaly, and hepatocarcinogenesis in rodents. These toxic effects are not observed in humans, although the same compounds activate PPARα across species.

Human PPARδ was cloned in the early 1990s and subsequently cloned from rodents. PPARδ is expressed in a wide range of tissues and cells; with the highest levels of expression found in the digestive tract, heart, kidney, liver, adipose, and brain.

The PPARs are ligand-dependent transcription factors that regulate target gene expression by binding to specific peroxisome proliferator response elements (PPREs) in enhancer sites of regulated genes. PPARs possess a modular structure composed of functional domains that include a DNA binding domain (DBD) and a ligand binding domain (LBD). The DBD specifically binds PPREs in the regulatory region of PPAR-responsive genes. The DBD, located in the C-terminal half of the receptor, contains the ligand-dependent activation domain, AF-2. Each receptor binds to its PPRE as a heterodimer with a retinoid X receptor (RXR). Upon binding an agonist, the conformation of a PPAR is altered and stabilized such that a binding cleft, made up in part of the AF-2 domain, is created and recruitment of transcriptional coactivators occurs. Coactivators augment the ability of nuclear receptors to initiate the transcription process. The result of the agonist-induced PPAR-coactivator interaction at the PPRE is an increase in gene transcription. Downregulation of gene expression by PPARs appears to occur through indirect mechanisms. (Bergen, et al., *Diabetes Tech. & Ther.*, 2002, 4:163-174).

The first cloning of a PPAR (PPARα) occurred in the course of the search for the molecular target of rodent hepatic peroxisome proliferating agents. Since then, numerous fatty acids and their derivatives, including a variety of eicosanoids and prostaglandins, have been shown to serve as ligands of the PPARs. Thus, these receptors may play a central role in the sensing of nutrient levels and in the modulation of their metabolism. In addition, PPARs are the primary targets of selected classes of synthetic compounds that have been used in the successful treatment of diabetes and dyslipidemia. As such, an understanding of the molecular and physiological characteristics of these receptors has become extremely important to the development and utilization of drugs used to treat metabolic disorders.

Kota, et al., *Pharmacological Research*, 2005, 51:85-94, provides a review of biological mechanisms involving PPARs that includes a discussion of the possibility of using PPAR modulators for treating a variety of conditions, including chronic inflammatory disorders such as atherosclerosis, arthritis and inflammatory bowel syndrome, retinal disorders associated with angiogenesis, increased fertility, and neurodegenerative diseases.

Yousef, et al., *Journal of Biomedicine and Biotechnology*, 2004(3):156-166, discusses the anti-inflammatory effects of PPARα, PPARγ and PPARδ agonists, suggesting that PPAR agonists may have a role in treating neuronal diseases such as Alzheimer's disease, and autoimmune diseases such as inflammatory bowel disease and multiple sclerosis. A potential role for PPAR agonists in the treatment of Alzheimer's disease has been described in Combs, et al., *Journal of Neuroscience* 2000, 20(2):558, and such a role for PPAR agonists in Parkinson's disease is discussed in Breidert, et al., *Journal of Neurochemistry*, 2002, 82:615. A potential related function of PPAR agonists in treatment of Alzheimer's disease, that of regulation of the APP-processing enzyme BACE, has been discussed in Sastre, et al., *Journal of Neuroscience*, 2003, 23(30):9796. These studies collectively indicate PPAR agonists may provide advantages in treating a variety of neurodegenerative diseases by acting through complementary mechanisms.

Discussion of the anti-inflammatory effects of PPAR agonists is also available in Feinstein, *Drug Discovery Today: Therapeutic Strategies*, 2004, 1(1):29-34, in relation to multiple sclerosis and Alzheimer's disease; Patel, et al., *Journal of Immunology*, 2003, 170:2663-2669 in relation to chronic obstructive pulmonary disease and asthma (COPD); Lovett-Racke, et al., *Journal of Immunology*, 2004, 172:5790-5798 in relation to autoimmune disease; Malhotra, et al., *Expert Opinions in Pharmacotherapy*, 2005, 6(9):1455-1461, in relation to psoriasis; and Storer, et al., *Journal of Neuroimmunology*, 2005, 161:113-122, in relation to multiple sclerosis.

This wide range of roles for the PPARs that have been discovered suggest that PPARα, PPARγ and PPARδ may play a role in a wide range of events involving the vasculature, including atherosclerotic plaque formation and stability, thrombosis, vascular tone, angiogenesis, cancer, pregnancy, pulmonary disease, autoimmune disease, and neurological disorders.

Among the synthetic ligands identified for PPARs are thiazolidinediones (TZDs). These compounds were originally developed on the basis of their insulin-sensitizing effects in animal pharmacology studies. Subsequently, it was found that TZDs induced adipocyte differentiation and increased expression of adipocyte genes, including the adipocyte fatty acid-binding protein aP2. Independently, it was discovered that PPARγ interacted with a regulatory element of the aP2 gene that controlled its adipocyte-specific expression. On the basis of these seminal observations, experiments were preformed that determined that TZDs were PPARγ ligands and agonists and demonstrate a definite correlation between their in vitro PPARγ activities and their in vivo insulin-sensitizing actions. (Bergen, et al., supra).

Several TZDs, including troglitazone, rosiglitazone, and pioglitazone, have insulin-sensitizing and anti-diabetic activity in humans with type 2 diabetes and impaired glucose tolerance. Farglitazar is a very potent non-TZD PPAR-γ-selective agonist that was recently shown to have anti-diabetic as well as lipid-altering efficacy in humans. In addition to these potent PPARγ ligands, a subset of the non-steroidal anti-inflammatory drugs (NSAIDs), including indomethacin, fenoprofen, and ibuprofen, have displayed weak PPARγ and PPARα activities. (Bergen, et al., supra).

The fibrates, amphipathic carboxylic acids that have been proven useful in the treatment of hypertriglyceridemia, are PPARα ligands. The prototypical member of this compound class, clofibrate, was developed prior to the identification of PPARs, using in vivo assays in rodents to assess lipid-lowering efficacy. (Bergen, et al., supra).

Fu et al., *Nature*, 2003, 425:9093, demonstrated that the PPARα binding compound, oleylethanolamide, produces satiety and reduces body weight gain in mice.

Clofibrate and fenofibrate have been shown to activate PPARα with a 10-fold selectivity over PPARγ. Bezafibrate acts as a pan-agonist that shows similar potency on all three PPAR isoforms. Wy-14643, the 2-arylthioacetic acid analogue of clofibrate, is a potent murine PPARα agonist as well as a weak PPARγ agonist. In humans, all of the fibrates must be used at high doses (200-1,200 mg/day) to achieve efficacious lipid-lowering activity.

TZDs and non-TZDs have also been identified that are dual PPARγ/α agonists. By virtue of the additional PPARα agonist activity, this class of compounds has potent lipid-altering efficacy in addition to anti-hyperglycemic activity in animal models of diabetes and lipid disorders. KRP-297 is an example of a TZD dual PPARγ/α agonist (Fajas, *J. Biol. Chem.*, 1997, 272:18779-18789); furthermore, DRF-2725 and AZ-242 are non-TZD dual PPARγ/α agonists. (Lohray, et al., *J. Med. Chem.*, 2001, 44:2675-2678; Cronet, et al., *Structure* (Camb.), 2001, 9:699-706).

In order to define the physiological role of PPARδ, efforts have been made to develop novel compounds that activate this receptor in a selective manner. Amongst the α-substituted carboxylic acids previously described, the potent PPARδ ligand L-165041 demonstrated approximately 30-fold agonist selectivity for this receptor over PPARγ, and it was inactive on murine PPARα (Liebowitz, et al., 2000, *FEBS Lett.*, 473:333-336). This compound was found to increase high-density lipoprotein levels in rodents. It was also reported that GW501516 was a potent, highly-selective PPARδ agonist that produced beneficial changes in serum lipid parameters in obese, insulin-resistant rhesus monkeys. (Oliver et al., *Proc. Natl. Acad. Sci.*, 2001, 98:5306-5311).

In addition to the compounds discussed above, certain thiazole derivatives active on PPARs have been described. (Cadilla, et al., Internat. Appl. PCT/US01/149320, Internat. Publ. WO 02/062774, incorporated herein by reference in its entirety.)

Some tricyclic-α-alkyloxyphenylpropionic acids have been described as dual PPARα/γ agonists in Sauerberg, et al., *J. Med. Chem.* 2002, 45:789-804.

A group of compounds that are stated to have equal activity on PPARα/γ/δ is described in Morgensen, et al., *Bioorg. & Med. Chem. Lett.*, 2002, 13:257-260.

Oliver et al., describes a selective PPARδ agonist that promotes reverse cholesterol transport. (Oliver, et al., supra)

Yamamoto et al., U.S. Pat. No. 3,489,767 describes "1-(phenylsulfonyl)-indolyl aliphatic acid derivatives" that are stated to have "antiphlogistic, analgesic and antipyretic actions." (Col. 1, lines 16-19.)

Kato, et al., European patent application 94101551.3, Publication No. 0 610 793 A1, describes the use of 3-(5-methoxy-1-p-toluenesulfonylindol-3-yl)propionic acid (page 6) and 1-(2,3,6-triisopropylphenylsulfonyl)-indole-3-propionic acid (page 9) as intermediates in the synthesis of particular tetracyclic morpholine derivatives useful as analgesics.

SUMMARY OF THE INVENTION

The present invention relates to compounds active on PPARs, which are useful for a variety of applications including, for example, therapeutic and or prophylactic methods involving modulation of at least one of PPARα, PPARδ, and PPARγ. Included are compounds that have pan-activity across the PPAR family (i.e., PPARα, PPARδ, and PPARγ), as well as compounds that have significant specificity (at least 5-, 10-, 20-, 50-, or 100-fold greater activity) on a single PPAR, or on two of the three PPARs.

In one aspect, the invention provides compounds of Formula I as follows:

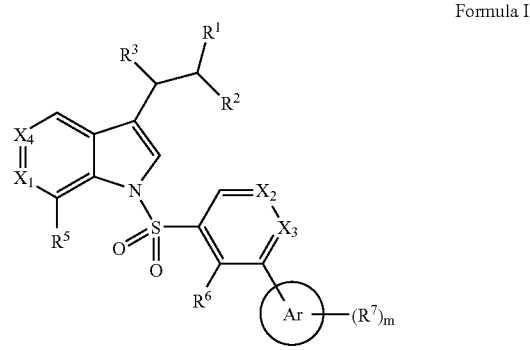

Formula I all salts, prodrugs, tautomers and isomers thereof,
wherein:
  $X_2$ and $X_3$ are independently CH or N;
  one of $X_1$ and $X_4$ is N or $CR^4$ and the other of $X_1$ and $X_4$ is N or CH;
  Ar is aryl or heteroaryl;
  $R^1$ is selected from the group consisting of —C(O)$OR^8$, —C(O)$NR^9R^{10}$, and a carboxylic acid isostere;
  $R^2$ and $R^3$ are each hydrogen, or $R^2$ and $R^3$ combine to for optionally substituted 3-7 membered monocyclic cycloalkyl;
  $R^4$ is hydrogen, fluoro, chloro, methoxy or fluoro substituted methoxy;
  $R^5$ is hydrogen, fluoro, chloro, $C_{1-3}$ alkyl, or fluoro substituted $C_{1-3}$ alkyl;
  $R^6$ is hydrogen, fluoro, chloro, $C_{1-3}$ alkyl, or fluoro substituted $C_{1-3}$ alkyl;

R⁷ at each occurrence is independently selected from the group consisting of halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —NO₂, —CN, —OR¹¹, —NR¹¹R¹², —C(Z)NR¹¹R¹², —C(Z)R¹³, —S(O)₂NR¹¹R¹², —S(O)R¹³, —OC(Z)R¹³, —C(Z)OR¹¹, —C(NH)NR¹⁴R¹⁵, —NR¹¹C(Z)R¹³, —NR¹¹S(O)₂R¹³, —NR¹¹C(Z)NR¹¹R¹², and —NR¹¹S(O)₂NR¹¹R¹²;

R⁸ is selected from the group consisting of hydrogen, lower alkyl, phenyl, 5-7 membered monocyclic heteroaryl, 3-7 membered monocyclic cycloalkyl, and 5-7 membered monocylic heterocycloalkyl, wherein phenyl, monocyclic heteroaryl, monocyclic cycloalkyl and monocyclic heterocycloalkyl are optionally substituted with one or more substituents selected from the group consisting of halogen, —OH, —NH₂, lower alkyl fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, —OH, —NH₂, lower alkoxy, fluoro substituted lower alkoxy, lower alkylthio and fluoro substituted lower alkylthio, provided, however, that when R⁸ is lower alkyl, any substitution on the lower alkyl carbon bound to the O of OR⁸ is fluoro;

R⁹ and R¹⁰ are independently selected from the group consisting of hydrogen, lower alkyl, phenyl, 5-7 membered monocyclic heteroaryl, 3-7 membered monocyclic cycloalkyl, and 5-7 membered monocyclic heterocycloalkyl, wherein phenyl, monocyclic heteroaryl, monocyclic cycloalkyl and monocyclic heterocycloalkyl are optionally substituted with one or more substituents selected from the group consisting of halogen, —OH, —NH₂, lower alkyl, fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, —OH, —NH₂, lower alkoxy, fluoro substituted lower alkoxy, lower alkylthio and fluoro substituted lower alkylthio, provided, however, that when R⁹ and or R¹⁰ is lower alkyl, any substitution on the lower alkyl carbon bound to the N of NR⁹R¹⁰ is fluoro; or R⁹ and R¹⁰ together with the nitrogen to which they are attached form a 5-7 membered monocyclic heterocycloalkyl or a 5 or 7 membered nitrogen containing monocyclic heteroaryl, wherein the monocyclic heterocycloalkyl or monocyclic nitrogen containing heteroaryl is optionally substituted with one or more substituents selected from the group consisting of halogen, —OH, —NH₂, lower alkyl fluoro substituted lower alkyl, lower alkoxy, fluoro substituted lower alkoxy, lower alkylthio, and fluoro substituted lower alkylthio;

R¹¹, R¹², R¹⁴, and R¹⁵ at each occurrence are independently selected from the group consisting of hydrogen, optionally substituted lower alkyl, optionally substituted C₃₋₆ alkenyl, provided, however, that when R¹¹, R¹², R¹⁴, or R¹⁵ is optionally substituted C₃₋₆ alkenyl, no alkene carbon thereof is bound to the O of any OR¹¹ or N of any NR¹¹, NR¹², NR¹⁴ or NR¹⁵; optionally substituted C₃₋₆ alkynyl, provided, however, that when R¹¹, R¹², R¹⁴, or R¹⁵ is optionally substituted C₃₋₆ alkynyl, no alkyne carbon thereof is the O of any OR¹¹ or N of any NR¹¹, NR¹², NR¹⁴ or NR¹⁵; optionally substituted cycloalkyl, optionally substituted heterocycloalkyl, optionally substituted aryl, and optionally substituted heteroaryl, or R¹⁴ and R¹⁵ combine with the nitrogen to which they are attached to form a 5-7 membered optionally substituted heterocycloalkyl or a 5 or 7 membered optionally substituted nitrogen containing heteroaryl;

R¹³ at each occurrence is independently selected from the group consisting of optionally substituted lower alkyl, optionally substituted C₃₋₆ alkenyl, provided, however, that when R¹³ is optionally substituted C₃₋₆ alkenyl, no alkene carbon thereof is bound to the S of any S(O)ₙR¹³ or the C of any C(Z)R¹³; optionally substituted C₃₋₆ alkynyl, provided, however, that when R¹³ is optionally substituted C₃₋₆ alkynyl, no alkyne carbon thereof is bound to the S of any S(O)ₙR¹³ or the C of any C(Z)R¹³; optionally substituted cycloalkyl, optionally substituted heterocycloalkyl, optionally substituted aryl, and optionally substituted heteroaryl;

Z is O or S;

n is 0, 1 or 2; and m is 0, 1, 2, 3, 4, or 5, provided, however, that the compound is not

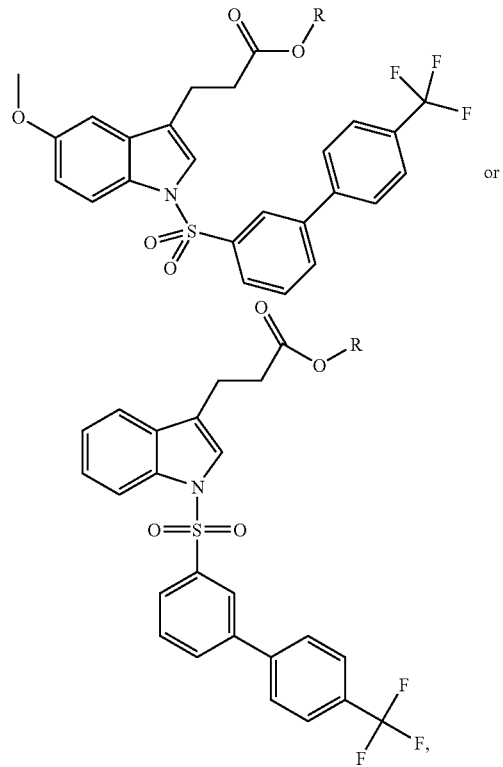

wherein R is H, methyl or ethyl.

In some embodiments of compounds of Formula I, R² and R³ are hydrogen. In some embodiments, R¹ is —COOR⁸, preferably —COOH. In some embodiments, R² and R³ are hydrogen and R¹ is —COOR, preferably —COOH. In some embodiments, R² and R³ are hydrogen and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl.

In some embodiments of compounds of Formula I, at least one of R⁴ and R⁵ is hydrogen. In some embodiments, R⁴ is hydrogen. In some embodiments, $R^2$, $R^3$ and $R^4$ are hydrogen. In some embodiments, $R^4$ is hydrogen and $R^1$ is —COOR$^8$, preferably —COOH. In some embodiments, $R^4$ is hydrogen and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^4$ are hydrogen and $R^1$ is —COOR$^8$, preferably —COOH. In some embodiments, $R^2$, $R^3$ and $R^4$ are hydrogen and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^4$ are hydrogen, $R^1$ is —COOR$^8$, preferably —COOH and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl.

In some embodiments of compounds of Formula I, $R^5$ is hydrogen and $X_1$ is N or $CR^4$. In some embodiments, $R^2$, $R^3$ and $R^5$ are hydrogen and $X_1$ is N or $CR^4$. In some embodiments, $R^5$ is hydrogen, $X_1$ is N or $CR^4$ and $R^1$ is —COOR$^8$, preferably —COOH. In some embodiments, $R^5$ is hydrogen, $X_1$ is N or $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_1$ is N or $CR^4$, and $R^1$ is —COOR$^8$, preferably —COOH. In some embodiments, $R^2$, $R^3$ and $R^5$ are hydrogen, $X_1$ is N or $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_1$ is N or $CR^4$, $R^1$ is —COOR$^8$, preferably —COOH and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl.

In some embodiments of compounds of Formula I, $R^5$ is hydrogen and $X_4$ is N or $CR^4$. In some embodiments, $R^2$, $R^3$ and $R^5$ are hydrogen and $X_4$ is N or $CR^4$. In some embodiments, $R^5$ is hydrogen, $X_4$ is N or $CR^4$ and $R^1$ is —COOR$^8$, preferably —COOH. In some embodiments, $R^5$ is hydrogen, $X_4$ is N or $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_4$ is N or $CR^4$, and $R^1$ is —COOR$^8$, preferably —COOH. In some embodiments, $R^2$, $R^3$ and $R^5$ are hydrogen, $X_4$ is N or $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_4$ is N or $CR^4$, $R^1$ is —COOR$^8$, preferably —COOH and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl.

In some embodiments of compounds of Formula I, $R^5$ is hydrogen, $X_4$ is CH, and $X_1$ is $CR^4$. In some embodiments, $R^2$, $R^3$ and $R^5$ are hydrogen, $X_4$ is CH, and $X_1$ is $CR^4$. In some embodiments, $R^5$ is hydrogen, $X_4$ is CH, $X_1$ is $CR^4$ and $R^1$ is —COOR$^8$, preferably —COOH. In some embodiments, $R^5$ is hydrogen, $X_4$ is CH, $X_1$ is $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_4$ is CH, $X_1$ is $CR^4$, and $R^1$ is —COOR$^8$, preferably —COOH. In some embodiments, $R^2$, $R^3$ and $R^5$ are hydrogen, $X_4$ is CH, $X_1$ is $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_4$ is CH, $X_1$ is $CR^4$, $R^1$ is —COOR$^8$, preferably —COOH and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl.

In some embodiments of compounds of Formula I, $R^5$ is hydrogen, $X_1$ is CH, and $X_4$ is $CR^4$. In some embodiments, $R^2$, $R^3$ and $R^5$ are hydrogen, $X_1$ is CH, and $X_4$ is $CR^4$. In some embodiments, $R^5$ is hydrogen, $X_1$ is CH, $X_4$ is $CR^4$ and $R^1$ is —COOR$^8$, preferably —COOH. In some embodiments, $R^5$ is hydrogen, $X_1$ is CH, $X_4$ is $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_1$ is CH, $X_4$ is $CR^4$, and $R^1$ is —COOR$^8$, preferably —COOH. In some embodiments, $R^2$, $R^3$ and $R^5$ are hydrogen, $X_1$ is CH, $X_4$ is $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $R^2$, $R^3$ and $R^5$ are hydrogen, $X_1$ is CH, $X_4$ is $CR^4$, $R^1$ is —COOR$^8$, preferably —COOH and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl.

In some embodiments of compounds of Formula I, one of $X_2$ and $X_3$ is N and the other of $X_2$ and $X_3$ is CH. In some embodiments, $X_2$ is N and $X_3$ is CH. In some embodiments, $X_2$ is N, $X_3$ is CH, and $R^6$ is hydrogen. In some embodiments, $X_2$ is CH and $X_3$ is N. In some embodiments, $X_2$ is CH, $X_3$ is N, and $R^6$ is hydrogen. In some embodiments, both $X_2$ and $X_3$ are CH. In some embodiments, both $X_2$ and $X_3$ are CH and $R^6$ is hydrogen. In some embodiments, $X_1$, $X_2$ and $X_3$ are CH, $X_4$ is $CR^4$, and $R^6$ is hydrogen. In some embodiments, $X_1$, $X_2$ and $X_3$ are CH, $X_4$ is $CR^4$, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $X_1$, $X_2$ and $X_3$ are CH, $X_4$ is $CR^4$, $R^6$ is hydrogen and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $X_1$, $X_2$, $X_3$ and $X_4$ are CH, and $R^1$ is —COOR$^8$, preferably —COOH. In some embodiments, $X_1$, $X_2$, $X_3$ and $X_4$ are CH, $R^2$, $R^3$, and $R^6$ are hydrogen and $R^1$ is —COOR$^8$, preferably —COOH. In some embodiments, $X_1$, $X_2$, $X_3$ and $X_4$ are CH, $R^2$, $R^3$ and $R^6$ are hydrogen, $R^1$ is —COOR$^8$, preferably —COOH, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl. In some embodiments, $X_1$, $X_2$ and $X_3$ are CH, $R^5$ is hydrogen, $X_4$ is $CR^4$, and $R^1$ is —COOR$^8$, preferably —COOH. In some embodiments, $X_1$, $X_2$ and $X_3$ are CH, $X_4$ is $CR^4$, $R^2$, $R^3$, $R^5$ and $R^6$ are hydrogen and $R^1$ is —COOR$^8$, preferably —COOH. In some embodiments, $X_1$, $X_2$ and $X_3$ are CH, $X_4$ is $CR^4$, $R^2$, $R^3$, $R^5$ and $R^6$ are hydrogen, $R^1$ is —COOR$^8$, preferably —COOH, and Ar is phenyl or monocyclic heteroaryl, preferably phenyl, pyridinyl, pyrimidinyl, pyrazolyl, imidazolyl, thiazolyl, isothiazolyl, oxazolyl, or isoxazolyl.

In some embodiments of compounds of Formula I, Ar is phenyl or monocyclic heteroaryl. In some embodiments, Ar is phenyl, pyridinyl, pyrimidinyl, pyrazolyl, imidazolyl, thiazolyl, isothiazolyl, oxazolyl, or isoxazolyl.

In some embodiments of compounds of Formula I, further to any of the embodiments contemplated herein of Formula I, $R^7$ is $R^{16}$, wherein $R^{16}$ at each occurrence is independently selected from the group consisting of —OH, —NH$_2$, —NO, —CN —C(O)OH, —S(O)$_2$NH$_2$, —C(O)NH$_2$, —OR$^{17}$, —SR$^{17}$, —NR$^{18}$R$^{17}$, —NR$^{18}$C(O)R$^{17}$, —NR$^{18}$ S(O)$_2$R$^{17}$, —S(O)$_2$R$^{17}$, —C(O)R$^{17}$, —C(O)OR$^{17}$, —C(O)NR$^{18}$R$^{17}$, —S(O)$_2$NR$^{18}$R$^{17}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as R$^{16}$, or as substituents of lower alkyl, are optionally substituted with one or more substituents selected from the group consisting of —OH, —NH$_2$, —NO$_2$, —CN, —C(O)OH, —S(O)$_2$NH$_2$, —C(O)NH$_2$, —OR$^{19}$, —SR$^{19}$, —NR$^{18}$R$^{19}$, —NR$^{18}$C(O)R$^{19}$, —NR$^{18}$S(O)$_2$R$^{19}$, —S(O)$_2$R$^{19}$, —C(O)R$^{19}$, —C(O)OR$^{19}$, —C(O)NR$^{18}$R$^{19}$, —S(O)$_2$NR$^{18}$R$^{19}$, halogen, lower alkyl, fluoro substituted lower alkyl, and cycloalkylamino;

R$^{17}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of any OR$^{17}$, SR$^{17}$, or NR$^{17}$ is fluoro, cycloalkyl, heterocycloalkyl, aryl or heteroaryl; wherein cycloalkyl, heterocycloalkyl, aryl, and heteroaryl as R$^{17}$ or as substituents of lower alkyl are optionally substituted with one or more substituents selected from the group consisting of —OH, —NH$_2$, —NO$_2$, —CN, —C(O)OH, —S(O)$_2$NH$_2$, —C(O)NH$_2$, —OR$^{19}$, —SR$^{19}$, —NR$^{18}$R$^{19}$, —NR$^{18}$C(O)R$^{19}$, —NR$^{18}$S(O)$_2$R$^{19}$, —S(O)$_2$R$^{19}$, —C(O)R$^{19}$, —C(O)OR$^{19}$, —C(O)NR$^{18}$R$^{19}$, —S(O)$_2$NR$^{18}$R$^{19}$, halogen, lower alkyl, fluoro substituted lower alkyl, and cycloalkylamino;

R$^{18}$ at each occurrence is independently hydrogen or lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and R$^{19}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of any OR$^{19}$, SR$^{19}$, or NR$^{19}$ is fluoro.

In some embodiments of compounds of Formula I, R$^{16}$ is selected from the group consisting of halogen, —OH, —NH$_2$, —NO$_2$, —CN, lower alkyl, lower alkoxy, lower alkylthio, mono-alkylamino, di-alkylamino, and —NR$^{20}$R$^{21}$ wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, or cycloalkylamino, wherein R$^{20}$ and R$^{21}$ combine with the nitrogen to which they are attached to form a 5-7 membered heterocycloalkyl or 5-7 membered heterocycloalkyl substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio.

In some embodiments, compounds of Formula I have the structure selected from the following sub-generic structures Formula Ia, Formula Ib, Formula Ic, Formula Id, Formula Ie, Formula If, Formula Ig, and Formula Ih:

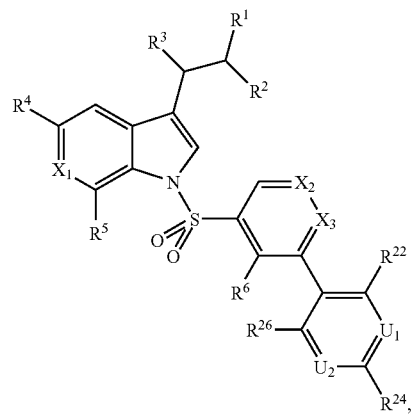
Formula Ia

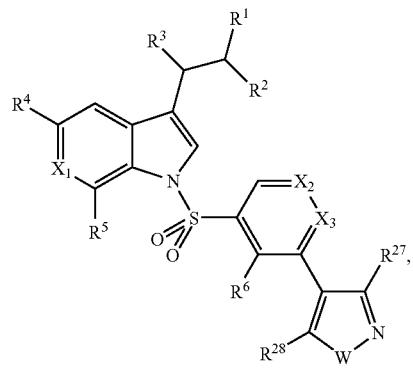
Formula Ib

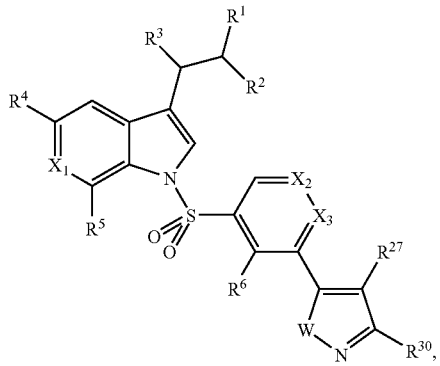
Formula Ic

11
-continued

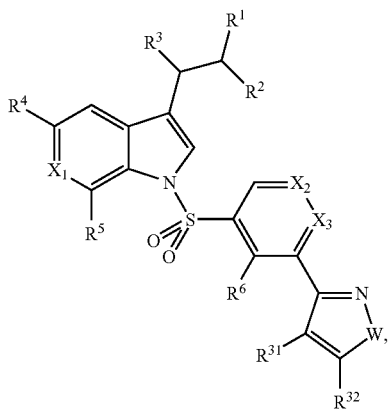
Formula Id

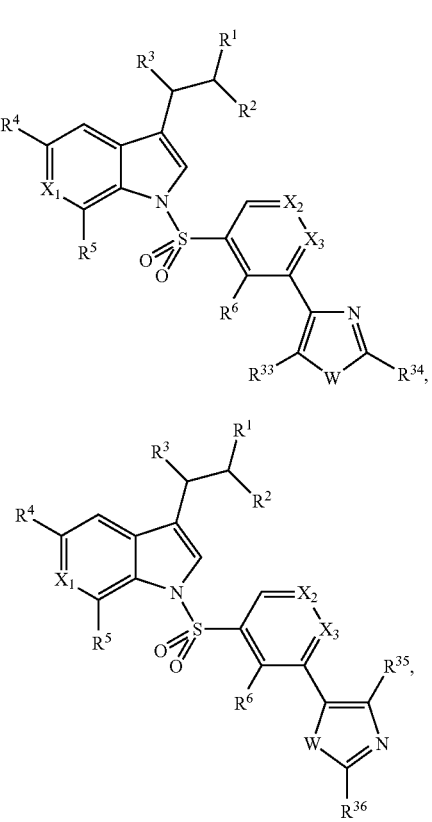
Formula Ie

Formula If

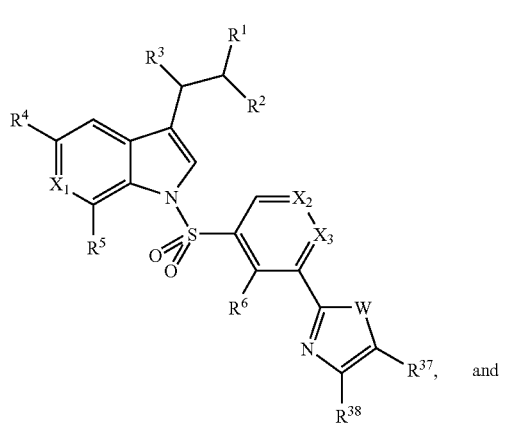
Formula Ig and

12
-continued

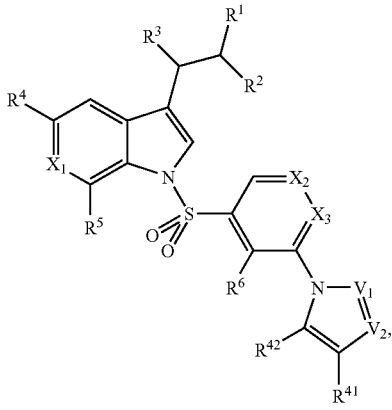
Formula Ih all salts, prodrugs, tautomers and isomers thereof,
wherein:
$X_1$, $X_2$, $X_3$, $R^1$, $R^2$, $R^3$, $R^4$, $R^5$ and $R^6$ are as defined for Formula I;
$U_1$ is N or $CR^{23}$;
$U_2$ is N or $CR^{25}$;
$V_1$ is N or $CR^{39}$;
$V_2$ is N or $CR^{40}$;
W is O, S, or $NR^{43}$;
$R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$, are independently hydrogen or $R^7$ as defined in Formula I; and
$R^{43}$ is selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —C(Z)$NR^{11}R^{12}$, —C(Z)$R^{13}$, —S(O)$_2NR^{11}R^{12}$, —S(O)$_2R^{13}$, —C(Z)$OR^{11}$, and —C(NH)$NR^{14}R^{15}$, wherein $R^{11}$, $R^{12}$, $R^{13}$, $R^{14}$, and $R^{15}$ are as defined for Formula I.

In some embodiments of compounds of Formulae Ia-Ih, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$, are independently hydrogen or $R^{16}$, wherein $R^{16}$ is as defined, preferably wherein $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$, are selected from the group consisting of hydrogen, halogen, —OH, —$NH_2$, —$NO_2$, —CN, lower alkyl, lower alkoxy, lower alkylthio, mono-alkylamino, di-alkylamino, and —$NR^{20}R^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —$NH_2$, lower alkyl, fluoro substituted lower alkyl, lower alkoxy, fluoro substituted lower alkoxy, lower alkylthio, and fluoro substituted lower alkylthio, and $R^{43}$ is selected from the group consisting of hydrogen, —C(O)O, —S(O)$_2NH_2$, —C(O)$NH_2$, —S(O)$_2R^{17}$, —C(O)$R^{17}$, —C(O)$OR^{17}$, —C(O)$NR^{18}R^{17}$, —S(O)$_2NR^{18}R^{17}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{43}$, or as substituents of lower alkyl, are optionally substituted with one or more substituents selected from the group consisting of —OH, —$NH_2$, —$NO_2$, —CN, —C(O)OH, —$S(O)_2NH_2$, —C(O)$NH_2$, —$OR^{19}$, —$SR^{19}$, —$NR^{18}R^{19}$, —$NR^{18}$C(O)$R^{19}$, —$NR^{18}S(O)_2R^{19}$, —$S(O)_2R^{19}$, —C(O)$R^{19}$, —C(O)$OR^{19}$, —C(O)$NR^{18}R^{19}$, —$S(O)_2NR^{18}R^{19}$, halogen, lower alkyl, fluoro substituted lower alkyl, and cycloalkylamino, wherein $R^{17}$, $R^{18}$, and $R^{19}$ are as defined, preferably $R^{43}$ is hydrogen or lower alkyl optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In some embodiments of compounds of Formula Ia, $R^{25}$ and $R^{26}$ are hydrogen. In some embodiments, $R^{26}$ is hydrogen and $U_1$ and $U_2$ are N. In some embodiments, $R^{26}$ is hydrogen, $U_2$ is CH and $U_1$ is N. In some embodiments, $R^{26}$ is hydrogen, $U_2$ is CH and $U_1$ is $CR^{23}$. In some embodiments, $R^{26}$ is hydrogen, $U_2$ is N or CH, $U_1$ is N or $CR^{23}$, and $R^{22}$, $R^{23}$ and $R^{24}$ are hydrogen or $R^7$, preferably hydrogen or $R^{16}$, more preferably $R^{22}$, $R^{23}$ and $R^{24}$ are selected from the group consisting of hydrogen, halogen, —OH, —$NH_2$, —$NO_2$, —CN, lower alkyl, lower alkoxy, lower alkylthio, mono-alkylamino, di-alkylamino, and —$NR^{20}R^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —$NH_2$, lower alkyl, fluoro substituted lower alkyl, lower alkoxy, fluoro substituted lower alkoxy, lower alkylthio, and fluoro substituted lower alkylthio.

In some embodiments of compounds of Formula Ia, $R^{22}$ and $R^{26}$ are H, $U_2$ is CH, $U_1$ is CH, and $R^{24}$ is independently hydrogen or $R^7$, preferably hydrogen or $R^{16}$, preferably $R^{16}$, more preferably $R^{24}$ is independently selected from the group consisting of halogen, —OH, —$NH_2$, —$NO_2$, —CN, lower alkyl, lower alkoxy, lower alkylthio, mono-alkylamino, di-alkylamino, and —$NR^{20}R^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —$NH_2$, lower alkyl, fluoro substituted lower alkyl, lower alkoxy, fluoro substituted lower alkoxy, lower alkylthio, and fluoro substituted lower alkylthio.

In some embodiments of compounds of Formula Ia, $R^{22}$, $R^{24}$, and $R^{26}$ are H, $U_2$ is CH, $U_1$ is $CR^{23}$, and $R^{23}$ is independently hydrogen or $R^7$, preferably hydrogen or $R^{16}$, preferably $R^{16}$, more preferably $R^{23}$ is independently selected from the group consisting of halogen, —OH, —$NH_2$, —$NO_2$, —CN, lower alkyl, lower alkoxy, lower alkylthio, mono-alkylamino, di-alkylamino, and —$NR^{20}R^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —$NH_2$, lower alkyl, fluoro substituted lower alkyl, lower alkoxy, fluoro substituted lower alkoxy, lower alkylthio, and fluoro substituted lower alkylthio.

In some embodiments of compounds of Formula Ia, $R^{24}$ and $R^{26}$ are H, $U_2$ is CH, $U_1$ is CH and $R^{22}$ is independently hydrogen or $R^7$, preferably hydrogen or $R^{16}$, preferably $R^{16}$, more preferably $R^{22}$ is independently selected from the group consisting of halogen, —OH, —$NH_2$, —$NO_2$, —CN, lower alkyl, lower alkoxy, lower alkylthio, mono-alkylamino, di-alkylamino, and —$NR^{20}R^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —$NH_2$, lower alkyl fluoro substituted lower alkyl, lower alkoxy, fluoro substituted lower alkoxy, lower alkylthio, and fluoro substituted lower alkylthio.

In some embodiments of compounds of Formula Ia, $R^{26}$ is H, $U_2$ is CH, $U_1$ is CH and $R^{22}$ and $R^{24}$ are independently hydrogen or $R^7$, preferably hydrogen or $R^{16}$, preferably $R^{16}$, more preferably $R^{22}$ and $R^{24}$ are independently selected from the group consisting of halogen, —OH, —$NH_2$, —$NO_2$, —CN, lower alkyl, lower alkoxy, lower alkylthio, mono-alkylamino, di-alkylamino, and $R^{20}R^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —$NH_2$, lower alkyl, fluoro substituted lower alkyl, lower alkoxy, fluoro substituted lower alkoxy, lower alkylthio, and fluoro substituted lower alkylthio.

In some embodiments of compounds of Formula Ia, $R^{26}$ and $R^{22}$ are H, $U_2$ is CH, $U_1$ is $CR^{23}$ and $R^{23}$ and $R^{24}$ are independently hydrogen or $R^7$, preferably hydrogen or $R^{16}$, preferably $R^{16}$, more preferably $R^{23}$ and $R^{24}$ are independently selected from the group consisting of halogen, —OH, —$NH_2$, —$NO_2$, —CN, lower alkyl, lower alkoxy, lower alkylthio, mono-alkylamino, di-alkylamino, and —$NR^{20}R^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio.

In some embodiments of compounds of Formula Ia, $R^{26}$ and $R^{24}$ are H, $U_2$ is CH, $U_1$ is $CR^{23}$ and $R^{22}$ and $R^{23}$ are independently hydrogen or $R^7$, preferably hydrogen or $R^{16}$, preferably $R^{16}$, more preferably $R^{22}$ and $R^{23}$ are independently selected from the group consisting of halogen, —OH, —NH$_2$, —NO$_2$, —CN, lower alkyl, lower alkoxy, lower alkylthio, mono-alkylamino, di-alkylamino, and —NR$^{20}$R$^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio.

In some embodiments of compounds of Formula Ib, W is $NR^{43}$. In some embodiments, W is $NR^{43}$, $R^{43}$ is hydrogen or lower alkyl optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and $R^{27}$ and $R^{28}$ are independently selected from the group consisting of hydrogen, halogen, —OH, —NH$_2$, —NO$_2$, —CN, lower alkyl, lower alkoxy, lower alkylthio, mono-alkylamino, di-alkylamino, and —NR$^{20}$R$^{21}$, wherein lower alkyl and the alkyl chain(s) of lower alkoxy, lower alkylthio, mono-alkylamino or di-alkylamino are optionally substituted with one or more, preferably 1, 2, or 3 substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, wherein $R^{20}$ and $R^{21}$ combine with the nitrogen to which they are attached to form a 5-7 membered heterocycloalkyl or 5-7 membered heterocycloalkyl substituted with one or more substituents selected from the group consisting of fluoro. —OH, —NH$_2$, lower alkyl, fluoro substituted lower alkyl, lower alkoxy, fluoro substituted lower alkoxy, lower alkylthio, and fluoro substituted lower alkylthio, preferably $R^{27}$ and $R^{28}$ are both hydrogen.

In some embodiments of compounds of Formula Ia-Ih, further to any of the embodiments contemplated herein of compounds of Formula Ia-Ih, $X_1$ is CH. In some embodiments, $R^2$ and $R^3$ are hydrogen. In some embodiments, $R^1$ is —COOR$^8$, preferably —COOH. In some embodiments, $X_1$ is CH and $R^2$ and $R^3$ are hydrogen. In some embodiments, $X_1$ is CH and $R^1$ is —COOR$^8$, preferably —COOH. In some embodiments, $R^2$ and $R^3$ are hydrogen and $R^1$ is —COOR$^8$, preferably —COOH. In some embodiments, $X_1$ is CH. $R^2$ and $R^3$ are hydrogen and $R^1$ is —COOR$^8$, preferably —COOH.

In some embodiments of compounds of Formula Ia-Ih, further to any of the embodiments contemplated herein of compounds of Formula Ia-Ih, at least one of $R^4$ and $R^5$ is hydrogen. In some embodiments, $R^4$ is hydrogen. In some embodiments, $R^2$, $R^3$ and $R^4$ are hydrogen. In some embodiments, $R^4$ is hydrogen and $R^1$ is —COOR$^8$, preferably —COOH. In some embodiments, $R^2$, $R^3$ and $R^4$ are hydrogen and $R^1$ is —COOR$^8$, preferably —COOH. In some embodiments, $R^5$ is hydrogen. In some embodiments, $R^2$, $R^3$ and $R^5$ are hydrogen. In some embodiments, $R^5$ is hydrogen and $R^1$ is —COOR$^8$, preferably —COOH. In some embodiments, $R^2$, $R^3$ and $R^5$ are hydrogen and $R^1$ is —COOR$^8$, preferably —COOH.

In some embodiments of compounds of Formula Ia-Ih, further to any of the embodiments contemplated herein of compounds of Formula Ia-Ih, one of $X_2$ and $X_3$ is N and the other of $X_2$ and $X_3$ is CH. In some embodiments, $X_2$ is N and $X_3$ is CH. In some embodiments, $X_2$ is N, $X_3$ is CH, and $R^6$ is hydrogen. In some embodiments, $X_2$ is CH and $X_3$ is N. In some embodiments, $X_2$ is CH, $X_3$ is N and $R^6$ is hydrogen. In some embodiments, both $X_2$ and $X_3$ are CH. In some embodiments, both $X_2$ and $X_3$ are CH and $R^6$ is hydrogen. In some embodiments, $X_1$, $X_2$ and $X_3$ are CH and $R^6$ is hydrogen. In some embodiments, $X_1$, $X_2$ and $X_3$ are CH, $R^4$ is hydrogen and $R^1$ is —COOR$^8$, preferably —COOH. In some embodiments, $X_1$, $X_2$ and $X_3$, are CH, $R^2$, $R^3$, $R^4$ and $R^6$ are hydrogen and $R^1$ is —COOR$^8$, preferably —COOH. In some embodiments, $X_1$, $X_2$ and $X_3$ are CH, $R^5$ is hydrogen and $R^1$ is —COOR , preferably —COOH. In some embodiments, $X_1$, $X_2$ and $X_3$ are CH, $R^2$, $R^3$, $R^5$ and $R_6$ are hydrogen and $R^1$ is —COOR$^8$, preferably —COOH.

In some embodiments, compounds of Formula I have the following sub-generic structure Formula Ii:

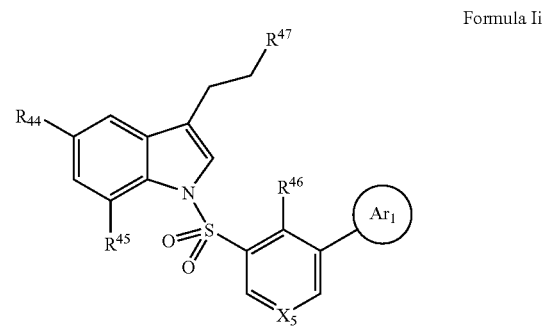

Formula Ii all salts, prodrugs, tautomers and isomers thereof,
wherein:
  $X_5$ is CH or N;
  $R^{44}$ is hydrogen, fluoro, chloro, or methoxy;
  $R^{45}$ is hydrogen, chloro, or methyl;
  $R^{46}$ is hydrogen or methyl;
  $R^{47}$ is selected from the group consisting of —C(O)OR$^{48}$, —C(O)NR$^{49}$R$^{50}$, and a carboxylic acid isostere;
  $R^{48}$ is selected from the group consisting of hydrogen, lower alkyl, phenyl, 5-7 membered monocyclic heteroaryl, 3-7 membered monocyclic cycloalkyl, and 5-7 membered monocylic heterocycloalkyl, wherein phenyl, monocyclic heteroaryl, monocyclic cycloalkyl and monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, —OH, —NH$_2$, lower alkoxy, fluoro substituted lower alkoxy, lower alkylthio and fluoro substituted lower alkylthio, provided, however, that when R$^{48}$ is lower alkyl, any substitution on the lower alkyl carbon bound to the O of OR$^{48}$ is fluoro;

R$^{49}$ and R$^{50}$ are independently selected from the group consisting of hydrogen, lower alkyl, phenyl, 5-7 membered monocyclic heteroaryl, 3-7 membered monocyclic cycloalkyl, and 5-7 membered monocylic heterocycloalkyl, wherein phenyl, monocyclic heteroaryl, monocyclic cycloalkyl and monocyclic heterocycloalkyl are optionally substituted with one or more substituents selected from the group consisting of halogen, —OH, —NH$_2$, lower alkyl fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, —OH, —NH$_2$, lower alkoxy, fluoro substituted lower alkoxy, lower alkylthio and fluoro substituted lower alkylthio, provided, however, that when R$^{49}$ and/or R$^{50}$ is lower alkyl, any substitution on the lower alkyl carbon bound to the N of NR$^{49}$R$^{50}$ is fluoro; or R$^{49}$ and R$^{50}$ together with the nitrogen to which they are attached form a 5-7 membered monocyclic heterocycloalkyl or a 5 or 7 membered nitrogen containing monocyclic heteroaryl, wherein the monocyclic heterocycloalkyl or monocyclic nitrogen containing heteroaryl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, and fluoro substituted lower alkylthio;

Ar$_1$ is selected from the group consisting of:

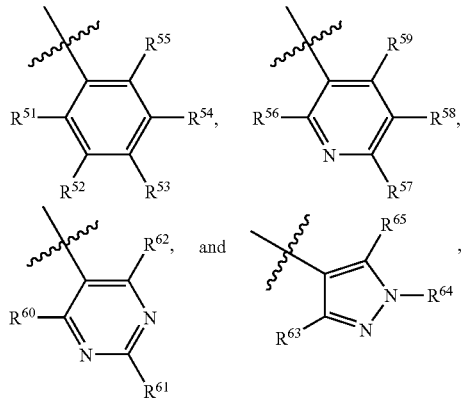

wherein

indicates the point of attachment of Ar$_1$ to the ring of Formula Ii;

R$^{51}$, R$^{52}$, R$^{53}$, R$^{54}$, R$^{55}$, R$^{58}$ and R$^{59}$ are independently selected from the group consisting of hydrogen, fluoro, chloro, C$_{1-3}$ alkyl fluoro substituted C$_{1-3}$ alkyl, C$_{1-3}$ alkoxy, fluoro substituted C$_{1-3}$ alkoxy, and benzyloxy;

R$^{56}$, R$^{57}$, R$^{63}$ and R$^{65}$ are independently selected from the group consisting of hydrogen, fluoro, C$_{1-3}$ alkyl fluoro substituted C$_{1-3}$ alkyl, C$_{1-3}$ alkoxy, fluoro substituted C$_{1-3}$ alkoxy, and benzyloxy;

R$^{60}$, R$^{61}$ and R$^{62}$ are independently selected from the group consisting of hydrogen, C$_{1-3}$ alkyl, fluoro substituted C$_{1-3}$ alkyl, C$_{1-3}$ alkoxy, fluoro substituted C$_{1-3}$ alkoxy, and benzyloxy; and R$^{64}$ is lower alkyl or fluoro substituted lower alkyl.

In some embodiments of compounds of Formula Ii, Ar$_1$ is

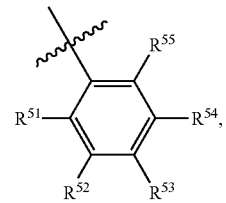

and R$^{51}$, R$^{52}$, R$^{53}$, R$^{54}$, and R$^{55}$ are independently selected from the group consisting of hydrogen, fluoro, chloro, methyl, trifluoromethyl, methoxy, trifluoromethoxy, ethoxy, and benzyloxy. In some embodiments, three of R$^{51}$, R$^{52}$, R$^{53}$, R$^{54}$, and R$^{55}$ are hydrogen and the others of R$^{51}$, R$^{52}$, R$^{53}$, R$^{54}$, and R$^{55}$ are independently selected from the group consisting of hydrogen, fluoro, chloro, methyl, trifluoromethyl, methoxy, trifluoromethoxy, ethoxy, and benzyloxy.

In some embodiments of compounds of Formula Ii, Ar$_1$ is

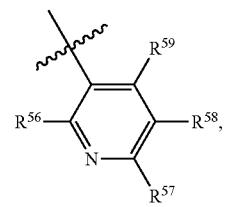

R$^{56}$, and R$^{57}$ are independently selected from the group consisting of hydrogen, fluoro, methyl, trifluoromethyl, methoxy, trifluoromethoxy, ethoxy, and benzyloxy, and R$^{58}$ and R$^{59}$ are independently selected from the group consisting of hydrogen, fluoro, chloro, methyl, trifluoromethyl, methoxy, trifluoromethoxy, ethoxy, and benzyloxy. In some embodiments R$^{56}$, R$^{57}$, R$^{58}$, and R$^{59}$ are independently selected from the group consisting of hydrogen and methoxy.

In some embodiments of compounds of Formula Ii, Ar₁ is

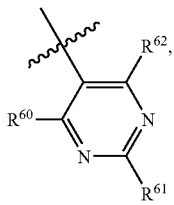

and $R^{60}$, $R^{61}$, and $R^{62}$ are independently selected from the group consisting of hydrogen, methyl, trifluoromethyl, methoxy, trifluoromethoxy, ethoxy, and benzyloxy. In some embodiments $R^{60}$, $R^{61}$, and $R^{62}$ are independently selected from the group consisting of hydrogen and methoxy.

In some embodiments of compounds of Formula Ii, Ar₁ is

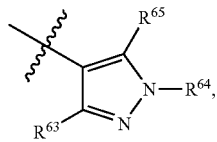

$R^{63}$, and $R^{65}$ are independently selected from the group consisting of hydrogen, fluoro, methyl, trifluoromethyl, methoxy, trifluoromethoxy, ethoxy, and benzyloxy, and $R^{64}$ is lower alkyl. In some embodiments, $R^{63}$ and $R^{65}$ are hydrogen and $R^{64}$ is lower alkyl.

In some embodiments of compounds of Formula Ii, further to any of the above embodiments of Formula Ii, at least one of $R^{44}$ and $R^{45}$ is hydrogen. In one embodiment, $R^{44}$ is hydrogen, fluoro, chloro or methoxy and $R^{45}$ is hydrogen. In one embodiment, $R^{44}$ is hydrogen and $R^{45}$ is hydrogen, chloro or methyl.

In one embodiment of compounds of Formula I, the compound is selected from the group consisting of:
3-[5-Chloro-1-(4'-trifluoromethyl-biphenyl-3-sulfonyl)-1H-indol-3-yl]-propionic acid methyl ester (P-0001),
3-[5-Chloro-1-(4'-trifluoromethyl-biphenyl-3-sulfonyl)-1H-indol-3-yl]-propionic acid (P-0002),
3-[5-Chloro-1-(3'-chloro-biphenyl-3-sulfonyl)-1H-indol-3-yl]-propionic acid (P-0003),
3-[5-Chloro-1-(4'-chloro-biphenyl-3-sulfonyl)-1H-indol-3-yl]-propionic acid (P-0004),
3-[5-Chloro-1-(4'-methoxy-biphenyl-3-sulfonyl)-1H-indol-3-yl]-propionic acid (P-0005),
3-[5-Chloro-1-(4'-fluoro-biphenyl-3-sulfonyl)-1H-indol-3-yl]-propionic acid (P-0006),
3-[5-Chloro-1-(2',4'-difluoro-biphenyl-3-sulfonyl)-1H-indol-3-yl]-propionic acid (P-0007),
3-[5-Chloro-1-(3'-chloro-4'-fluoro-biphenyl-3-sulfonyl)-1H-indol-3-yl]-propionic acid (P-0008),
3-[5-Chloro-1-(4'-ethoxy-biphenyl-3-sulfonyl)-1H-indol-3-yl]-propionic acid (P-0009),
3-[5-Chloro-1-(3'-fluoro-biphenyl-3-sulfonyl)-1H-indol-3-yl]-propionic acid (P-0010),
3-[5-Chloro-1-(2'-fluoro-biphenyl-3-sulfonyl)-1H-indol-3-yl]-propionic acid (P-0011),
3-[5-Chloro-1-(3'-trifluoromethoxy-biphenyl-3-sulfonyl)-1H-indol-3-yl]-propionic acid (P-0012),
3-[5-Chloro-1-(4'-trifluoromethoxy-biphenyl-3-sulfonyl)-1H-indol-3-yl]-propionic acid (P-0013),
3-[5-Chloro-1-(3'-trifluoromethyl-biphenyl-3-sulfonyl)-1H-indol-3-yl]-propionic acid (P-0014),
3-[1-(4'-Benzyloxy-2'-fluoro-biphenyl-3-sulfonyl)-5-chloro-1H-indol-3-yl]-propionic acid (P-0015),
3-[5-Chloro-1-(3'-fluoro-4'-methyl-biphenyl-3-sulfonyl)-1H-indol-3-yl]-propionic acid (P-0017),
3-[5-Chloro-1-(3'-fluoro-4'-methoxy-biphenyl-3-sulfonyl)-1H-indol-3-yl]-propionic acid (P-0018),
3-[5-Chloro-1-(2'-fluoro-4'-trifluoromethyl-biphenyl-3-sulfonyl)-1H-indol-3-yl]-propionic acid (P-0021),
3-[5-Chloro-1-(2'-fluoro-4'-methoxy-biphenyl-3-sulfonyl)-1H-indol-3-yl]-propionic acid (P-0024),
3-[5-Chloro-1-(4'-chloro-2'-fluoro-biphenyl-3-sulfonyl)-1H-indol-3-yl]-propionic acid (P-0025),
3-[-(Biphenyl-3-sulfonyl)-5-chloro-1H-indol-3-yl]-propionic acid (P-0124),
3-[5-Chloro-1-(2',4'-dichloro-biphenyl-3-sulfonyl)-1H-indol-3-yl]-propionic acid (P-0125),
3-[5-Chloro-1-(4'-fluoro-2'-methyl-biphenyl-3-sulfonyl)-1H-indol-3-yl]-propionic acid (P-0126),
3-[5-Chloro-1-(2',3'-dichloro-biphenyl-3-sulfonyl)-1H-indol-3-yl]-propionic acid (P-0127),
3-[5-Chloro-1-(2',3'-difluoro-biphenyl-3-sulfonyl)-1H-indol-3-yl]-propionic acid (P-0128),
3-[5-Chloro-1-(2'-chloro-4'-trifluoromethyl-biphenyl-3-sulfonyl)-1H-indol-3-yl]-propionic acid (P-0129),
3-[5-Chloro-1-(4'-chloro-2'-methyl-biphenyl1-3-sulfonyl)-1H-indol-3-yl]-propionic acid (P-0130),
3-[5-Chloro-1-(2'-chloro-4'-ethoxy-biphenyl-3-sulfonyl)-1H-indol-3-yl]-propionic acid (P-0131),
3-[5-Chloro-1-(2'-chloro-3'-fluoro-biphenyl-3-sulfonyl)-1H-indol-3-yl]-propionic acid (P-0132),
3-[5-Chloro-1-(2'-chloro-4'-fluoro-biphenyl-3-sulfonyl)-1H-indol-3-yl]-propionic acid (P-0133),
3-[5-Chloro-1-(4'-ethoxy-2'-methyl-biphenyl-3-sulfonyl)-1H-indol-3-yl]-propionic acid (P-0134), and
all salts, prodrugs, tautomers, and isomers thereof.

In one embodiment of compounds of Formula I, the compound is selected from the group consisting of:
3-[1-(3'-Chloro-biphenyl-3-sulfonyl)-5-fluoro-1H-indol-3-yl]-propionic acid (P-0026),
3-[1-(4'-Chloro-biphenyl-3-sulfonyl)-5-fluoro-1H-indol-3-yl]-propionic acid (P-0027),
3-[5-Fluoro-1-(4'-methoxy-biphenyl-3-sulfonyl)-1H-indol-3-yl]-propionic acid (P-0028),
3-[5-Fluoro-1-(4'-fluoro-biphenyl-3-sulfonyl)-1H-indol-3-yl]-propionic acid (P-0029),
3-[1-(3'-Chloro-4'-fluoro-biphenyl-3-sulfonyl)-5-fluoro-1H-indol-3-yl]-propionic acid (P-0030),
3-[5-Fluoro-1-(3'-fluoro-biphenyl-3-sulfonyl)-1H-indol-3-yl]-propionic acid (P-0031),
3-[5-Fluoro-1-(2'-fluoro-biphenyl-3-sulfonyl)-1-indol-3-yl]-propionic acid (P-0032),
3-[5-Fluoro-1-(3'-trifluoromethoxy-biphenyl-3-sulfonyl)-1H-indol-3-yl]-propionic acid (P-0033),
3-[5-Fluoro- -(4'-trifluoromethoxy-biphenyl-3-sulfonyl)-1H-indol-3-yl]-propionic acid (P-0034),
3-[5-Fluoro-1-(4'-trifluoromethyl-biphenyl-3-sulfonyl)-1H-indol-3-yl]-propionic acid (P-0035),
3-[1-(4'-Benzyloxy-2'-fluoro-biphenyl-3-sulfonyl)-5-fluoro-1H-indol-3-yl]-propionic acid (P-0036),
3-[5-Fluoro-1-(3'-fluoro-4'-methoxy-biphenyl-3-sulfonyl)-1H-indol-3-yl]-propionic acid (P-0038),
3-[5-Fluoro-1-(2'-fluoro-4'-methoxy-biphenyl-3-sulfonyl)-1H-indol-3-yl]-propionic acid (P-0043),
3-[1-(4'-Chloro-2'-fluoro-biphenyl-3-sulfonyl)-5-fluoro-1H-indol-3-yl]-propionic acid (P-0044), 3-[1-(2',4'-Difluoro-biphenyl-3-sulfonyl)-5-fluoro-1H-indol-3-yl]-propionic acid (P-0068),
3-[5-Fluoro-1-(2'-fluoro-4'-trifluoromethyl-biphenyl-3-sulfonyl)-1H-indol-3-yl]-propionic acid (P-0069),
3-[1-(Biphenyl-3-sulfonyl)-5-fluoro-1H-indol-3-yl]-propionic acid (P-0102),
3-[1-(2',4'-Dichloro-biphenyl-3-sulfonyl)-5-fluoro-1H-indol-3-yl]-propionic acid (P-0103),
3-[5-Fluoro-1-(4'-fluoro-2'-methyl-biphenyl-3-sulfonyl)-1H-indol-3-yl]-propionic acid (P-0104),
3-[1-(2',3'-Dichloro-biphenyl-3-sulfonyl)-5-fluoro-1H-indol-3-yl]-propionic acid (P-0105),
3-[1-(2',3'-Difluoro-biphenyl-3-sulfonyl)-5-fluoro-1H-indol-3-yl]-propionic acid (P-0106),
3-[1-(2'-Chloro-4'-trifluoromethyl-biphenyl-3-sulfonyl)-5-fluoro-1H-indol-3-yl]-propionic acid (P-0107),
3-[1-(4'-Chloro-2'-methyl-biphenyl-3-sulfonyl)-5-fluoro-1H-indol-3-yl]-propionic acid (P-0108),
3-[1-(2'-Chloro-4'-ethoxy-biphenyl-3-sulfonyl)-5-fluoro-1H-indol-3-yl]-propionic acid (P-0109),
3-[1-(2'-Chloro-3'-fluoro-biphenyl-3-sulfonyl)-5-fluoro-1H-indol-3-yl]-propionic acid (P-0110),
3-[1-(2'-Chloro-4'-fluoro-biphenyl-3-sulfonyl)-5-fluoro-1H-indol-3-yl]-propionic acid (P-0111),
3-[1-(4'-Ethoxy-2'-methyl-biphenyl-3-sulfonyl)-5-fluoro-1H-indol-3-yl]-propionic acid (P-0112), and
all salts, prodrugs, tautomers, and isomers thereof.

In one embodiment of compounds of Formula I, the compound is selected from the group consisting of:
3-[1-(3'-Chloro-biphenyl-3-sulfonyl)-5-methoxy-1H-indol-3-yl]-propionic acid (P-0045),
3-[1-(4'-Chloro-biphenyl-3-sulfonyl)-5-methoxy-1H-indol-3-yl]-propionic acid (P-0046),
3-[5-Methoxy-1-(4'-methoxy-biphenyl-3-sulfonyl)-1H-indol-3-yl]-propionic acid (P-0047),
3-[1-(4'-Fluoro-biphenyl-3-sulfonyl)-5-methoxy-1H-indol-3-yl]-propionic acid (P-0048),
3-[1-(2',4'-Difluoro-biphenyl-3-sulfonyl)-5-methoxy-1H-indol-3-yl]-propionic acid (P-0049),
3-[1-(3'-Chloro-4'-fluoro-biphenyl-3-sulfonyl)-5-methoxy-1H-indol-3-yl]-propionic acid (P-0050),
3-[1-(4'-Ethoxy-biphenyl-3-sulfonyl)-5-methoxy-1H-indol-3-yl]-propionic acid (P-0051),
3-[1-(3'-Fluoro-biphenyl-3-sulfonyl)-5-methoxy-1H-indol-3-yl]-propionic acid (P-0052),
3-[1-(2'-Fluoro-biphenyl-3-sulfonyl)-5-methoxy-1H-indol-3-yl]-propionic acid (P-0053),
3-[5-Methoxy-1-(3'-trifluoromethoxy-biphenyl-3-sulfonyl)-1H-indol-3-yl]-propionic acid (P-0054),
3-[5-Methoxy-1-(4'-trifluoromethoxy-biphenyl-3-sulfonyl)-1H-indol-3-yl]-propionic acid (P-0055),
3-[5-Methoxy-1-(3'-trifluoromethyl-biphenyl-3-sulfonyl)-1H-indol-3-yl]-propionic acid (P-0056),
3-[1-(4'-Benzyloxy-2'-fluoro-biphenyl-3-sulfonyl)-5-methoxy-1H-indol-3-yl]-propionic acid (P-0057),
3-[1-(3'-Fluoro-4'-methyl-biphenyl-3-sulfonyl)-5-methoxy-1H-indol-3-yl]-propionic acid (P-0059),
3-[1-(3'-Fluoro-4'-methoxy-biphenyl-3-sulfonyl)-5-methoxy-1H-indol-3-yl]-propionic acid (P-0060),
3-[1-(2'-Fluoro-4'-trifluoromethyl-biphenyl-3-sulfonyl)-5-methoxy-1H-indol-3-yl]-propionic acid (P-0063),
3-[1-(2'-Fluoro4'-methoxy-biphenyl-3-sulfonyl)-5-methoxy-1H-indol-3-yl]-propionic acid (P-0066),
3-[1-(4'-Chloro-2'-fluoro-biphenyl-3-sulfonyl)-5-methoxy-1H-indol-3-yl]-propionic acid (P-0067),
3-[1-(Biphenyl-3-sulfonyl)-5-methoxy-1H-indol-3-yl]-propionic acid (P-0113),
3-[1-(2',4'-Dichloro-biphenyl-3-sulfonyl)-5-methoxy-1H-indol-3-yl]-propionic acid (P-0114),
3-[1-(4'-Fluoro-2'-methyl-biphenyl-3-sulfonyl)-5-methoxy-1H-indol-3-yl]-propionic acid (P-0115),
3-[1-(2',3'-Dichloro-biphenyl-3-sulfonyl)-5-methoxy-1H-indol-3-yl]-propionic acid (P-0116),
3-[1-(2',3'-Difluoro-biphenyl-3-sulfonyl)-5-methoxy-1H-indol-3-yl]-propionic acid (P-0117),
3-[1-(2'-Chloro-4'-trifluoromethyl-biphenyl-3-sulfonyl)-5-methoxy-1H-indol-3-yl]-propionic acid (P-0118),
3-[1-(4'-Chloro-2'-methyl-biphenyl-3-sulfonyl)-5-methoxy-1H-indol-3-yl]-propionic acid (P-0119),
3-[1-(2'-Chloro-4'-ethoxy-biphenyl-3-sulfonyl)-5-methoxy-1H-indol-3-yl]-propionic acid (P-0120),
3-[1-(2'-Chloro-3'-fluoro-biphenyl-3-sulfonyl)-5-methoxy-1H-indol-3-yl]-propionic acid (P-0121),
3-[1-(2'-Chloro-4'-fluoro-biphenyl-3-sulfonyl)-5-methoxy-1H-indol-3-yl]-propionic acid (P-0122),
3-[1-(4'-Ethoxy-2'-methyl-biphenyl-3-sulfonyl)-5-methoxy-1H-indol-3-yl]-propionic acid (P-0123), and
all salts, prodrugs, tautomers, and isomers thereof.

In one embodiment of compounds of Formula I, the compound is selected from the group consisting of:
3-[1-(3'-Chloro-biphenyl-3-sulfonyl)-1H-indol-3-yl]-propionic acid (P-0070),
3-[1-(4'-Chloro-biphenyl-3-sulfonyl)-1H-indol-3-yl]-propionic acid (P-0071),
3-[1-(4'-Methoxy-biphenyl-3-sulfonyl)-1H-indol-3-yl]-propionic acid (P-0072),
3-[1-(4'-Fluoro-biphenyl-3-sulfonyl)-1H-indol-3-yl]-propionic acid (P-0073),
3-[1-(2',4'-Difluoro-biphenyl-3-sulfonyl)-1H-indol-3-yl]-propionic acid (P-0074),
3-[1-(3'-Chloro-4'-fluoro-biphenyl-3-sulfonyl)-1H-indol-3-yl]-propionic acid (P-0075),
3-[1-(4'-Ethoxy-biphenyl-3-sulfonyl)-1H-indol-3-yl]-propionic acid (P-0076),
3-[1-(3'-Fluoro-biphenyl-3-sulfonyl)-1H-indol-3-yl]-propionic acid (P-0077),
3-[1-(2'-Fluoro-biphenyl-3-sulfonyl)-1H-indol-3-yl]-propionic acid (P-0078),
3-[1-(3'-Trifluoromethoxy-biphenyl-3-sulfonyl)-1H-indol-3-yl]-propionic acid (P-0079),
3-[1-(4'-Trifluoromethoxy-biphenyl-3-sulfonyl)-1H-indol-3-yl]-propionic acid (P-0080),
3-[1-(3'-Trifluoromethyl-biphenyl-3-sulfonyl)-1H-indol-3-yl]-propionic acid (P-0081),
3-[1-(4'-Benzyloxy-2'-fluoro-biphenyl-3-sulfonyl)-1H-indol-3-yl]-propionic acid (P-0082),
3-[1-(3'-Fluoro4'-methyl-biphenyl-3-sulfonyl)-1H-indol-3-yl]-propionic acid (P-0084),
3-[1-(3'-Fluoro-4'-methoxy-biphenyl-3-sulfonyl)-1H-indol-3-yl]-propionic acid (P-0085),
3-[1-(2'-Fluoro-4'-trifluoromethyl-biphenyl-3-sulfonyl)-1H-indol-3-yl]-propionic acid (P-0087),
3-[1-(2'-Fluoro4'-methoxy-biphenyl-3-sulfonyl)-1H-indol-3-yl]-propionic acid (P-0088),
3-[1-(4'-Chloro-2'-fluoro-biphenyl-3-sulfonyl)-1H-indol-3-yl]-propionic acid (P-0089),
3-[1-(Biphenyl-3-sulfonyl)-1H-indol-3-yl]-propionic acid (P-0092),
3-[1-(2',4'-Dichloro-biphenyl-3-sulfonyl)-1H-indol-3-yl]-propionic acid (P-0093),
3-[1-(4'-Fluoro-2'-methyl-biphenyl-3-sulfonyl)-1H-indol-3-yl]-propionic acid (P-0094),
3-[1-(2',3'-Dichloro-biphenyl-3-sulfonyl)-1H-indol-3-yl]-propionic acid (P-0095), 3-[1-(2',3'-Difluoro-biphenyl-3-sulfonyl)-1H-indol-3-yl]-propionic acid (P-0096),
3-[1-(4'-Chloro-2'-methyl-biphenyl-3-sulfonyl)-1H-indol-3-yl]-propionic acid (P-0097),
3-[1-(2'-Chloro-4'-ethoxy-biphenyl-3-sulfonyl)-1H-indol-3-yl]-propionic acid (P-0098),
3-[1-(2'-Chloro-3'-fluoro-biphenyl-3-sulfonyl)-1H-indol-3-yl]-propionic acid (P-0099),
3-[1-(2'-Chloro-4'-fluoro-biphenyl-3-sulfonyl)-1H-indol-3-yl]-propionic acid (P-0100),
3-[1-(4'-Ethoxy-2'-methyl-biphenyl-3-sulfonyl)-1H-indol-3-yl]-propionic acid (P-0101),
all salts, prodrugs, tautomers, and isomers thereof.

In one embodiment of compounds of Formula I, the compound is selected from the group consisting of:
3-{5-Chloro-1-[3-(6-methoxy-pyridin-3-yl)-benzenesulfonyl]-1H-indol-3-yl}-propionic acid (P-0016),
3-{5-Chloro-1-[3-(2-methoxy-pyrimidin-5-yl)-benzenesulfonyl]-1H-indol-3-yl}-propionic acid (P-0019),
3-{5-Chloro-1-[3-(2,4-dimethoxy-pyrimidin-5-yl)-benzenesulfonyl]-1H-indol-3-yl}-propionic acid (P-0020),
3-{5-Fluoro-1-[3-(6-methoxy-pyridin-3-yl)-benzenesulfonyl]-1H-indol-3-yl}-propionic acid (P-0037),
3-{5-Fluoro-1-[3-(2-methoxy-pyrimidin-5-yl)-benzenesulfonyl]-1H-indol-3-yl}-propionic acid (P-0039),
3-{1-[3-(2,4-Dimethoxy-pyrimidin-5-yl)-benzenesulfonyl]-5-1H-indol-3-yl}-propionic acid (P-0040),
3-{5-Methoxy-1-[3-(6-methoxy-pyridin-3-yl)-benzenesulfonyl]-1H-indol-3-yl}-propionic acid (P-0058),
3-{5-Methoxy-1-[3-(2-methoxy-pyrimidin-5-yl)-benzenesulfonyl]-1H-indol-3-yl}-propionic acid (P-0061),
3-{1-[3-(2,4-Dimethoxy-pyrimidin-5-yl)-benzenesulfonyl]-5-methoxy-1H-indol-3-yl}-propionic acid (P-0062),
3-{1-[3-(6-Methoxy-pyridin-3-yl)-benzenesulfonyl]-1H-indol-3-yl}-propionic acid (P-0083),
3-{1-[3-(2,4-Dimethoxy-pyrimidin-5-yl)-benzenesulfonyl]-1H-indol-3-yl}-propionic acid (P-0086), and
all salts, prodrugs, tautomers, and isomers thereof.

In one embodiment of compounds of Formula I, the compound is selected from the group consisting of:
3-[5-Fluoro-1-(2-methyl-4'-trifluoromethoxy-biphenyl-3-sulfonyl)-1H-indol-3-yl]-propionic acid (P-0135),
3-[5-Fluoro-1-(2-methyl-4'-trifluoromethoxy-biphenyl-3-sulfonyl)-1H-indol-3-yl]-propionic acid methyl ester (P-0136),
3-[5-Fluoro-1-(2-methyl-4'-trifluoromethyl-biphenyl-3-sulfonyl)-1H-indol-3-yl]-propionic acid (P-0137),
3-[1-(4'-Chloro-2-methyl-biphenyl-3-sulfonyl)-5-fluoro-1H-indol-3-yl]-propionic acid (P-0138),
3-[1-(2-Methyl-4'-trifluoromethyl-biphenyl-3-sulfonyl)-1H-indol-3-yl]-propionic acid (P-0142),
3-[1-(2-Methyl-4'-trifluoromethoxy-biphenyl-3-sulfonyl)-1H-indol-3-yl]-propionic acid (P-0143),
3-[5-Chloro-1-(2-methyl-4'-trifluoromethyl-biphenyl-3-sulfonyl)-1H-indol-3-yl]-propionic acid (P-0146),
3-[5-Chloro-1-(2-methyl-4'-trifluoromethoxy-biphenyl-3-sulfonyl)-1H-indol-3-yl]-propionic acid (P-0147), and
all salts, prodrugs, tautomers, and isomers thereof.

In one embodiment of compounds of Formula I, the compound is selected from the group consisting of:
3-{5-Chloro-1-[5-(4-trifluoromethoxy-phenyl)-pyridine-3-sulfonyl]-1H-indol-3-yl}-propionic acid (P-0148),
3-{5-Chloro-1-[5-(4-trifluoromethyl-phenyl)-pyridine-3-sulfonyl]-1H-indol-3-yl}-propionic acid (P-0149),
3-{5-Fluoro-1-[5-(4-trifluoromethoxy-phenyl)-pyridine-3-sulfonyl]-1H-indol-3-yl}-propionic acid methyl ester (P-0150),
3-{5-Fluoro-1-[5-(4-trifluoromethyl-phenyl)-pyridine-3-sulfonyl]-1H-indol-3-yl}-propionic acid methyl ester (P-0151),
3-{1-[5-(4-Chloro-phenyl)-pyridine-3-sulfonyl]-5-fluoro-1H-indol-3-yl}-propionic acid methyl ester (P-0152),
3-{5-Fluoro-1-[5-(2-fluoro-4-trifluoromethyl-phenyl)-pyridine-3-sulfonyl]-1H-indol-3-yl}-propionic acid methyl ester (P-0153),
3-{5-Fluoro-1-[5-(4-trifluoromethoxy-phenyl)-pyridine-3-sulfonyl]-1H-indol-3-yl}-propionic acid (P-0154),
3-{5-Fluoro-1-[5-(4-trifluoromethyl-phenyl)-pyridine-3-sulfonyl]-1H-indol-3-yl}-propionic acid (P-0155),
3-{5-Chloro-1-[5-(4-ethoxy-2-methyl-phenyl)-pyridine-3-sulfonyl]-1H-indol-3-yl}-propionic acid (P-0156),
3-{5-Chloro-1-[5-(2-chloro-4-ethoxy-phenyl)-pyridine-3-sulfonyl]-1H-indol-3-yl}propionic acid (P-0157),
3-{5-Chloro-1-[5-(2-fluoro-4-trifluoromethyl-phenyl)-pyridine-3-sulfonyl]-1H-indol-3-yl}-propionic acid (P-0158),
3-{5-Chloro-1-[5-(2-chloro-4-trifluoromethyl-phenyl)-pyridine-3-sulfonyl]-1H-indol-3-yl}-propionic acid (P-0159),
3-{5-Chloro-1-[5-(2-methyl-4-trifluoromethyl-phenyl)-pyridine-3-sulfonyl]-1H-indol-3-yl}-propionic acid (P-0160),
3-{1-[5-(4-Ethoxy-2-methyl-phenyl)-pyridine-3-sulfonyl]-5-fluoro-1H-indol-3-yl}-propionic acid (P-0161),
3-{1-[5-(2-Chloro-4-trifluoromethyl-phenyl)-pyridine-3-sulfonyl]-5-fluoro-1H-indol-3yl}-propionic acid (P-0162),
3-{5-Fluoro-1-[5-(2-methyl-4-trifluoromethyl-phenyl)-pyridine-3-sulfonyl]-1H-indol-3-yl}-propionic acid (P-0163),
3-{5-Fluoro-1-[5-(2-fluoro-4-trifluoromethyl-phenyl)-pyridine-3-sulfonyl]-1H-indol-3-yl}-propionic acid (P-0164),
3-{1-[5-(3-Chloro-4-fluoro-phenyl)-pyridine-3-sulfonyl]-5-methoxy-1H-indol-3-yl}-propionic acid (P-0165), and
all salts, prodrugs, tautomers, and isomers thereof.

In one embodiment of compounds of Formula I, the compound is selected from the group consisting of:
3-[7-Methyl-1-(4'-trifluoromethoxy-biphenyl-3-sulfonyl)-1H-indol-3-yl]-propionic acid (P-0139),
3-[7-Methyl-1-(4'-trifluoromethyl-biphenyl-3-sulfonyl)-1H-indol-3-yl]-propionic acid (P-0140),
3-[7-Chloro-1-(2'-fluoro-4'-trifluoromethyl-biphenyl-3-sulfonyl)-1H-indol-3-yl]-propionic acid (P-0141),
3-[7-Chloro-1-(4'-trifluoromethyl-biphenyl-3-sulfonyl)-1H-indol-3-yl]-propionic acid (P-0144),
3-[7-Chloro-1-(4'-trifluoromethoxy-biphenyl-3-sulfonyl)-1H-indol-3-yl]-propionic acid (P-0145), and
all salts, prodrugs, tautomers, and isomers thereof.

In one embodiment of compounds of Formula I, the compound is selected from the group consisting of:
3-(5-Chloro-1-{3-[1-(3-methyl-butyl)-1H-pyrazol-4-yl]-benzenesulfonyl}-1H-indol-3yl)-propionic acid (P-0022),
3-{5-Chloro-1-[3-(1-isobutyl-1H-pyrazol-4-yl)-benzenesulfonyl]-1H-indol-3-yl}-propionic acid (P-0023),
3-(5-Fluoro-1-{3-[1-(3-methyl-butyl)-1H-pyrazol-4-yl]-benzenesulfonyl}-1H-indol-3-yl)-propionic acid (P-0041),
3-{5-Fluoro-1-[3-(1-isobutyl-1H-pyrazol-4-yl)-benzenesulfonyl]-1H-indol-3-yl}-propionic acid (P-0042),
3-(5-Methoxy-1-{3-[1-(3-methyl-butyl)-1H-pyrazol-4-yl]-benzenesulfonyl}-1H-indol-3-yl)-propionic acid (P-0064),
3-{1-[3-(1-Isobutyl-1H-pyrazol-4-yl)-benzenesulfonyl]-5-methoxy-1H-indol-3-yl}-propionic acid (P-0065),
3-(1-{3-[1-(3-Methyl-butyl)-1H-pyrazol-4-yl]-benzenesulfonyl}-1H-indol-3-yl)-propionic acid (P-0090), 3-{1-[3-(1-Isobutyl-1H-pyrazol-4-yl)-benzenesulfonyl]-1H-indol-3-yl}-propionic acid (P-0091), and all salts, prodrugs, tautomers, and isomers thereof.

In all of the above embodiments, it is understood that selected substituents, including any combinations thereof, are chemically feasible and provide a stable compound. In some embodiments of the above compounds, compounds are excluded where N (except where N is a heteroaryl ring atom), O, or S is bound to a carbon that is also bound to N (except where N is a heteroaryl ring atom), O, or S, except where the carbon forms a double bond with one of the heteroatoms, such as in an amide, carboxylic acid, and the like; or where N (except where N is a heteroaryl ring atom), O, C(S), C(O), or $S(O)_n$ (n is 0-2) is bound to an alkene carbon of an alkenyl group or bound to an alkyne carbon of an alkynyl group; accordingly, in some embodiments compounds that include linkages such as the following are excluded from the present invention: —NR—$CH_2$—NR—, —O—$CH_2$—NR—, —S—$CH_2$—NR—, —NR—$CH_2$—O—, —O—$CH_2$—O—, —S—$CH_2$—O—, —NR—$CH_2$—S—, —O—$CH_2$—S—, —S—$CH_2$—S—, —NR—CH=CH—, —CH=CH—NR—, —NR—C≡C—, —C≡C—NR—, —O—CH=CH—, —CH=CH—O—, —O—C≡C—, —C≡C—O—, —$S(O)_{0-2}$—CH=CH—, —CH=CH—$S(O)_{0-2}$—, —$S(O)_{0-2}$—C≡C—, —C≡C—$S(O)_{0-2}$—, —C(O)—CH=CH—, —CH=CH—C(O)—, —C≡C—C(O)—, —C(O)—C≡C—, —C(S)—CH=CH—, —CH=CH—C(S)—, —C≡C—C(S)—, or —C(S)—C≡C—.

Reference to compounds of Formula I herein includes specific reference to sub-groups and species of compounds of Formula I described herein (e.g., including Formulae Ia-Ii, and all embodiments as described above) unless indicated to the contrary. In specifying a compound or compounds of Formula I, unless clearly indicated to the contrary, specification of such compound(s) includes pharmaceutically acceptable salts of the compound(s), pharmaceutically acceptable formulations of the compound(s), prodrug(s), and all stereoisomers thereof.

Another aspect of this invention provides compositions that include a therapeutically effective amount of a compound of Formula I and at least one pharmaceutically acceptable carrier, excipient, and/or diluent. The composition can include a plurality of different pharmacologically active compounds, including one or more compounds of Formula I.

In another aspect, compounds of Formula I can be used in the preparation of a medicament for the treatment of a PPAR-mediated disease or condition or a disease or condition in which modulation of a PPAR provides a therapeutic benefit. In a further aspect, the disease or condition is selected from the group consisting of weight disorders (e.g., including, but not limited to, obesity, overweight condition, bulimia, and anorexia nervosa), lipid disorders (e.g., including, but not limited to, hyperlipidemia, dyslipidemia (including associated diabetic dyslipidemia and mixed dyslipidemia), hypoalphalipoproteinemia, hyperriglyceridemia, hypercholesterolemia, and low HDL (high density lipoprotein)), metabolic disorders (e.g., including, but not limited to, Metabolic Syndrome, Type II diabetes mellitus, Type I diabetes, hyperinsulinemia, impaired glucose tolerance, insulin resistance, diabetic complication (e.g., including, but not limited to, neuropathy, nephropathy, retinopathy, diabetic foot ulcer, bladder dysfunction, bowel dysfunction, diaphragmatic dysfunction and cataracts)), cardiovascular disease (e.g., including, but not limited to, hypertension, coronary heart disease, heart failure, congestive heart failure, atherosclerosis, arteriosclerosis, stroke, cerebrovascular disease, myocardial infarction, and peripheral vascular disease), inflammatory diseases (e.g., including, but not limited to, autoimmune diseases (e.g., including, but not limited to, vitiligo, uveitis, optic neuritis, pemphigus foliaceus, pemphigoid, inclusion body myositis, polymyositis, dermatomyositis, scleroderma, Grave's disease, Hashimoto's disease, chronic graft versus host disease, ankylosing spondylitis, rheumatoid arthritis, inflammatory bowel disease (e.g. ulcerative colitis, Crohn's disease), systemic lupus erythematosis, Sjogren's Syndrome, and multiple sclerosis), diseases involving airway inflammation (e.g., including, but not limited to, asthma and chronic obstructive pulmonary disease), inflammation in other organs (e.g., including, but not limited to, polycystic kidney disease (PKD), polycystic ovary syndrome, pancreatitis, nephritis, and hepatitis), otitis, stomatitis, sinusitis, arteritis, temporal arteritis, giant cell arteritis, and polymyalgia rheumatica), skin disorders (e.g., including, but not limited to, epithelial hyperproliferative diseases (e.g., including, but not limited to, eczema and psoriasis), dermatitis (e.g., including, but not limited to, atopic dermatitis, contact dermatitis, allergic dermatitis and chronic dermatitis), and impaired wound healing)), neurodegenerative disorders (e.g., including, but not limited to, Alzheimer's disease, Parkinson's disease, amyotrophic lateral sclerosis, spinal cord injury, and demyelinating disease (e.g., including, but not limited to, acute disseminated encephalomvelitis and Guillain-Barre syndrome)), coagulation disorders (e.g., including, but not limited to, thrombosis), gastrointestinal disorders (e.g., including, but not limited to, gastroesophageal reflux, appendicitis, diverticulitis, gastrointestinal ulcers, ileus, motility disorders and infarction of the large or small intestine), genitourinary disorders (e.g., including, but not limited to, renal insufficiency, erectile dysfunction, urinary incontinence, and neurogenic bladder), ophthalmic disorders (e.g., including, but not limited to, ophthalmic inflammation, conjunctivitis, keratoconjunctivitis, corneal inflammation, dry eye syndrome, macular degeneration, and pathologic neovascularization), infections (e.g., including, but not limited to, lyme disease, HCV, HIV, and *Helicobacter pylori*) and inflammation associated with infections (e.g., including, but not limited to, encephalitis, meningitis), neuropathic or inflammatory pain, pain syndromes (e.g., including, but not limited to, chronic pain syndrome, fibromyalgia), infertility, and cancer (e.g., including, but not limited to, breast cancer and thyroid cancer).

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of weight disorders, lipid disorders, metabolic disorders and cardiovascular disease. In some embodiments, the disease or condition is selected from the group consisting of obesity, dyslipidemia, Metabolic Syndrome, Type II diabetes mellitus and atherosclerosis.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of inflammatory disease, neurodegenerative disorder, coagulation disorder, gastrointestinal disorder, genitourinary disorder, ophthalmic disorder, infection, inflammation associated with infection, neuropathic pain, inflammatory pain, pain syndromes, infertility and cancer. In some embodiments, the disease or condition is selected from the group consisting of inflammatory disease, neurodegenerative disorder, and cancer. In some embodiments, the disease or condition is selected from the group consisting of inflammatory bowel disease, multiple sclerosis, Alzheimer's disease, breast cancer and thyroid cancer.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of weight disorders, lipid disorders and cardiovascular disease.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of metabolic disorders, inflammatory diseases and neurodegenerative diseases.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of ophthalmic disorders, infections and inflammation associated with infections.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of neuropathic pain, inflammatory pain and pain syndromes.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of infertility and cancer.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of Metabolic Syndrome, Type II diabetes mellitus, Type I diabetes, hyperinsulinemia, impaired glucose tolerance, insulin resistance and a diabetic complication selected from the group consisting of neuropathy, nephropathy, retinopathy, diabetic foot ulcer, bladder dysfunction, bowel dysfunction, diaphragmatic dysfunction and cataracts, preferably the disease or condition is Metabolic Syndrome or Type II diabetes mellitus.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of obesity, overweight condition, bulimia, anorexia nervosa, hyperlipidemia, dyslipidemia, hypoalphalipoproteinemia, hypertriglyceridemia, hypercholesterolemia, and low HDL, preferably the disease or condition is obesity or dyslipidemia.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of Alzheimer's disease, Parkinson's disease, amyotrophic lateral sclerosis, spinal cord injury, and demyclinating disease, preferably the disease or condition is Alzheimer's disease.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of vitiligo, uveitis, optic neuritis, pemphigus foliaceus, pemphigoid, inclusion body myositis, polymyositis, dermatomyositis, scleroderma, Grave's disease, Hashimoto's disease, chronic graft versus host disease, ankylosing spondylitis, rheumatoid arthritis, inflammatory bowel disease systemic lupus erythematosis, Sjogren's Syndrome, and multiple sclerosis, asthma, chronic obstructive pulmonary disease, polycystic kidney disease, polycystic ovary syndrome, pancreatitis, nephritis, hepatitis, otitis, stomatitis, sinusitis, arteritis, temporal arteritis, giant cell arteritis, polymyalgia rheumatica, eczema, psoriasis, atopic dermatitis, contact dermatitis, allergic dermatitis, chronic dermatitis, and impaired wound healing, preferably the disease or condition is inflammatory bowel disease or multiple sclerosis.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of infertility and cancer, preferably the disease or condition is breast or thyroid cancer.

In some embodiments, compounds of Formula I can be used in the preparation of a medicament for the treatment of a PPAR-mediated disease or condition or a disease or condition in which modulation of a PPAR provides a therapeutic benefit, wherein the disease or condition is selected from the group consisting of hypertension, coronary heart disease, heart failure, congestive heart failure, atherosclerosis, arteriosclerosis, stroke, cerebrovascular disease, myocardial infarction, and peripheral vascular disease, preferably the disease or condition is atherosclerosis.

In another aspect, the invention provides a kit that includes a compound of Formula I or a composition thereof as described herein. In some embodiments, the compound or composition is packaged, e.g., in a vial, bottle, flask, which may be further packaged, e.g., within a box, envelope, or bag. In some embodiments, the compound or composition is approved by the U.S. Food and Drug Administration or similar regulatory agency for administration to a mammal, e.g., a human. In some embodiments, the compound or composition is approved for administration to a mammal, e.g., a human for a PPAR-mediated disease or condition or a disease or condition in which modulation of a PPAR provides a therapeutic benefit. In some embodiments, the kit includes written instructions or other indication that the compound or composition is suitable or approved for administration to a mammal, e.g., a human, for a PPAR-mediated disease or condition or a disease or condition in which modulation of a PPAR provides a therapeutic benefit. In some embodiments, the compound or composition is packaged in unit dose or single dose form, e.g., single dose pills, capsules, or the like.

In another aspect, the invention provides a method of treating or prophylaxis of a disease or condition in an animal subject, e.g., a PPAR-mediated disease or condition or a disease or condition in which modulation of a PPAR provides a therapeutic benefit, by administering to the subject a therapeutically effective amount of a compound of Formula I, a prodrug of such compound, a pharmaceutically acceptable salt of such compound or prodrug, or a pharmaceutically acceptable formulation of such compound or prodrug. The compound can be administered alone or can be administered as part of a pharmaceutical composition. In one aspect, the method involves administering to the subject an effective amount of a compound of Formula I in combination with one or more other therapies for the disease or condition.

In another aspect, the invention provides a method of treating or prophylaxis of a PPAR-mediated disease or condition or a disease or condition in which modulation of a PPAR provides a therapeutic benefit, wherein the method involves administering to the subject a therapeutically effective amount of a composition including a compound of Formula I.

In aspects and embodiments involving treatment or prophylaxis of a PPAR-mediated disease or condition, or a disease or condition in which modulation of a PPAR provides a therapeutic benefit, the disease or condition is selected from the group consisting of weight disorders (e.g., including, but not limited to, obesity, overweight condition, bulimia, and anorexia nervosa), lipid disorders (e.g., including, but not limited to, hyperlipidemia, dyslipidemia (including associated diabetic dyslipidemia and mixed dyslipidemia), hypoalphalipoproteinemia, hyperiglyceridemia, hypercholesterolemia, and low HDL (high density lipoprotein)), metabolic disorders (e.g., including, but not limited to, Metabolic Syndrome, Type II diabetes mellitus, Type I diabetes, hyperinsulinemia, impaired glucose tolerance, insulin resistance, diabetic complication (e.g., including, but not limited to, neuropathy, nephropathy, retinopathy, diabetic foot ulcer, bladder dysfunction, bowel dysfunction, diaphragmatic dysfunction and cataracts)), cardiovascular disease (e.g., including, but not limited to, hypertension, coronary heart disease, heart failure, congestive heart failure, atherosclerosis, arteriosclerosis, stroke, cerebrovascular disease, myocardial infarction, and peripheral vascular disease), inflammatory diseases (e.g., including, but not limited to, autoimmune diseases (e.g., including, but not limited to, vitiligo, uveitis, optic neuritis, pemphigus foliaceus, pemphigoid, inclusion body myositis, polymyositis, dermatomyositis, scleroderma, Grave's disease, Hashimoto's disease, chronic graft versus host disease, ankylosing spondylitis, rheumatoid arthritis, inflammatory bowel disease (e.g., ulcerative colitis, Crohn's disease), systemic lupus erythematosis, Sjogren's Syndrome, and multiple sclerosis), diseases involving airway inflammation (e.g., including, but not limited to, asthma and chronic obstructive pulmonary disease), inflammation in other organs (e.g., including, but not limited to, polycystic kidney disease (PKD), polycystic ovary syndrome, pancreatitis, nephritis, and hepatitis), otitis, stomatitis, sinusitis, arteritis, temporal arteritis, giant cell arteritis, and polymyalgia rheumatica), skin disorders (e.g., including, but not limited to, epithelial hyperproliferative diseases (e.g., including, but not limited to, eczema and psoriasis), dermatitis (e.g., including, but not limited to, atopic dermatitis, contact dermatitis, allergic dermatitis and chronic dermatitis), and impaired wound healing)), neurodegenerative disorders (e.g., including, but not limited to, Alzheimer's disease, Parkinson's disease, amyotrophic lateral sclerosis, spinal cord injury, and demyelinating disease (e.g., including, but not limited to, acute disseminated encephalomyelitis and Guillain-Barre syndrome)), coagulation disorders (e.g., including, but not limited to, thrombosis), gastrointestinal disorders (e.g., including, but not limited to, gastroesophageal reflux, appendicitis, diverticulitis, gastrointestinal ulcers, ileus, motility disorders and infarction of the large or small intestine), genitourinary disorders (e.g., including, but not limited to, renal insufficiency, erectile dysfunction, urinary incontinence, and neurogenic bladder), ophthalmic disorders (e.g., including, but not limited to, ophthalmic inflammation, conjunctivitis, keratoconjunctivitis, corneal inflammation, dry eye syndrome, macular degeneration, and pathologic neovascularization), infections (e.g., including, but not limited to, lyme disease, HCV, HIV, and *Helicobacter pylori*) and inflammation associated with infections (e.g., including, but not limited to, encephalitis, meningitis), neuropathic or inflammatory pain, pain syndromes (e.g., including, but not limited to, chronic pain syndrome, fibromyalgia), infertility, and cancer (e.g., including, but not limited to, breast cancer and thyroid cancer).

In some embodiments involving treatment or prophylaxis of a PPAR-mediated disease or condition, or a disease or condition in which modulation of a PPAR provides a therapeutic benefit, the disease or condition is selected from the group consisting of weight disorders, lipid disorders, metabolic disorders and cardiovascular disease. In some embodiments, the disease or condition is selected from the group consisting of obesity, dyslipidemia, Metabolic Syndrome, Type II diabetes mellitus and atherosclerosis.

In some embodiments involving treatment or prophylaxis of a PPAR-mediated disease or condition, or a disease or condition in which modulation of a PPAR provides a therapeutic benefit, the disease or condition is selected from the group consisting of inflammatory disease, neurodegenerative disorder, coagulation disorder, gastrointestinal disorder, genitourinary disorder, ophthalmic disorder, infection, inflammation associated with infection, neuropathic pain, inflammatory pain, pain syndromes, infertility and cancer. In some embodiments, the disease or condition is selected from the group consisting of inflammatory disease, neurodegenerative disorder, and cancer. In some embodiments, the disease or condition is selected from the group consisting of inflammatory bowel disease, multiple sclerosis, Alzheimer's disease, breast cancer and thyroid cancer.

In some embodiments involving treatment or prophylaxis of a PPAR-mediated disease or condition, or a disease or condition in which modulation of a PPAR provides a therapeutic benefit, the disease or condition is selected from the group consisting of weight disorders, lipid disorders and cardiovascular disease.

In some embodiments involving treatment or prophylaxis of a PPAR-mediated disease or condition, or a disease or condition in which modulation of a PPAR provides a therapeutic benefit, the disease or condition is selected from the group consisting of metabolic disorders, inflammatory diseases and neurodegenerative diseases.

In some embodiments involving treatment or prophylaxis of a PPAR-mediated disease or condition, or a disease or condition in which modulation of a PPAR provides a therapeutic benefit, the disease or condition is selected from the group consisting of ophthalmic disorders, infections and inflammation associated with infections.

In some embodiments involving treatment or prophylaxis of a PPAR-mediated disease or condition, or a disease or condition in which modulation of a PPAR provides a therapeutic benefit, the disease or condition is selected from the group consisting of neuropathic pain, inflammatory pain and pain syndromes.

In some embodiments involving treatment or prophylaxis of a PPAR-mediated disease or condition, or a disease or condition in which modulation of a PPAR provides a therapeutic benefit, the disease or condition is selected from the group consisting of infertility and cancer.

In some embodiments involving treatment or prophylaxis of a PPAR-mediated disease or condition, or a disease or condition in which modulation of a PPAR provides a therapeutic benefit, the disease or condition is selected from the group consisting of Metabolic Syndrome, Type II diabetes mellitus, Type I diabetes, hyperinsulinemia, impaired glucose tolerance, insulin resistance and a diabetic complication selected from the group consisting of neuropathy, nephropathy, retinopathy, diabetic foot ulcer, bladder dysfunction, bowel dysfunction, diaphragmatic dysfunction and cataracts, preferably the disease or condition is Metabolic Syndrome or Type II diabetes mellitus.

In some embodiments involving treatment or prophylaxis of a PPAR-mediated disease or condition, or a disease or condition in which modulation of a PPAR provides a therapeutic benefit, the disease or condition is selected from the group consisting of obesity, overweight condition, bulimia, anorexia nervosa, hyperlipidemia, dyslipidemia, hypoalphalipoproteinemia, hypertriglyceridemia, hypercholesterolemia, and low HDL, preferably the disease or condition is obesity or dyslipidemia.

In some embodiments involving treatment or prophylaxis of a PPAR-mediated disease or condition, or a disease or condition in which modulation of a PPAR provides a therapeutic benefit, the disease or condition is selected from the group consisting of Alzheimer's disease, Parkinson's disease, amyotrophic lateral sclerosis, spinal cord injury, and demyelinating disease, preferably the disease or condition is Alzheimer's disease.

In some embodiments involving treatment or prophylaxis of a PPAR-mediated disease or condition, or a disease or condition in which modulation of a PPAR provides a therapeutic benefit, the disease or condition is selected from the group consisting of vitiligo, uveitis, optic neuritis, pemphigus foliaceus, pemphigoid, inclusion body myositis, polymyositis, dermatomyositis, scleroderma, (Grave's disease, Hashimoto's disease, chronic graft versus host disease, ankylosing spondylitis, rheumatoid arthritis, inflammatory bowel disease systemic lupus erythematosis, Sjogren's Syndrome, and multiple sclerosis, asthma, chronic obstructive pulmonary disease, polycystic kidney disease, polycystic ovary syndrome, pancreatitis, nephritis, hepatitis, otitis, stomatitis, sinusitis, arteritis, temporal arteritis, giant cell arteritis, polymyalgia rheumatica, eczema, psoriasis, atopic dermatitis, contact dermatitis, allergic dermatitis, chronic dermatitis, and impaired wound healing, preferably the disease or condition is inflammatory bowel disease or multiple sclerosis.

In some embodiments involving treatment or prophylaxis of a PPAR-mediated disease or condition, or a disease or condition in which modulation of a PPAR provides a therapeutic benefit, the disease or condition is selected from the group consisting of infertility and cancer, preferably the disease or condition is breast or thyroid cancer.

In some embodiments involving treatment or prophylaxis of a PPAR-mediated disease or condition, or a disease or condition in which modulation of a PPAR provides a therapeutic benefit, the disease or condition is selected from the group consisting of hypertension, coronary heart disease, heart failure, congestive heart failure, atherosclerosis, arteriosclerosis, stroke, cerebrovascular disease, myocardial infarction, and peripheral vascular disease, preferably the disease or condition is atherosclerosis.

In some embodiments of aspects involving compounds of Formula I, the compound is specific for any one or any two of PPARα, PPARγ and PPARδ, e.g. specific for PPARα; specific for PPARδ; specific for PPARγ; specific for PPARα and PPARδ; specific for PPARα and PPARδ; or specific for PPARδ and PPARγ. In some embodiments, compounds are preferably specific for PPARδ. In some embodiments, compounds are preferably specific for PPARγ and PPARδ. In some embodiments, compounds are preferably specific for PPARα and PPARδ. Such specificity means that the compound has at least 5-fold greater activity (preferably at least 10-, 20-, 50-, or 100-fold or more greater activity) on the specific PPAR(s) than on the other PPAR(s), where the activity is determined using a biochemical assay suitable for determining PPAR activity, e.g., any assay known to one skilled in the art or as described herein. In some embodiments, compounds have significant activity on all three of PPARα, PPARδ, and PPARγ.

In some embodiments, a compound of Formula I will have an $EC_{50}$ of less than 100 nM, less than 50 nM, less than 20 nM, less than 10 nM, less than 5 nM, or less than 1 nM with respect to at least one of PPARα, PPARγ and PPARδ as determined in a generally accepted PPAR activity assay. In some embodiments, a compound of Formula I will have an $EC_{50}$ of less than 100 nM, less than 50 nM, less than 20 nM, less than 10 nM, less than 5 nM, or less than 1 nM with respect to at least any two of PPARα, PPARγ and PPARδ. In some embodiments, a compound of Formula I will have an $EC_{50}$ of less than 100 nM, less than 50 nM, less than 20 nM, less than 10 nM, less than 5 nM, or less than 1 nM with respect to all three of PPARα, PPARγ and PPARδ. In some embodiments, a compound of the invention may be a specific agonist of any one of PPARα, PPARγ and PPARδ, or any two of PPARα, PPARγ and PPARδ. In some embodiments, a compound of the invention will preferably have an $EC_{50}$ of less than 100 nM, less than 50 nM, less than 20 nM, less than 10 nM, less than 5 nM, or less than 1 nM with respect to at least PPARδ as determined in a generally accepted PPAR activity assay. In some embodiments, a compound of the invention will preferably have an $EC_{50}$ of less than 100 nM, less than 50 nM, less than 20 nM, less than 10 nM, less than 5 nM, or less than 1 nM with respect to PPARδ and PPARγ as determined in a generally accepted PPAR activity assay. In some embodiments, a compound of the invention will preferably have an $EC_{50}$ of less than 100 nM, less than 50 nM, less than 20 nM, less than 10 nM, less than 5 nM, or less than 1 nM with respect to PPARδ and PPARα as determined in a generally accepted PPAR activity assay. A specific agonist of one of PPARα, PPARγ and PPARδ is such that the $EC_{50}$ for one of PPARα, PPARγ and PPARδ will be at least about 5-fold, also 10-fold, also 20-fold, also 50-fold, or at least about 100-fold less than the $EC_{50}$ for the other two of PPARα, PPARγ and PPARδ. A specific agonist of two of PPARα, PPARγ and PPARδ is such that the $EC_{50}$ for each of two of PPARα, PPARγ and PPARδ will be at least about 5-fold, also 10-fold, also 20-fold, also 50-fold, or at least about 100-fold less than the $EC_{50}$ for the other of PPARα, PPARγ and PPARδ.

In some embodiments of the invention, the compounds of Formula I active on PPARs also have desireable pharmacologic properties. In some embodiments the desired pharmacologic property is PPAR pan-activity, PPAR selectivity for any individual PPAR (PPARα, PPARδ, or PPARγ), selectivity on any two PPARs (PPARα and PPARδ, PPARα and PPARγ, or PPARδ and PPARγ), or any one or more of serum half-life longer than 2 hr, also longer than 4 hr, also longer than 8 hr, aqueous solubility, and oral bioavailability more than 10%, also more than 20%.

Additional embodiments will be apparent from the Detailed Description of the Invention and from the claims.

DETAILED DESCRIPTION OF THE INVENTION

As indicated in the Summary of the Invention above, the present invention concerns the peroxisome proliferator-activated receptors (PPARs), which have been identified in humans and other mammals. A group of compounds have been identified, corresponding to Formula I, that are active on one or more of the PPARs, in particular compounds that are active on one or more human PPARs. Such compounds can be used as agonists on PPARs, including agonists of at least one of PPARα, PPARδ, and PPARγ, as well as dual PPAR agonists and pan-agonist, such as agonists of both PPARα and PPARγ, both PPARα and PPARδ, both PPARγ and PPARδ, or agonists of PPARα, PPARγ and PPARδ.

As used herein the following definitions apply unless otherwise indicated:

"Halogen"-alone or in combination refers to all halogens, that is, chloro (Cl), fluoro (F), bromo (Br), or iodo (I).

"Hydroxyl" or "hydroxy" refers to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. "Substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —NO$_2$, —CN, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NR$^a$R$^a$, —C(S)NR$^a$R$^a$, —S(O)$_2$NR$^a$R$^a$, —C(NH)NR$^b$R$^c$, —NR$^a$C(O)R$^a$, —NR$^a$C(S)R$^a$, —NR$^a$S(O)$_2$R$^a$, —NR$^a$C(O)NR$^a$R$^a$, —NR$^a$C(S)NR$^a$R$^a$, —NR$^a$S(O)$_2$NR$^a$R$^a$, —NR$^a$R$^a$, —R$^e$, and —R$^f$. Furthermore, possible substitutions include subsets of these substitutions, such as are indicated herein, for example, in the description of compounds of Formula I, attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. It is understood that substitutions are attached at any available atom to produce a stable compound, when optionally substituted lower alkyl is an R group of a moiety such as —OR (e.g. lower alkoxy), —SR (e.g. lower alkylthio), —NHR (e.g. monoalkylamino), —C(O)NHR, and the like, substitution of the lower alkyl R group is preferably such that substitution of the lower alkyl carbon bound to any O, S, or N of the moiety (except where N is a heteroaryl ring atom) excludes substituents that would result in any O, S, or N of the substituent (except where N is a heteroaryl ring atom) being bound to the lower alkyl carbon bound to any O, S, or N of the moiety.

"Lower alkenyl" alone or in combination means a straight or branched hydrocarbon containing 2-6 carbon atoms (unless specifically defined) ad at least one, preferably 1-3, more preferably 1-2, most preferably one, carbon to carbon double bond. Carbon to carbon double bonds may be contained within either a straight chain or branched portion. Examples of lower alkenyl groups include ethenyl, propenyl, isopropenyl, butenyl, and the like. "Substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —NO$_2$, —CN, —OR$^a$, —SR$^a$,—OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NR$^a$R$^a$, —C(S)NR$^a$R$^a$, —S(O)$_2$NR$^a$R$^a$, —C(NH)NR$^b$R$^c$, —NR$^a$C(O)R$^a$, —NR$^a$C(S)R$^a$, —NR$^a$S(O)$_2$R$^a$, —NR$^a$C(O)NR$^a$R$^a$, —NR$^a$C(S)NR$^a$R$^a$, —NR$^a$S(O)$_2$NR$^a$R$^a$, —NR$^a$R$^a$, —R$^d$, and —R$^f$. Further, possible substitutions include subsets of these substitutions, such as are indicated herein, for example, in the description of compounds of Formula I, attached at any available atom to produce a stable compound. It is understood that substitutions are attached at any available atom to produce a stable compound, substitution of lower alkenyl groups are preferably such that F, C(O), C(S), C(NH), S(O), S(O)$_2$, O, S, or N (except where N is a heteroaryl ring atom), are not bound to an alkene carbon thereof. Further, where lower alkenyl is a substituent of another moiety or an R group of a moiety such as —OR, —NHR, —C(O)R, and the like, substitution of the moiety is preferably such that any C(O), C(S), S(O), S(O)$_2$, O, S, or N thereof (except where N is a heteroaryl ring atom) are not bound to an alkene carbon of the lower alkenyl substituent or R group. Further, where lower alkenyl is a substituent of another moiety or an R group of a moiety such as —OR, —NHR, —C(O)NHR, and the like, substitution of the lower alkenyl R group is preferably such that substitution of the lower alkenyl carbon bound to any O, S, or N of the moiety (except where N is a heteroaryl ring atom) excludes substituents that would result in any O, S, or N of the substituent (except where N is a heteroaryl ring atom) being bound to the lower alkenyl carbon bound to any O, S, or N of the moiety. An "alkenyl carbon" refers to any carbon within a lower alkenyl group, whether saturated or part of the carbon to carbon double bond. An "alkene carbon" refers to a carbon within a lower alkenyl group that is part of a carbon to carbon double bond. "C$_{3-6}$ alkenyl" denotes lower alkenyl containing 3-6 carbon atoms. A "substituted C$_{3-6}$ alkenyl" denotes optionally substituted lower alkenyl containing 3-6 carbon atoms.

"Lower alkynyl" alone or in combination means a straight or branched hydrocarbon containing 2-6 carbon atoms (unless specifically defined) containing at least one, preferably one, carbon to carbon triple bond. Examples of lower alkynyl groups include ethynyl, propynyl, butynyl, and the like. "Substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —NO$_2$, —CN, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NR$^a$R$^a$, —C(S)NR$^a$R$^a$, —S(O)$_2$NR$^a$R$^a$, —C(NH)NR$^b$R$^c$, —NR$^a$C(O)R$^a$, —NR$^a$C(S)R$^a$, —NR$^a$S(O)$_2$R$^a$, —NR$^a$C(O)NR$^a$R$^a$, —NR$^a$C(S)NR$^a$R$^a$, —NR$^a$S(O)$_2$NR$^a$R$^a$, —NR$^a$R$^a$, —R$^d$, and —R$^f$. Further, possible substitutions include subsets of these substitutions, such as are indicated herein, for example, in the description of compounds of Formula I, attached at any available atom to produce a stable compound. It is understood that substitutions are attached at any available atom to produce a stable compound, substitution of lower alkynyl groups are preferably such that F, C(O), C(S), C(NH), S(O), S(O)$_2$, O, S, or N (except where N is a heteroaryl ring atom) are not bound to an alkyne carbon thereof. Further, where lower alkynyl is a substituent of another moiety or an R group of a moiety such as —OR, —NHR, —C(O)R, and the like, substitution of the moiety is preferably such that any C(O), C(S), S(O), S(O)$_2$, O, S, or N thereof (except where N is a heteroaryl ring atom) are not bound to an alkyne carbon of the lower alkynyl substituent or R group. Further, where lower alkynyl is a substituent of another moiety or an R group of a moiety such as —OR, —NHR, —C(O)NHR, and the like, substitution of the lower alkynyl R group is preferably such that substitution of the lower alkynyl carbon bound to any O, S, or N of the moiety (except where N is a heteroaryl ring atom) excludes substituents that would result in any O, S, or N of the substituent (except where N is a heteroaryl ring atom) being bound to the lower alkynyl carbon bound to any O, S, or N of the moiety. An "alkynyl carbon" refers to any carbon within a lower alkynyl group, whether saturated or part of the carbon to carbon triple bond. An "alkyne carbon" refers to a carbon within a lower alkynyl group that is pan of a carbon to carbon triple bond. "$C_{3-6}$ alkynyl" denotes lower alkynyl containing 3-6 carbon atoms. A "substituted $C_{3-6}$ alkynyl" denotes optionally substituted lower alkynyl containing 3-6 carbon atoms.

"Carboxylic acid isostere" refers to a moiety that mimics a carboxylic acid by virtue of similar physical properties, including but not limited to molecular size, charge distribution or molecular shape. Exemplary carboxylic acid isosteres are selected from the group consisting of thiazolidine dione (i.e.

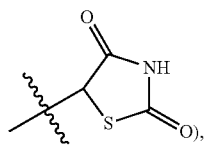

hydroxamic acid (i.e. —C(O)NHOH), acyl-cyanamide (i.e. —C(O)NHCN), tetrazole (i.e.

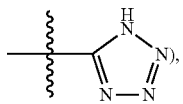

3- or 5-hydroxy isoxazole (i.e.

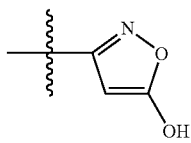

or

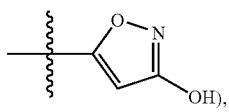

3- or 5-hydroxy isothiazole (i.e.

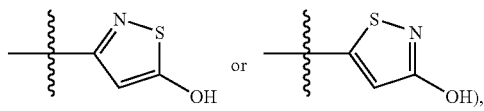

sulphonate (i.e. —S(O)$_2$OH), and sulfonamide (i.e. —S(O)$_2$NH$_2$). 3- or 5- hydroxy isoxazole or 3- or 5-hydroxy isothiazole may be optionally substituted at either or both of the ring CH or the OH group with lower alkyl or lower alkyl substituted with 1, 2 or 3 substituents selected from the group consisting of fluoro, aryl and heteroaryl, wherein aryl or heteroaryl may further be optionally substituted with 1, 2, or 3 substituents selected from the group consisting of halogen, lower alkyl, fluoro substituted lower alkyl, lower alkoxy, fluoro substituted lower alkoxy, lower alkylthio, and fluoro substituted lower alkylthio. The nitrogen of the sulfonamide may be optionally substituted with a substituent selected from the group consisting of lower alkyl fluoro substituted lower alkyl, acetyl (i.e. —C(O)CH$_3$), aryl and heteroaryl, wherein aryl or heteroaryl may further be optionally substituted with 1, 2, or 3 substituents selected from the group consisting of halogen, lower alkyl fluoro substituted lower alkyl, lower alkoxy, fluoro substituted lower alkoxy, lower alkylthio, and fluoro substituted lower alkylthio.

"Aryl" alone or in combination refers to a monocyclic or bicyclic ring system containing aromatic hydrocarbons such as phenyl or naphthyl, which may be optionally fused with a cycloalkyl or heterocycloalkyl of preferably 5-7, more preferably 5-6, ring members. "Arylene" refers to a divalent aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinoxalinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to heteroaryl wherein any heteroatoms are N. "Heteroarylene" refers to a divalent heteroaryl.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like.

"Heterocycoalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which one of the ring carbons is oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl.

"Optionally substituted aryl", "optionally substituted heteroaryl", "optionally substituted cycloalkyl", and "optionally substituted heterocycloalkyl", refers to aryl, heteroaryl, cycloalkyl and heterocycloalkyl groups, respectively, which are optionally independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —$NO_2$, —CN, —$OR^a$, —$SR$ , —$OC(O)R^a$, —$OC(S)R^a$, —$C(O)R^a$, —$C(S)R^a$, —$C(O)OR^a$, —$C(S)OR^a$, —$S(O)R^a$, —$S(O)_2R^a$, —$C(O)NR^aR^a$, —$C(S)NR^aR^a$, —$S(O)_2NR^aR^a$, —$C(NH)NR^bR^c$, —$NR^aC(O)R^a$, —$NR^aC(S)R^a$, —$NR^aS(O)_2R^a$, —$NR^aC(O)NR^aR^a$, —$NR^aC(S)NR^aR^a$, —$NR^aS(O)_2NR^aR^a$, —$NR^aR^a$, —$R^d$, —$R^e$, and —$R^f$. It is understood that with any substitution of aryl, heteroaryl, cycloalkyl, and heterocycloalkyl, including, for example, selection of $R^7$, selected substituents, including any combinations thereof, are chemically feasible and provide a stable compound.

The variables as used in the description of optional substituents for lower alkyl, lower alkenyl, lower alkynyl, cycloalkyl, heterocycloalkyl, aryl and heteroaryl are defined as follows:

- —$R^a$, —$R^b$, and —$R^c$ at each occurrence are independently selected from the group consisting of hydrogen, —$R^d$, —$R^e$, and —$R^f$ provided, however, that $R^a$ bound to S of any $SR^a$, $S(O)R^a$, or $S(O)_2R^a$, or C of any $C(S)R^a$ or $C(O)R^a$ is not hydrogen, or
- —$R^b$ and —$R^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, cycloalkylamino, —$NO_2$, —CN, —$OR^k$, —$SR^k$, —$NR^kR^k$, —$R^m$, and —$R^o$;
- —$R^d$ at each occurrence is independently lower alkyl optionally substituted with one or more, preferably 1, 2, 3, 4 or 5, also 1, 2 or 3 substituents selected from the group consisting of fluoro, —$OR^g$, —$SR^g$, —$NR^gR^g$, —$C(O)R^g$, —$C(S)R^g$, —$S(O)R^g$, —$S(O)_2R^g$, —$OC(O)R^g$, —$OC(S)R^g$, —$C(O)OR^g$, —$C(S)OR^g$, —$C(O)NR^gR^g$, —$C(S)NR^gR^g$, —$S(O)_2NR^gR^g$, —$NR^gC(O)R^g$, —$NR^gC(S)R^g$, —$NR^gS(O)_2R^g$, —$NR^gC(O)NR^gR^g$, —$NR^gC(S)NR^gR^g$, —$NR^gS(O)_2NR^gR^g$, and —$R^f$;
- —$R^e$ at each occurrence is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —$OR^g$, —$SR^g$, —$NR^gR^g$, —$C(O)R^g$, —$C(S)R^g$, —$S(O)R^g$, —$S(O)_2R^g$, —$OC(O)R^g$, —$OC(S)R^g$, —$C(O)OR^g$, —$C(S)OR^g$, —$C(O)NR^gR^g$, —$C(S)NR^gR^g$, —$S(O)_2NR^gR^g$, —$NR^gC(O)R^g$, —$NR^gC(S)R^g$, —$NR^gS(O)R^g$, —$NR^gC(O)NR^gR^g$, —$NR^gC(S)NR^gR^g$, —$NR^gS(O)_2NR^gR^g$, —$R^d$, and —$R^f$;
- —$R^f$ at each occurrence is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —$NO_2$, —CN, —$OR^g$, —$SR^g$, —$NR^gR^g$, —$C(O)R^g$, —$C(S)R^g$, —$S(O)R^g$, —$S(O)_2R^g$, —$OC(O)R^g$, —$OC(S)R^g$, —$C(O)OR^g$, —$C(S)OR^g$, —$C(O)NR^gR^g$, —$C(S)NR^gR^g$, —$S(O)_2NR^gR^g$, —$NR^gC(O)R^g$, —$NR^gC(S)R^g$, —$NR^gS(O)_2R^g$, —$NR^gC(O)NR^gR^g$, —$NR^gC(S)NR^gR^g$, —$NR^gS(O)_2NR^gR^g$, —$R^m$, and —$R^o$;
- —$R^g$ at each occurrence is independently selected from the group consisting of hydrogen, —$R^h$, —$R^i$, and —$R^j$, provided, however, that $R^g$ bound to S of any $SR^g$, $S(O)R^g$, or $S(O)_2R^g$, or C of any $C(S)R^g$ or $C(O)R^g$ is not hydrogen;
- —$R^h$ at each occurrence is independently lower alkyl optionally substituted with one or more, preferably 1, 2, 3, 4 or 5, also 1, 2, or 3 substituents selected from the group consisting of fluoro, —$OR^k$, —$SR^k$, —$NR^kR^k$, —$C(O)R^k$, —$C(S)R^k$, —$S(O)R^k$, —$S(O)_2R^k$, —$C(O)NR^kR^k$, —$C(S)NR^kR^k$, —$S(O)_2NR^kR^k$, —$NR^kC(O)R^k$, —$NR^kC(S)R^k$, —$NR^kS(O)_2R^k$, —$NR^kC(O)NR^kR^k$, —$NR^kC(S)NR^kR^k$, —$NR^kS(O)_2NR^kR^k$, and —$R^o$, provided, however, that any substitution on the lower alkyl carbon bound to any O, S, or N of any $OR^h$, $SR^h$, or $NR^h$ is selected from the group consisting of fluoro and —$R^o$;
- —$R^i$ at each occurrence is independently selected from the group consisting of $C_{3-6}$ alkenyl and $C_{3-6}$ alkynyl, wherein $C_{3-6}$ alkenyl or $C_{3-6}$ alkynyl are optionally substituted with one or more, preferably 1, 2, 3, 4 or 5, also 1, 2, or 3 substituents selected from the group consisting of fluoro, —$OR^k$, —$SR^k$, —$NR^kR^k$, —$C(O)R^k$, —$C(S)R^k$, —$S(O)R^k$, —$S(O)_2R^k$, —$C(O)NR^kR^k$, —$C(S)NR^kR^k$, —$S(O)_2NR^kR^k$, —$NR^kC(O)R^k$, —$NR^kC(S)R^k$, —$NR^kS(O)_2R^k$, —$NR^kC(O)NR^kR^k$, —$NR^kC(S)NR^kR^k$, —$NR^kS(O)_2NR^kR^k$, —$R^m$ and —$R^o$, provided, however, that any substitution on the alkenyl or alkynyl carbon bound to any O, S or N of any $OR^i$, $SR^i$, or $NR^i$ is selected from the group consisting of fluoro, —$R^m$ and —$R^o$;
- $R^j$ at each occurrence is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —$NO_2$, —CN, —$OR^k$, —$SR^k$, —$NR^kR^k$, —$C(O)R^k$, —$C(S)R^k$, —$S(O)R^k$, —$S(O)_2R^k$, —$C(O)NR^kR^k$, —$C(S)NR^kR^k$, —$S(O)_2NR^kR^k$, —$NR^kC(O)R^k$, —$NR^kC(S)R^k$, —$NR^kS(O)_2R^k$, —$NR^kC(O)NR^kR^k$, —$NR^kC(S)NR^kR^k$, —$NR^kS(O)_2NR^kR^k$, —$R^m$, and —$R^o$;
- —$R^m$ at each occurrence is independently selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —$R^o$, fluoro, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —$R^o$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;
- —$R^k$ at each occurrence is independently selected from the group consisting of hydrogen, —$R^n$, and —$R^o$, provided, however, that $R^k$ bound to S of any $SR^k$, $S(O)R^k$, or $S(O)_2R^k$, or C of any $C(S)R^k$ or $C(O)R^k$ is not hydrogen;
- $R^n$ at each occurrence is independently selected from the group consisting of lower alkyl, $C_{3-6}$ alkenyl and $C_{3-6}$ alkynyl, wherein lower alkyl is optionally substituted with one or more, preferably 1, 2, 3, 4 or 5, also 1, 2, or 3 substituents selected from the group consisting of —$R^o$, fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to the O of OR″, S of SR″, or N of any NR″ is fluoro or —R°, and wherein $C_{3-6}$ alkenyl or $C_{3-6}$ alkynyl are optionally substituted with one or more, preferably 1, 2, 3, 4 or 5, also 1, 2, or 3 substituents selected from the group consisting of —R°, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the $C_{3-6}$ alkenyl or $C_{3-6}$ alkynyl carbon bound to the the O of OR″, S of SR″, or N of any NR″ is fluoro, lower alkyl, fluoro substituted lower alkyl, or —R°;

—R° at each occurrence is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —OR$^p$, where R$^p$ is lower alkyl, "Optionally substituted lower alkoxy" denotes lower alkoxy in which R$^p$ is optionally substituted lower alkyl. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on lower alkoxy are attached at any available atom to produce a stable compound, substitution of lower alkoxy is preferably such that O, S, or N (except where N is a heteroaryl ring atom), are not bound to the lower alkyl carbon bound to the lower alkoxy O. Further, where lower alkoxy is described as a substituent of another moiety, the lower alkoxy oxygen is preferably not bound to a carbon atom that is bound to an O, S, or N of the other moiety (except where N is a heteroaryl ring atom), or to an alkene or alkyne carbon of the other moiety.

"Aryloxy" denotes the group —OR$^q$, where R$^q$ is aryl. "Optionally substituted aryloxy" denotes aryloxy in which R$^q$ is optionally substituted aryl. "Heteroaryloxy" denotes the group —OR$^r$, where R$^r$ is heteroaryl. "Optionally substituted heteroaryloxy" denotes heteroaryloxy in which R$^r$ is optionally substituted heteroaryl.

"Lower alkylthio" denotes the group —SR$^s$, where R$^s$ is lower alkyl. "Substituted lower alkylthio" denotes lower alkylthio in which R$^s$ is optionally substituted lower alkyl. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on lower alkylthio are attached at any available atom to produce a stable compound, substitution of lower alkylthio is such that O, S, or N (except where N is a heteroaryl ring atom), are preferably not bound to the lower alkyl carbon bound to the lower alkylthio S. Further, where lower alkylthio is described as a substituent of another moiety, the lower alkylthio sulfur is preferably not bound to a carbon atom that is bound to an O, S, or N of the other moiety (except where N is a heteroaryl ring atom), or to an alkene or alkyne carbon of the other moiety.

"Amino" or "amine" denotes the group —NH$_2$. "Mono-alkylamino" denotes the group —NHR$^t$ where R$^t$ is lower alkyl. "Di-alkylamino" denotes the group —NR$^t$R$^u$, where R$^t$ and R$^u$ are independently lower alkyl. "Cycloalkylamino" denotes the group —NR$^v$R$^w$, where R$^v$ and R$^w$ combine with the nitrogen to form a 5-7 membered heterocycloalkyl, where the heterocycloalkyl may contain an additional heteroatom within the ring, such as O, N, or S, and may also be further substituted with lower alkyl. Examples of cycloalkylamino include, but are not limited to, piperidine, piperazine, 4-methylpiperazine, morpholine, and thiomorpholine. It is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is preferably not bound to a carbon atom that is bound to an O, S, or N of the other moiety (except where N is a heteroaryl ring atom) or to an alkene or alkyne carbon of the other moiety.

As used herein in connection with PPAR modulating compound, binding compounds or ligands, the term "specific for PPAR" and terms of like import mean that a particular compound binds to a PPAR to a statistically greater extent than to other biomolecules that may be present in or originally isolated from a particular organism, e.g., at least 2, 3, 4, 5, 10, 20, 50, 100, or 1000-fold greater binding. Also, where biological activity other than binding is indicated, the term "specific for PPAR" indicates that a particular compound has greater biological activity associated with binding to a PPAR than to other biomolecules (e.g., at a level as indicated for binding specificity). Similarly, the specificity can be for a specific PPAR with respect to other PPARs that may be present in or originally isolated from a particular organism.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. In some cases, the specificity is with reference to a limited set of other biomolecules, e.g., in the case of PPARs, in some cases the reference may be other receptors, or for a particular PPAR, it may be other PPARs. In some embodiments, the greater specificity is at least 2, 3, 4, 5, 8, 10, 50, 100, 200, 400, 500, or 1000-fold greater specificity. In the context of ligands interacting with PPARs, the terms "activity on", "activity toward," and like terms mean that such ligands have EC$_{50}$ less than 10 µM, less than 1 µM, less than 100 nM, less than 50 nM, less than 20 nM, less than 10 nM, less than 5 nM, or less than 1 nM with respect to at least one PPAR as determined in a generally accepted PPAR activity assay.

The term "composition" or "pharmaceutical composition" refers to a formulation suitable for administration to an intended animal subject for therapeutic purposes. The formulation includes a therapeutically significant quantity (i.e. a therapeutically effective amount) of at least one active compound and at least one pharmaceutically acceptable carrier or excipient, which is prepared in a form adapted for administration to a subject. Thus, the preparation is "pharmaceutically acceptable", indicating that it does not have properties that would cause a reasonably prudent medical practitioner to avoid administration of the material to a patient, taking into consideration the disease or conditions to be treated and the respective route of administration. In many cases, such a pharmaceutical composition is a sterile preparation, e.g. for injectibles.

The term "PPAR-mediated" disease or condition and like terms refer to a disease or condition in which the biological function of a PPAR affects the development and/or course of the disease or condition, and/or in which modulation of PPAR alters the development, course, and/or symptoms of the disease or condition. Similarly, the phrase "PPAR modulation provides a therapeutic benefit" indicates that modulation of the level of activity of PPAR in a subject indicates that such modulation reduces the severity and/or duration of the disease, reduces the likelihood or delays the onset of the disease or condition, and/or causes an improvement in one or more symptoms of the disease or condition. In some cases the disease or condition may be mediated by any one or more of the PPAR isoforms, e.g., PPARγ, PPARα, PPARδ, PPARγ and PPARα, PPARγ and PPARδ, PPARα and PPARδ, or PPARγ, PPARα, and PPARδ. In some cases, modulation of any one or more of the PPAR isoforms, e.g., PPARγ, PPARα, PPARδ, PPARγ and PPARα, PPARγ and PPARδ, PPARα and PPARδ, or PPARγ, PPARα, and PPARδ provides a therapeutic benefit.

The term "therapeutically effective" or "effective amount" indicates that the materials or amount of material is effective to prevent, alleviate, or ameliorate one or more symptoms of a disease or medical condition, and/or to prolong the survival of the subject being treated.

The term "PPAR" refers to a peroxisome proliferator-activated receptor as recognized in the art. As indicated above, the PPAR family includes PPARα (also referred to as PPARa or PPARalpha), PPARδ (also referred to as PPARd or PPAR-delta), and PPARγ (also referred to as PPARg or PPAR-gamma). Additional details regarding identification of the individual PPARs by their sequences can be found, for example, in US Patent Application Publication number US 2007/0072904, the disclosure of which is hereby incorporated by reference in its entirety As used herein in connection with the design or development of ligands, the term "bind" and "binding" and like terms refer to a non-convalent energetically favorable association between the specified molecules (i.e., the bound state has a lower free energy than the separated state, which can be measured calorimetrically). For binding to a target, the binding is at least selective, that is, the compound binds preferentially to a particular target or to members of a target family at a binding site, as compared to non-specific binding to unrelated proteins not having a similar binding site. For example, BSA is often used for evaluating or controlling for non-specific binding. In addition, for an association to be regarded as binding, the decrease in free energy going from a separated state to the bound state must be sufficient so that the association is detectable in a biochemical assay suitable for the molecules involved.

By "assaying" is meant the creation of experimental conditions and the gathering of data regarding a particular result of the experimental conditions. For example, enzymes can be assayed based on their ability to act upon a detectable substrate. Likewise, for example, a compound or ligand can be assayed based on its ability to bind to a particular target molecule or molecules and, or to modulate an activity of a target molecule.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "clog P" is meant the calculated log P of a compound, "P" referring to the partition coefficient of the compound between a lipophilic and an aqueous phase, usually between octanol and water.

In the context of compounds binding to a target, the term "greater affinity" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

By binding with "moderate affinity" is meant binding with a $K_D$ of from about 200 nM to about 1 μM under standard conditions. By "moderately high affinity" is meant binding at a $K_D$ of from about 1 nM to about 200 nM. By binding at "high affinity" is meant binding at a $K_D$ of below about 1 nM under standard conditions. The standard conditions for binding are at pH 7.2 at 37° C. for one hour. For example, typical binding conditions in a volume of 100 μl/well would comprise a PPAR, a test compound, HEPES 50 mM buffer at pH 7.2, NaCl 15 mM, ATP 2 μM, and bovine serum albumin (1 μg/well), at 37° C. for one hour.

Binding compounds can also be characterized by their effect on the activity of the target molecule. Thus, a "low activity" compound has an inhibitory concentration ($IC_{50}$) (for inhibitors or antagonists) or effective concentration ($EC_{50}$) (applicable to agonists) of greater than 1 μM under standard conditions. By "moderate activity" is meant an $IC_{50}$ or $EC_{50}$ of 200 nM to 1 μM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured. For PPAR agonists, activities can be determined as described in the Examples, or using other such assay methods known in the art.

By "protein" is meant a polymer of amino acids. The amino acids can be naturally or non-naturally occurring. Proteins can also contain modifications, such as being glycosylated, phosphorylated, or other common modifications.

By "protein family" is meant a classification of proteins based on structural and/or functional similarities. For example, kinases, phosphatases, proteases, and similar groupings of proteins are protein families. Proteins can be grouped into a protein family based on having one or more protein folds in common, a substantial similarity in shape among folds of the proteins, homology, or based on having a common function. In many cases, smaller families will be specified, e.g., the PPAR family.

By "specific biochemical effect" is meant a therapeutically significant biochemical change in a biological system causing a detectable result. This specific biochemical effect can be, for example, the inhibition or activation of an enzyme, the inhibition or activation of a protein that binds to a desired target, or similar types of changes in the body's biochemistry. The specific biochemical effect can cause alleviation of symptoms of a disease or condition or another desirable effect. The detectable result can also be detected through an intermediate step.

By "standard conditions" is meant conditions under which an assay is performed to obtain scientifically meaningful data. Standard conditions are dependent on the particular assay, and can be generally subjective. Normally the standard conditions of an assay will be those conditions that are optimal for obtaining useful data from the particular assay. The standard conditions will generally minimize background signal and maximize the signal sought to be detected.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

In the context of this invention, by "target molecule" is meant a molecule that a compound, molecular scaffold, or ligand is being assayed for binding to. The target molecule has an activity that binding of the molecular scaffold or ligand to the target molecule will alter or change. The binding of the compound, scaffold, or ligand to the target molecule can preferably cause a specific biochemical effect when it occurs in a biological system. A "biological system" includes, but is not limited to, a living system such as a human, animal, plant, or insect. In most but not all cases, the target molecule will be a protein or nucleic acid molecule.

By "pharmacophore" is meant a representation of molecular features that are considered to be responsible for a desired activity, such as interacting or binding with a receptor. A pharmacophore can include 3-dimensional (hydrophobic groups, charged/ionizable groups, hydrogen bond donors/acceptors), 2D (substructures), and 1D (physical or biological) properties.

As used herein in connection with numerical values, the terms "approximately" and "about" mean ±10% of the indicated value.

Applications of PPAR Agonists

The PPARs have been recognized as suitable targets for a number of different diseases and conditions. Some of those applications are described, for example, in US Patent Application Publication number US 2007/0072904, the disclosure of which is hereby incorporated by reference in its entirety. Additional applications are known and the present compounds can also be used for those diseases and conditions.

Thus, PPAR agonists, such as those described herein by Formulae I, Ia, Ib, Ic, Id, Ie, If, Ig, Ih, or Ii can be used in the prophylaxis and/or therapeutic treatment of a variety of different diseases and conditions, such as weight disorders (e.g., including, but not limited to, obesity, overweight condition, bulimia, and anorexia nervosa), lipid disorders (e.g., including, but not limited to, hyperlipidemia, dyslipidemia (including associated diabetic dyslipidemia and mixed dyslipidemia), hypoalphalipoproteinemia, hyperiglyceridemia, hypercholesterolemia, and low HDL (high density lipoprotein)), metabolic disorders (e.g., including, but not limited to, Metabolic Syndrome, Type II diabetes mellitus, Type I diabetes, hyperinsulinemia, impaired glucose tolerance, insulin resistance, diabetic complication (e.g., including, but not limited to, neuropathy, nephropathy, retinopathy, diabetic foot ulcer, bladder dysfunction, bowel dysfunction, diaphragmatic dysfunction and cataracts)), cardiovascular disease (e.g., including, but not limited to, hypertension, coronary heart disease, heart failure, congestive heart failure, atherosclerosis, arterosclerosis, stroke, cerebrovascular disease, myocardial infarction, and peripheral vascular disease), inflammatory diseases (e.g., including, but not limited to, autoimmune diseases (e.g., including, but not limited to, vitiligo, uveitis, optic neuritis, pemphigus foliaceus, pemphigoid, inclusion body myositis, polymyositis, dermatomyositis, scleroderma, Grave's disease, Hashimoto's disease, chronic graft versus host disease, ankylosing spondylitis, rheumatoid arthritis, inflammatory bowel disease (e.g. ulcerative colitis, Crohn's disease), systemic lupus erythematosis, Sjogren's Syndrome, and multiple sclerosis), diseases involving airway inflammation (e.g., including, but not limited to, asthma and chronic obstructive pulmonary disease), inflammation in other organs (e.g., including, but not limited to, polycystic kidney disease (PKD), polycystic ovary syndrome, pancreatitis, nephritis, and hepatitis), otitis, stomatitis, sinusitis, arteritis, temporal arteritis, giant cell arteritis, and polymyalgia rheumatica), skin disorders (e.g., including, but not limited to, epithelial hyperproliferative diseases (e.g., including, but not limited to, eczema and psoriasis), dermatitis (e.g., including, but not limited to, atopic dermatitis, contact dermatitis, allergic dermatitis and chronic dermatitis), and impaired wound healing)), neurodegenerative disorders (e.g., including, but not limited to, Alzheimer's disease, Parkinson's disease, amyotrophic lateral sclerosis, spinal cord injury, and demyelinating disease (e.g., including, but not limited to, acute disseminated encephalomyelitis and Guillain-Barre syndrome)), coagulation disorders (e.g., including, but not limited to, thrombosis), gastrointestinal disorders (e.g., including, but not limited to, gastroesophageal reflux, appendicitis, diverticulitis, gastrointestinal ulcers, ileus, motility disorders and infarction of the large or small intestine), genitourinary disorders (e.g., including, but not limited to, renal insufficiency, erectile dysfunction, urinary incontinence, and neurogenic bladder), ophthalmic disorders (e.g., including, but not limited to, ophthalmic inflammation, conjunctivitis, keratoconjunctivitis, corneal inflammation, dry eye syndrome, macular degeneration, and pathologic neovascularization), infections (e.g., including, but not limited to, lyme disease, HCV, HIV, and *Helicobacter pylori*) and inflammation associated with infections (e.g., including, but not limited to, encephalitis, meningitis), neuropathic or inflammatory pain, pain syndromes (e.g., including, but not limited to, chronic pain syndrome, fibromyalgia), infertility, and cancer (e.g., including, but not limited to, breast cancer and thyroid cancer).

PPAR Active Compounds

As indicated in the Summary of the Invention and in connection with applicable diseases and conditions, a number of different PPAR agonists have been identified. In addition, the present invention provides PPAR agonist compounds described by Formulae I, Ia, Ib, Ic, Id, Ie, If, Ig, Ih, or Ii as provided in the Summary of the Invention.

The activity of the compounds can be assessed using methods known to those of skill in the art, including, for example, methods described in US Patent Application Publication number US 2007/0072904, the disclosure of which is hereby incorporated by reference in its entirety.

(c) Isomers, Prodrugs, and Active Metabolites

Compounds contemplated herein are described with reference to both generic formulae and specific compounds. In addition, the invention compounds may exist in a number of different forms or derivatives, all within the scope of the present invention. Alternative forms or derivatives, such as (a)Isomers, Prodrugs, and Active Metabolites (b) Tautomers, Stereoisomers, Regioisomers, and Solvated Forms (c) Prodrugs and Metabolites (d) Pharmaceutically acceptable salts (e) Pharmaceutically acceptable formulations and (f) Polymorphic forms, are described, for example, in US Patent Application Publication number US 2007/0072904, the disclosure of which is hereby incorporated by reference in its entirety.

Administration

The methods and compounds will typically be used in therapy for human subjects. However, they may also be used to treat similar or identical indications in other animal subjects. In this context, the terms "subject", "animal subject", and the like refer to human and non-human vertebrates, e.g., mammals such as non-human primates, sports and commercial animals, e.g., bovines, equines, porcines, ovines, rodents, and pets e.g., canines and felines. A description of possible methods and routes of administration may be found, for example, in US Patent Application Publication number US 2007/0072904, the disclosure of which is hereby incorporated by reference in its entirety.

EXAMPLES

Examples related to the present invention are described below. In most cases, alternative techniques can be used. The examples are intended to be illustrative and are not limiting or restrictive to the scope of the invention.

Example 1

General Synthesis of Indole 3-Propionic Acid Derivatives

One method to prepare the indole precursor with 3-propionic acid side chain (VII) involves the use of indole with Meldram's acid to afford the propionic acid ester through a two step process in one pot as shown in Scheme I.

Scheme I:

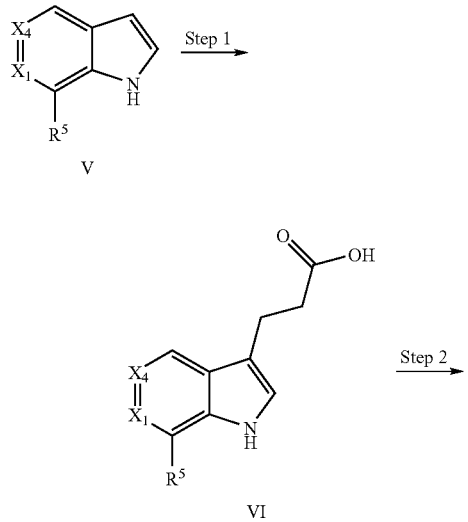

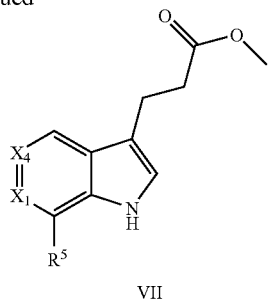

VII

Step 1—Preparation of the Indole-3-Propionic Acid (VI):

Into a microwave vessel, an indole derivative of formula V (1 equivalent, one of $X_1$ and $X_4$ is N or CH, the other is N or $CR^4$, $R^4$ is hydrogen, fluoro, chloro or optionally fluoro substituted methoxy, $R^5$ is hydrogen, fluoro, chloro, or optionally fluoro substituted $C_{1-3}$ alkyl) paraformaldehyde (1.1 equivalent), 2,2-dimethyl-1,3-dioxane-4,6-dione (1.1 equivalent), and triethylamine (1.1 equivalent) are dissolved in acetonitrile (2 ml/mmol). The reaction is heated at 150° C. for 3 minutes in a microwave reactor. The reaction is then diluted with acidified water (pH ~5 with acetic acid), and the aqueous layer was extracted with ethyl acetate. The organic layer is then washed with water, brine, and then dried over magnesium sulfate. Evaporation of solvent leads to a solid. The crude compound is then purified via flash chromatography with step gradient of 2, 4, and 6% methanol in chloroform on silica to obtain the desired compound VI as an oil.

Step 2—Preparation of the Indole-3-Propionic Acidmethyl Ester (VII):

Compound VI is stirred at ambient temperature with aqueous HCl (4M), with methanol and dioxane (1:1 equivalent) for 1 hour. The reaction mixture is then extracted with xylenes. The organic layer is evaporated, and compound VII is purified via flash chromatography on silica eluting with chloroform to obtain a solid.

The resulting propionic acid ester can be used to prepare the 1-sulfone substituted indole-3-propionic acid derivative XII in three steps as shown in Scheme II.

Scheme II

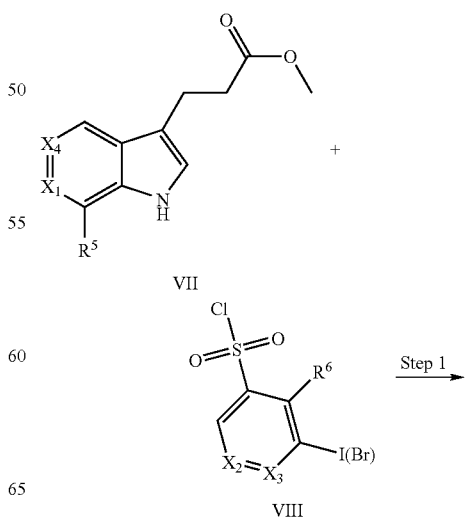

-continued

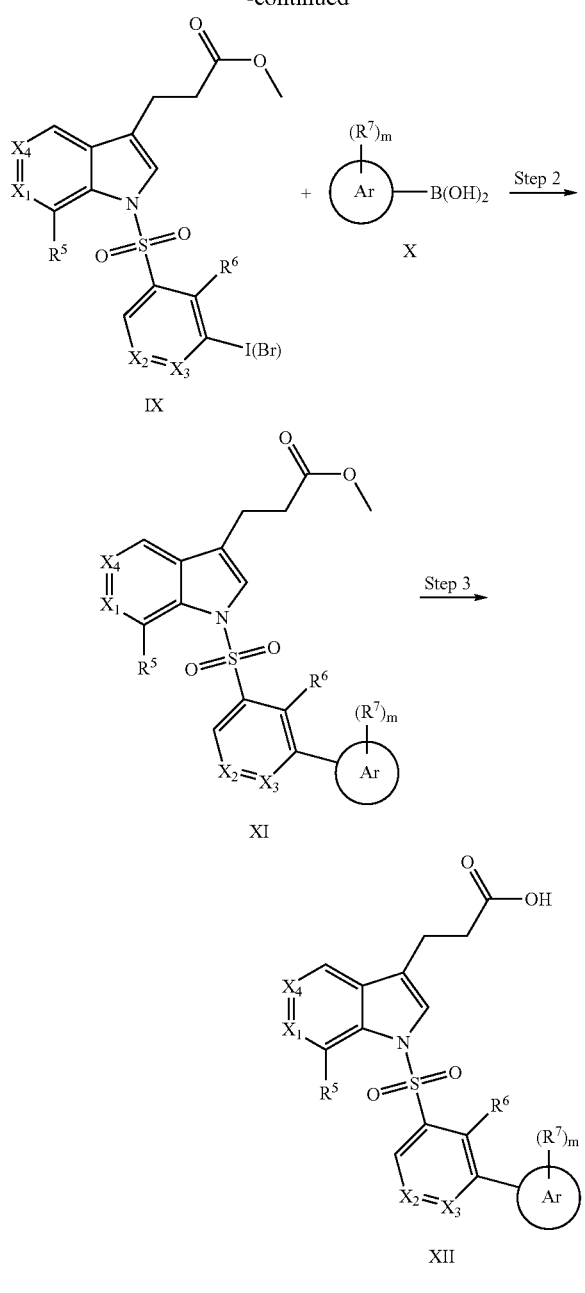

IX

XI

XII

Step 1—Preparation of Compound (IX):

Compound IX can be prepared by deprotonation of the indole nitrogen of compound VII with the use of a base, for example, sodium hydride, and coupling with a halogen (e.g. iodo or bromo) substituted aryl or heteroaryl sulfonyl chloride VIII ($X_2$, $X_3$ can be CH or N, $R^6$ is hydrogen, fluoro, chloro, or optionally fluoro substituted $C_{1-3}$ alkyl) in an inert solvent such as N,N-dimethylformamide.

Step 2—Preparation of Compound XI):

Compound XI can be prepared through metal catalyzed (such as palladium) biaryl coupling of a boronic acid X (Ar is aryl or heteroaryl, $R^7$ as defined, m is 0-5) with the halogen (e.g. iodo or bromo) substituted aromatic ring of IX, under basic conditions (i.e., Suzuki Cross Coupling, Muyaura and Suzuki, *Chem. Rev.* 1995, 95:2457).

Step 3—Preparation of Compound (XII).

The final step of the synthesis of compound XII involves the deprotection of the ester under saponification conditions with an aqueous hydroxide solution and an inert solvent such as tetrahydrofuran.

Alternatively, the fragment/substituent can be assembled before coupling to the indole propionic acid methyl ester core, as outlined in Scheme III.

Scheme III

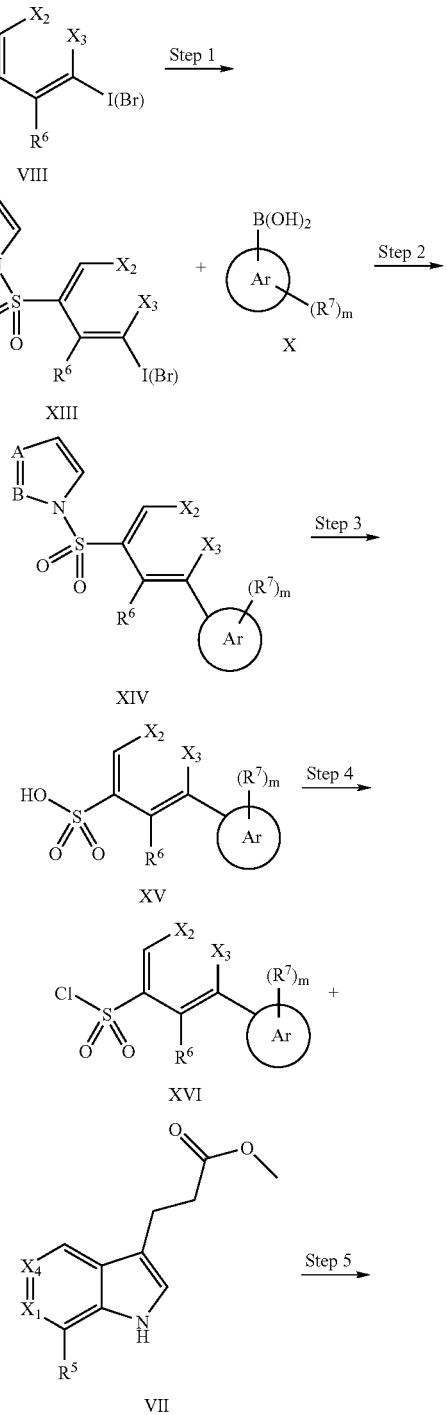

VIII

XIII

XIV

XV

XVI

VII

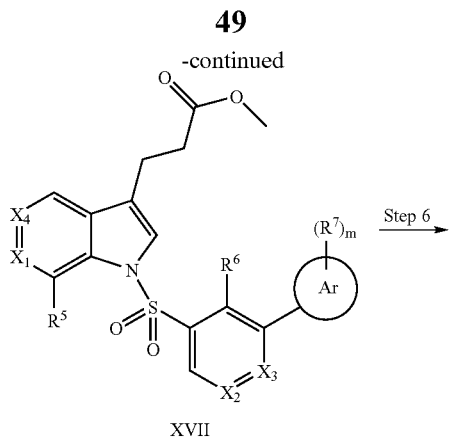

Step 1—Preparation of Compound (XIII).
Compound XIII can be prepared through coupling of sulfonyl chloride VIII ($X_2$, $X_3$ can be CH or N, $R^6$ is hydrogen, uoro, chloro, or optionally fluoro substituted $C_{1-3}$ alkyl) with a heterocycle such as an imidazole or pyrrole (where one of A or B is N and the other is CH) in an inert solvent such as dichloromethane with a base such as triethylamine or N,N-dimethylaminopyridine.

Step 2—Preparation of Compound (XIV):
Compound XIV can be prepared through metal catalyzed (such as palladium) biaryl coupling of a boronic acid X (Ar is aryl or heteroaryl, $R^7$ as defined, m is 0-5) with halogen (iodo or bromo) substituted aromatic ring of XIII, under basic conditions (i.e., Suzuki Cross Coupling).

Step 3—Preparation of Compound (XV).
Compound XV can be prepared through a basic hydrolysis of the sulfonamide of XIV with the use of a base, such as potassium hydroxide in an inert solvent such as methanol with heating.

Step 4—Preparation of Compound (XVI):
Compound XVI can be prepared through conversion of the acid functionality of XV with a reagent such as thionyl chloride or phosphorous pentachloride with catalytic amount of N,N-dimethylformamide.

Step 5—Preparation of Compound (XVII):
Compound XVII can be prepared by deprotonation of the indole nitrogen of compound VII (see Scheme I) with the use of a base, such as for example, sodium hydride, and coupling with a halogen substituted aryl sulfonyl chloride in an inert solvent such as N,N-dimethylformamide.

Step 6—Preparation of Compound (XVIII):
Compound XVIII can be prepared through deprotection of the alkyl ester of XVII through standard saponification conditions with a 1:1 ratio of an inert organic solvent, such as tetrahydrofuran and aqueous hydroxide solution (e.g., LiOH, NaOH, or KOH, 1M) at ambient condition.

Example 2

Synthesis of 3-[5-Fluoro-1-(2-methyl-4'-trifluoromethoxy-biphenyl-3-sulfonyl)-1H-indol-3-yl]-propionic acid P-0135

3-[5-Fluoro-1-(2-methyl-4'-trifluoromethoxy-biphenyl-3-sulfonyl)-1H-indol-3-yl]-propionic acid P-0135 was synthesized in five steps from 5-fluoro-1H-indole-3-carbaldehyde 1 as shown in Scheme 1.

Scheme 1

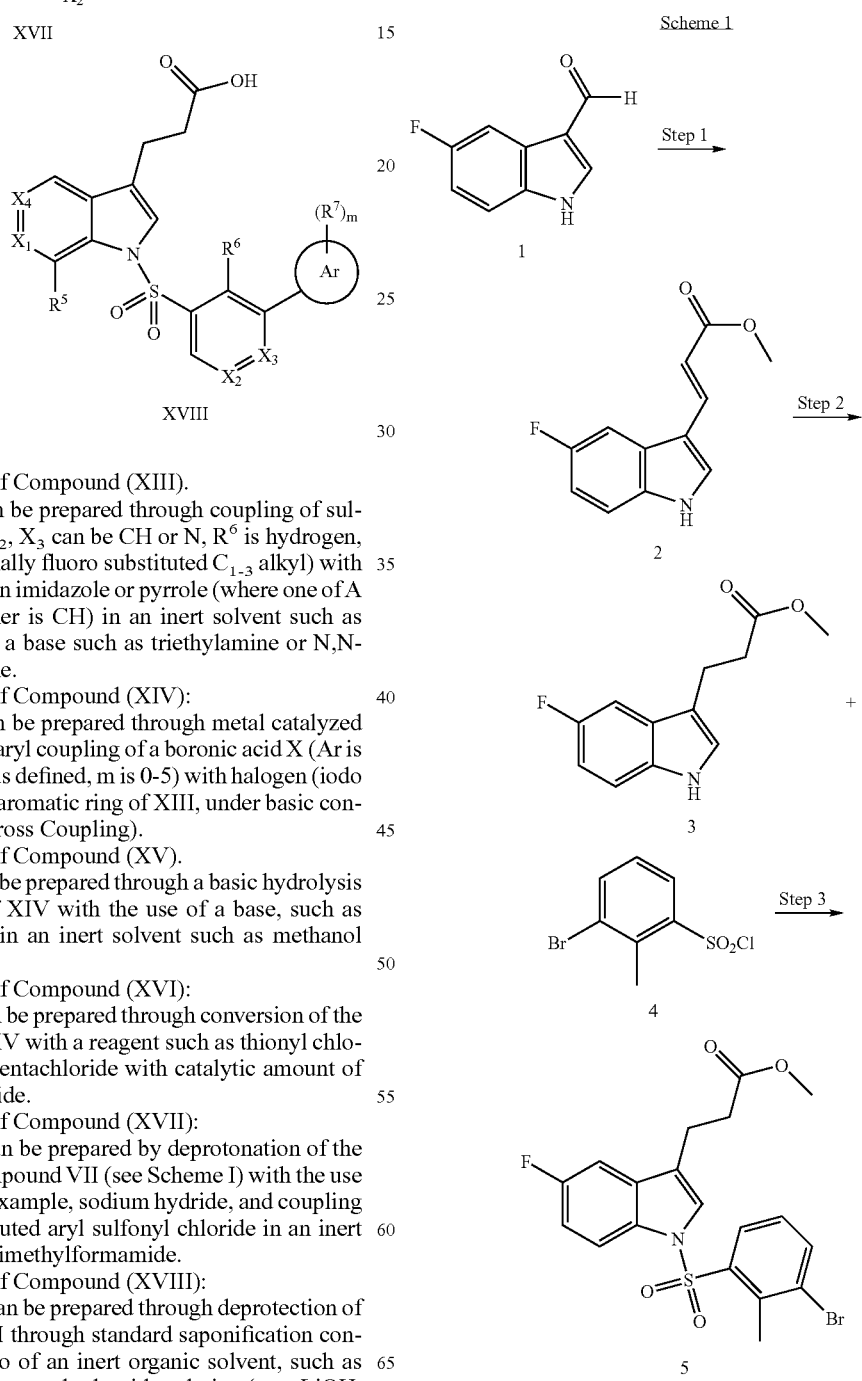

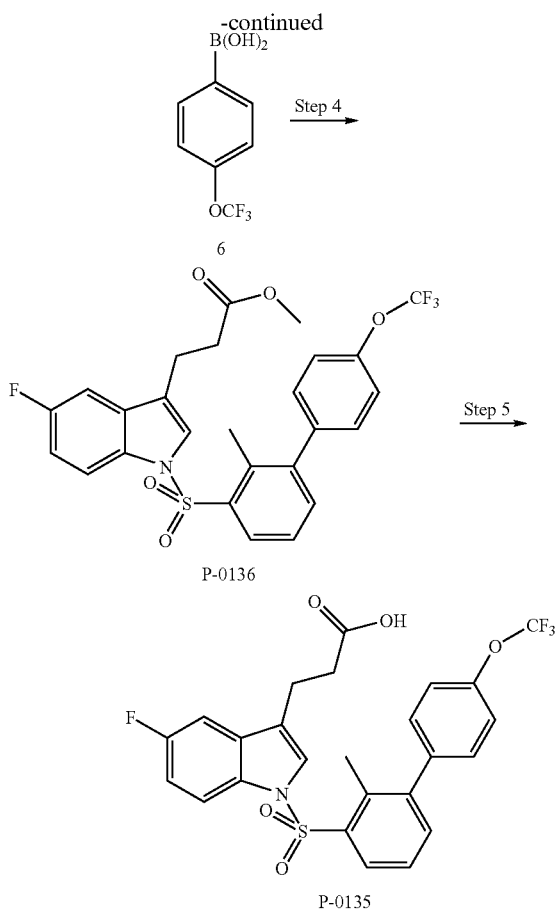

Step 1—Preparation of (E)-3-(5-fluoro-1H-indol-3-yl)-acrylic acid methyl ester (2).

In a flask, methyl diethylphosphonoacetate (2.745 mL, 0.01496 mol) in 5 mL of tetrahydrofuran was cooled to 0° C. and sodium hydride (394.83 mg, 0.016451 mol) was added. The mixture was stirred at 0° C. for 15 minutes and the solution was added dropwise to a stirring solution of 5-fluoro-1H-indole-3-carbaldehyde (1, 1.22 g, 0.00748 mol) in 26.69 mL of tetrahydrofuran at 0° C. The reaction was allowed to warm to room temperature for overnight. TLC analysis showed a mixture of starting material and product. An additional equivalent of methyl diethylphosphonoacetate was added at 0° C. and the mixture was allowed to warm to room temperature overnight. TLC analysis showed still unreacted starting material. Ethyl acetate was added and the organic layer was washed with saturated sodium bicarbonate. The organic layer was dried over MgSO$_4$, filtered and concentrated at reduced pressure to afford a brown oil, which was filtered over a plug of silica using 4:1 hexanes:ethyl acetate to remove unreacted phosphonate. Flash chromatography using a gradient of 0-25% hexanes:ethyl acetate over 35 minutes led to the isolation of the desired compound (0.530 g isolated, 32%). $^1$H NMR consistent with structure.

Step 2—Preparation of 3-(5-fluoro-1H-indol-3-yl)-propionic acid methyl ester (3):

Into a flask, (E)-3-(5-fluoro-1H-indol-3-yl)-acrylic acid methyl ester (2, 530.00 mg, 0.0024178 mol) was dissolved in 14.69 mL methanol. Palladium (10% on activated carbon, 25.73 mg, 0.0002418 mol) was added and the reaction was stirred under an atmosphere of hydrogen overnight. TLC analysis showed complete conversion to a new product. The mixture was filtered and concentrated under reduced pressure to provide the desired compound (3, 500 mg, 93.4%). $^1$H NMR consistent with desired compound. MS(ESI) [M+H$^+$]$^+$= 222.0.

Step 3—Preparation of 3-[1-(3-Bromo-2-methyl-benzenesulfonyl)-5-fluoro-1H-indol-3-yl]-propionic acid methyl ester (5):

Into a flask, 3-(5-fluoro-1H-indol-3-yl)-propionic acid methyl ester (3, 530.000 mg, 2.39572E-3 mol), 3-bromo-2-methyl-benzene sulfonyl chloride (4, 710.33 mg, 0.0026353 mol), 62.35 mL methylene chloride, 17 mL 50% KOH and a catalytic amount of tetra-n-butyl ammonium hydrogen sulfate were combined and stirred at room temperature for 48 hours. The organic layer was washed with saturated sodium bicarbonate, dried over MgSO$_4$ and filtered. The organic layer was concentrated at reduced pressure to afford a tannish solid. Purification by flash chromatography using a gradient of 0-25% ethyl acetate in hexanes over 35 minutes yielded the desired compound (5, 650 mg, 59.72%). $^1$H NMR consistent with desired compound. MS(ESI) [M+H$^+$]$^+$=454.0, 456.0.

Step 4—Preparation of 3-[5-Fluoro-1-(2-methyl-4'-trifluoromethoxy-biphenyl-3-sulfonyl)-1H-indol-3-yl]-propionic acid methyl ester (P-0136):

Into a 50 mL oven dried round bottom flask, 3-[1-(3-Bromo-2-methyl-benzenesulfonyl)-5-fluoro-1H-indol-3-yl]-propionic acid methyl ester (5, 52.062 mg, 1.1459E-4 mol), 4-trifluoromethoxy-phenyl boronic acid (6, 35.397 mg, 1.7189E-4 mol) and Tetrakis(triphenylphosphine)palladium (0) (13.24 mg, 1.146E-5 mol) were combined. A volume of 0.3 mL of 1N K$_2$CO$_3$ was added and the reaction was heated to 110° C. for 90 minutes. TLC analysis showed co-elution of product and starting material. Ethyl acetate was added and washed 5× with saturated sodium bicarbonate. The organic layer was dried over MgSO$_4$, filtered and concentrated at reduced pressure. The crude material was purified using prep plate chromatography (7:3 hexane:ethyl acetate) to provide the desired compound (40 mg isolated, 65% yield). $^1$H NMR consistent with compound structure. MS(ESI) [M+H$^+$]$^+$= 536.1 (calculated 535.51).

Step 5—Synthesis of 3-[5-Fluoro-1-(2-methyl-4'-trifluoromethoxy-biphenyl-3-sulfonyl)-1H-indol-3-yl]-propionic acid (P-0135):

To a solution of 3-[5-Fluoro-1-(2-methyl-4'-trifluoromethoxy-biphenyl-3-sulfonyl)-1H-indol-3-yl]-propionic acid methyl ester (P-0136, 20.000 mg, 3.734SE-5 mol), lithium hydroxide (1M, 0.25 mL) and tetrahydrofuran (1.000 mL, 0.01233 mol) were added to a vial and the reaction was stirred overnight. TLC showed product formation with no unreacted starting material remaining. Ethyl acetate was added and the mixture was acidified with 1M HCl. The organic layer was dried over MgSO$_4$, filtered and concentrated at reduced pressure to provide a white solid (17 mg isolated, 87%). $^1$H NMR consistent with structure. MS(ESI) [M−H$^+$]$^−$=520.0 (calculated 521.49).

The following compounds were prepared following the protocol of Scheme 1, optionally replacing 5-fluoro-1H-indole-3-carbaldehyde 1 with an appropriate 1H-indole-3-carbaldehyde compound in Step 1, and/or optionally replacing the 3-bromo-2-methyl-benzenesulfonyl chloride 4 with an appropriate 3-bromo-benzenesulfonyl chloride in Step 3 and/or optionally replacing 4-trifluoromethoxy-phenyl boronic acid 6 with an appropriate boronic acid in Step 4. The experimental mass is provided after each compound:

3-[5-Chloro-1-(4'-trifluoromethyl-biphenyl-3-sulfonyl)-1H-indol-3-yl]-propionic acid methyl ester (P-0001, MS(ESI) [M+H$^+$]$^+$=522.6), 3-[5-Chloro-1-(4'-trifluoromethyl-biphenyl-3-sulfonyl)-1H-indol-3-yl]-propionic acid (P-0002, MS(ESI) [M+H⁻]⁺=507.5), 3-[5-Chloro-1-(3'-chloro-biphenyl-3-sulfonyl)-1H-indol-3-yl]-propionic acid (P-0003, MS(ESI) [M+H⁺]⁺=522.3 (+DMSO)), 3-[5-Chloro-1-(4'-chloro-biphenyl-3-sulfonyl)-1H-indol-3-yl]-propionic acid (P-0004, MS(ESI) [M+H⁺]⁺=551.9 (+DMSO)), 3-[5-Chloro-1-(4'-methoxy-biphenyl-3-sulfonyl)-1H-indol-3-yl]-propionic acid (P-0005, MS(ESI) [M+H⁺]⁺=486.3), 3-[5-Chloro-1-(4'-fluoro-biphenyl-3-sulfonyl)-1H-indol-3-yl]-propionic acid (P-0006, MS(ESI) [M+H⁺]⁺=458.3), 3-[5-Chloro-1-(2',4'-difluoro-biphenyl-3-sulfonyl)-1H-indol-3-yl]-propionic acid (P-007, MS(ESI) [M+H⁺]⁺=476,3), 3-[5-Chloro-1-(3'-chloro-4'-fluoro-biphenyl-3-sulfonyl)-1H-indol-3-yl]-propionic acid (P-0008, MS(ESI) [M+H⁺]⁺=570.0 (+DMSO)), 3-[5-Chloro-1-(4'-ethoxy-biphenyl-3-sulfonyl)-1H-indol-3-yl]-propionic acid (P-0009, MS(ESI) [M+H⁺]⁺=484.3), 3-[5-Chloro-1-(3'-fluoro-biphenyl-3-sulfonyl)-1H-indol-3-yl]-propionic acid (P-0010, MS(ESI) [M+H⁺]⁺=457.9), 3-[5-Chloro-1-(2'-fluoro-biphenyl-3-sulfonyl)-1H-indol-3-yl]-propionic acid (P-0011, MS(ESI) [M+H⁺]⁺=457.9), 3-[5-Chloro-1-(3'-trifluoromethoxy-biphenyl-3-sulfonyl)-1H-indol-3-yl]-propionic acid (P-0012, MS(ESI) [M+H⁺]+³⁰=524.3), 3-[5-Chloro-1-(4'-trifluoromethoxy-biphenyl-3-sulfonyl)-1H-indol-3-yl]-propionic acid (P-0013, MS(ESI) [M+H⁺]⁺=523.1), 3-[5-Chloro-1-(3'-trifluoromethyl-biphenyl-3-sulfonyl)-1H-indol-3-yl]-propionic acid (P-0014, MS(ESI) [M+H⁺]⁺=500.3), 3-[1-(4'-Benzyloxy-2'-fluoro-biphenyl-3-sulfonyl)-5-chloro-1H-indol-3-yl]-propionic acid (P-0015, MS(ESI) [M+H⁺]⁺=564.0), 3-{5-Chloro-1-[3-(6-methoxy-pyridin-3-yl)-benzenesulfonyl]-1H-indol-3yl}-propionic acid (P-0016, MS(ESI) [M+H⁺]⁺=503.9), 3-[5-Chloro-1-(3'-fluoro-4'-methyl-biphenyl-3-sulfonyl)-1H-indol-3-yl]-propionic acid (P-0017, MS(ESI) [M+H⁺]⁺=471.5), 3-[5-Chloro-1-(3'-fluoro-4'-methoxy-biphenyl-3-sulfonyl)-1H-indol-3-yl]-propionic acid (P-0018, MS(ESI) [M+H⁺]⁺=488.3), 3-{5-Chloro-1-[3-(2-methoxy-pyrimidin-5-yl)-benzenesulfonyl]-1H-indol-3-yl}-propionic acid (P-0019, MS(ESI) [M+H⁺]⁺=472.3), 3-{5-Chloro-1-[3-(2,4-dimethoxy-pyrimidin-5-yl)-benzenesulfonyl]-1H-indol-3-yl}-propionic acid (P-0020, MS(ESI) [M+H⁺]⁺=501.9), 3-[5-Chloro-1-(2'-fluoro-4'-trifluoromethyl-biphenyl-3-sulfonyl)-1H-indol-3-yl]-propionic acid (P-0021, MS(ESI) [M+H⁺]⁺=604.4 (+DMSO)), 3-(5-Chloro-1-{3-[1-(3-methyl-butyl)-1H-pyrazol-4-yl]-benzenesulfonyl}-1H-indol-3yl)-propionic acid (P-0022, MS(ESI) [M+H⁺]⁺=470.3), 3-{5-Chloro-1-[3-(1-isobutyl-1H-pyrazol-4-yl)-benzenesulfonyl]-1H-indol-3-yl}-propionic acid (P-0023, MS(ESI) [M+H⁺]⁺=486.3), 3-[5-Chloro-1-(2'-fluoro-4'-methoxy-biphenyl-3-sulfonyl)-1H-indol-3-yl]-propionic acid (P-0024, MS(ESI) [M+H⁺]⁺=488.3), 3-[5-Chloro-1-(4'-chloro-2'-fluoro-biphenyl-3-sulfonyl)-1H-indol-3-yl]-propionic acid (P-0025, MS(ESI) [M+H⁺]⁺=492.3), 3-[1-(3'-Chloro-biphenyl-3-sulfonyl)-5-fluoro-1H-indol-3-yl]-propionic acid (P-0026, MS(ESI) [M+H⁺]⁺=458.3), 3-[1-(4'-Chloro-biphenyl-3-sulfonyl)-5-fluoro-1H-indol-3-yl]-propionic acid (P-0027, MS(ESI) [M+H⁺]⁺=457.9), 3-[5-Fluoro-1-(4'-methoxy-biphenyl-3-sulfonyl)-1H-indol-3-yl]-propionic acid (P-0028, MS(ESI) [M+H⁺]⁺=453.9), 3-[5-Fluoro-1-(4'-fluoro-biphenyl-3-sulfonyl)-1H-indol-3-yl]-propionic acid (P-0029, MS(ESI) [M+H⁺]⁺=442.3), 3-[1-(3'-Chloro-4'-fluoro-biphenyl-3-sulfonyl)-5-fluoro-1H-indol-3-yl]-propionic acid (P-0030, MS(ESI) [M+H⁺]⁺=475.9), 3-[5-Fluoro-1-(3'-fluoro-biphenyl-3-sulfonyl)-1H-indol-3-yl]-propionic acid (P-0031, MS(ESI) [M+H⁺]⁺=441.9), 3-[5-Fluoro-1-(2'-fluoro-biphenyl-3-sulfonyl)-1H-indol-3-yl]-propionic acid (P-0032, MS(ESI) [M+H⁺]⁺=442.3), 3-[5-Fluoro-1-(3'-trifluoromethoxy-biphenyl-3-sulfonyl)-1H-indol-3-yl]-propionic acid (P-0033, MS(ESI) [M+H⁺]⁺=508.3), 3-[5-Fluoro-1-(4'-trifluoromethoxy-biphenyl-3-sulfonyl)-1H-indol-3-yl]-propionic acid (P-0034, MS(ESI) [M+H⁺]⁺=507.9), 3-[5-Fluoro-1-(4'-trifluoromethyl-biphenyl-3-sulfonyl)-1H-indol-3-yl]-propionic acid (P-0035, MS(ESI) [M+H⁺]⁺=487.9), 3-[1-(4'-Benzyloxy-2'-fluoro-biphenyl-3-sulfonyl)-5-fluoro-1H-indol-3-yl]-propionic acid (P-0036, MS(ESI) [M+H⁺]⁺=547.9), 3-{5-Fluoro-1-[3-(6-methoxy-pyridin-3-yl)-benzenesulfonyl]-1H-indol-3-yl}-propionic acid (P-00,37, MS(ESI) [M+H⁺]⁺=455.1), 3-[5-Fluoro-1-(3'-fluoro-4'-methoxy-biphenyl-3-sulfonyl)-1H-indol-3-yl]-propionic acid (P-0038, MS(ESI) [M+H⁺]⁺=472.3), 3-{5-Fluoro-1-[3-(2-methoxy-pyrimidin-5-yl)-benzenesulfonyl]-1H-indol-3-yl}-propionic acid (P-0039, MS(ESI) [M+H⁺]⁺=456.3), 3-{1-[3-(2,4-Dimethoxy-pyrimidin-5-yl)-benzenesulfonyl]-5-fluoro-1H-indol-3-yl}-propionic acid (P-0040, MS(ESI) [M+H⁺]⁺=471.1), 3-(5-Fluoro-1-{3-[1-(3-methyl-butyl)-1H-pyrazol-4-yl]-benzenesulfonyl}-1H-indol-3-yl)-propionic acid (P-0041, MS(ESI) [M+H⁺]⁺=484.3), 3-{5-Fluoro-1-[3-(1-isobutyl-1H-pyrazol-4-yl)-benzenesulfonyl]-1H-indol-3-yl}-propionic acid (P-0042, MS(ESI) [M+H⁺]⁺=469.9), 3-[5-Fluoro-1-(2'-fluoro4'-methoxy-biphenyl-3-sulfonyl)-1H-indol-3-yl]-propionic acid (P-0043, MS(ESI) [M+H⁺]⁺=472.3), 3-[1-(4'-Chloro-2'-fluoro-biphenyl-3-sulfonyl)-5-fluoro-1H-indol-3-yl]-propionic acid (P-0044, MS(ESI) [M+H⁺]⁺=475.5), 3-[1-(3'-Chloro-biphenyl-3-sulfonyl)-5-methoxy-1H-indol-3-yl]-propionic acid (P-0045, MS(ESI) [M+H⁺]⁺=470.3), 3-[1-(4'-Chloro-biphenyl-3-sulfonyl)-5-methoxy-1H-indol-3-yl]-propionic acid (P-0046, MS(ESI) [M+H$^+$]$^+$=470.3), 3-[5-Methoxy-1-(4'-methoxy-biphenyl-3-sulfonyl)-1H-indol-3-yl]-propionic acid (P-0047, MS(ESI) [M+H$^+$]$^+$= 466.3), 3-[1-(4'-Fluoro-biphenyl-3-sulfonyl)-5-methoxy-1H-indol-3-yl]-propionic acid (P-0048, MS(ESI) [M+H$^+$]$^+$= 453.9), 3-[1-(2',4'-Difluoro-biphenyl-3-sulfonyl)-5-methoxy-1H-indol-3-yl]-propionic acid (P-0049, MS(ESI) [M+H$^+$]$^+$= 472.3), 3-[1-(3'-Chloro-4'-fluoro-biphenyl-3-sulfonyl)-5-methoxy-1H-indol-3-yl]-propionic acid (P-0050, MS(ESI) [M+H$^+$]$^+$=479.9), 3-[1-(4'-Ethoxy-biphenyl-3-sulfonyl)-5-methoxy-1H-indol-3-yl]-propionic acid (P-0051, MS(ESI) [M+H$^+$]$^+$= 507.9), 3-[1-(3'-Fluoro-biphenyl-3-sulfonyl)-5-methoxy-1H-indol-3-yl]-propionic acid (P-0052, MS(ESI) [M+H$^+$]$^+$= 453.9), 3-[1-(2'-Fluoro-biphenyl-3-sulfonyl)-5-methoxy-1-indol-3-yl]-propionic acid (P-0053, MS(ESI) [M+H$^+$]$^+$= 453.9), 3-[5N-Methoxy-1-(3'-trifluoromethoxy-biphenyl-3-sulfonyl)-1H-indol-3-yl]-propionic acid (P-0054, MS(ESI) [M+H $^+$]$^+$=520.3), 3-[5-Methoxy-1-(4'-trifluoromethoxy-biphenyl-3-sulfonyl)-1H-indol-3-yl]-propionic acid (P-0055, MS(ESI) [M+$^+$H]$^+$=520.3), 3-[5-Methoxy-1-(3'-trifluoromethyl-biphenyl-3-sulfonyl)-1H-indol-3-yl]-propionic acid (P-0056, MS(ESI) [M+H$^+$]$^+$=503.9), 3-[1-(4'-Benzyloxy-2-fluoro-biphenyl-3-sulfonyl)-5-methoxy-1H-indol-3-yl]-propionic acid (P-0057, MS(ESI) [M+H$^+$]$^+$=560.0), 3-{5-Methoxy-1-[3-(6-methoxy-pyridin-3-yl)-benzenesulfonyl]-1H-indol-3-yl}-propionic acid (P-0058, MS(ESI) [M+H$^+$]$^+$=467.1), 3-[1-(3'-Fluoro-4'-methyl-biphenyl-3-sulfonyl)-5-methoxy-1H-indol-3-yl]-propionic acid (P-0059, MS(ESI) [M+H$^+$]$^+$=467.9), 3-[1-(3'-Fluoro-4'-methoxy-biphenyl-3-sulfonyl)-5-methoxy-1H-indol-3-yl]-propionic acid (P-0060, MS(ESI) [M+H$^+$]$^+$=483.9), 3-{5-Methoxy-1-[3-(2-methoxy-pyrimidin-5-yl)-benzenesulfonyl]-1H-indol-3-yl}-propionic acid (P-0061, MS(ESI) [M+H$^+$]$^+$=468.3), 3-{1-[3-(2,4-Dimethoxy-pyrimidin-5-yl)-benzenesulfonyl]-5-methoxy-1H-indol-3-yl}-propionic acid (P-0062, MS(ESI) [M+H$^+$]$^+$=498.3), 3-[1-(2'-Fluoro-4'-trifluoromethyl-biphenyl-3-sulfonyl)-5-methoxy-1H-indol-3-yl]-propionic acid (P-0063, MS(ESI) [M+H$^+$]$^+$=522.3), 3-(5-Methoxy-1-{3-[1-(3-methyl-butyl)-1H-pyrazol-4-yl]-benzenesulfonyl}-1H-indol-3yl)-propionic acid (P-0064, MS(ESI) [M+H$^+$]$^+$=496.3), 3-{1-[3-(1-Isobutyl-1H-pyrazol-4-yl)-benzenesulfonyl]-5-methoxy-1H-indol-3-yl}-propionic acid (P-0065, MS(ESI) [M+H$^+$]$^+$=482.3), 3-[1-(2'-Fluoro-4'-methoxy-biphenyl-3-sulfonyl)-5-methoxy-1H-indol-3-yl]-propionic acid (P-0066, MS(ESI) [M+H$^+$]$^+$=483.9), 3-[1-(4'-Chloro-2'-fluoro-biphenyl-3-sulfonyl)-5-methoxy-1H-indol-3-yl]-propionic acid (P-0067, MS(ESI) [M+H$^+$]$^+$=488.3), 3-[1-(2',4'-Difluoro-biphenyl-3-sulfonyl)-5-fluoro-1H-indol-3-yl]-propionic acid (P-0068, MS(ESI) [M+H$^+$]$^+$=460.3), 3-[5-Fluoro-1-(2'-fluoro-4'-trifluoromethyl-biphenyl-3-sulfonyl)-1H-indol-3-yl]-propionic acid (P-0069, MS(ESI) [M+H$^+$]$^+$=510.3), 3-[1-(3'-Chloro-biphenyl-3-sulfonyl)-1H-indol-3-yl]-propionic acid (P-0070, MS(ESI) [M+H$^+$]$^+$=440.3), 3-[1-(4'-Chloro-biphenyl-3-sulfonyl)-1H-indol-3-yl]-propionic acid (P-0071, MS(ESI) [M+H$^+$]$^+$=439.9), 3-[1-(4'-Methoxy-biphenyl-3-sulfonyl)-1H-indol-3-yl]-propionic acid (P-0072, MS(ESI) [M+H$^+$]$^+$=436.3), 3-[1-(4'-Fluoro-biphenyl-3-sulfonyl)-1H-indol-3-yl]-propionic acid (P-0073, MS(ESI) [M+H$^+$]$^+$=424.3), 3-[1-(2',4'-Difluoro-biphenyl-3-sulfonyl)-1H-indol-3-yl]-propionic acid (P-0074, MS(ESI) [M+H$^+$]$^+$=442.3), 3-[1-(3'-Chloro-4'-fluoro-biphenyl-3-sulfonyl)-1H-indol-3-yl]-propionic acid (P-0075, MS(ESI) [M+H$^+$]$^+$= 458.3), 3-[1-(4'-Ethoxy-biphenyl-3-sulfonyl)-1H-indol-3-yl]-propionic acid (P-0076, MS(ESI) [M+H$^+$]$^+$=450.3), 3-[1-(3'-Fluoro-biphenyl-3-sulfonyl)-1H-indol-3-yl]-propionic acid (P-0077, MS(ESI) [M+H$^+$]$^+$=424.3), 3-[1-(2'-Fluoro-biphenyl-3-sulfonyl)-1H-indol-3-yl]-propionic acid (P-0078, MS(ESI) [M+H$^+$]$^+$=423.9), 3-[1-(3'-Trifluoromethoxy-biphenyl-3-sulfonyl)-1H-indol-3-yl]-propionic acid (P-0079, MS(ESI) [M+H$^+$]$^+$= 490.3), 3-[1-(4'-Trifluoromethoxy-biphenyl-3-sulfonyl)-1H-indol-3-yl]-propionic acid (P-0080, MS(ESI) [M+H$^+$]$^+$= 489.9), 3-[1-(3'-Trifluoromethyl-biphenyl-3-sulfonyl)-1H-indol-3-yl]-propionic acid (P-0081, MS(ESI) [M+H$^+$]$^+$= 474.3), 3-[1-(4'-Benzyloxy-2'-fluoro-biphenyl-3-sulfonyl)-1H-indol-3-yl]-propionic acid (P-0082, MS(ESI) [M+H$^+$]$^+$= 529.9), 3-{1-[3-(6-Methoxy-pyridin-3-yl)-benzenesulfonyl]-1H-indol-3-yl}-propionic acid (P-0083, MS(ESI) [M+H$^+$]$^+$= 473.9), 3-[1-(3'-Fluoro-4'-methyl-biphenyl-3-sulfonyl)-1H-indol-3-yl]-propionic acid (P-0084, MS(ESI) [M+H$^+$]$^+$= 437.9), 3-[1-(3'-Fluoro-4'-methoxy-biphenyl-3-sulfonyl)-1H-indol-3-yl]-propionic acid (P-0085, MS(ESI) [M+H$^+$]$^+$= 453.9), 3 -{1-[3-(2,4-Dimethoxy-pyrimidin-5-yl)-benzenesulfonyl]-1H-indol-3-yl}-propionic acid (P-0086, MS(ESI) [M+H$^+$]$^+$=468.3), 3-[1-(2'-Fluoro-4'-trifluoromethyl-biphenyl-3-sulfonyl)-1H-indol-3-yl]-propionic acid (P-0087, MS(ESI) [M+H$^+$]$^+$=492.3), 3-[1-(2'-Fluoro-4'-methoxy-biphenyl-3-sulfonyl)-1H-indol-3-yl]-propionic acid (P-0088, MS(ESI) [M+H$^+$]$^+$= 453.9), 3-[1-(4'-Chloro-2'-fluoro-biphenyl-3-sulfonyl)-1H-indol-3-yl]-propionic acid (P-0089, MS(ESI) [M+H$^+$]$^+$= 458.3), 3-(1-{3-[1-(3-Methyl-butyl)-1H-pyrazol-4-yl]-benzenesulfonyl}-1H-indol-3-yl)-propionic acid (P-0090, MS(ESI) [M+H$^+$]$^+$=466.3), 3-{1-[3-(1-Isobutyl-1H-pyrazol-4-yl)-benzenesulfonyl]-1H-indol-3-yl}-propionic acid (P-0091, MS(ESI) [M+H$^+$]$^+$=451.9), 3-[1-(Biphenyl-3-sulfonyl)-1H-indol-3-yl]-propionic acid (P-0092, MS(ESI) [M+H$^+$]=406.3), 3-[1-(2',4'-Dichloro-biphenyl-3-sulfonyl)-1H-indol-3-yl]-propionic acid (P-0093, MS (ESI) [M+H$^+$]$^+$=551.9 (+DMSO)), 3-[1-(4'-Fluoro-2'-methyl-biphenyl-3-sulfonyl)-1H-indol-3-yl]-propionic acid (P-0094, MS(ESI) [M+H$^+$]$^+$=437.9), 3-[1-(2',3'-Dichloro-biphenyl-3-sulfonyl)-1H-indol-3-yl]-propionic acid (P-0095, MS(ESI) [M+H$^+$]$^+$=473.9), 3-[1-(2',3'-Difluoro-biphenyl-3-sulfonyl)-1H-indol-3-yl]-propionic acid (P-0096, MS(ESI) [M+H$^+$]$^+$=441.9), 3-[1-(4'-Chloro-2'-methyl-biphenyl-3-sulfonyl)-1H-indol-3-yl]-propionic acid (P-0097, MS(ESI) [M+H$^+$]$^+$=453.9), 3-[1-(2'-Chloro-4'-ethoxy-biphenyl-3-sulfonyl)-1H-indol-3-yl]-propionic acid (P-0098, MS(ESI) [M+H$^+$]$^+$=483.9), 3-[1-(2'-Chloro-3'-fluoro-biphenyl-3-sulfonyl)-1H-indol-3-yl]-propionic acid (P-0099, MS(ESI) [M+H$^+$]$^+$=457.9), 3-[1-(2'-Chloro-4'-fluoro-biphenyl-3-sulfonyl)-1H-indol-3-yl]-propionic acid (P-0100, MS(ESI) [M+H$^+$]$^+$=458.3), 3-[1-(4-Ethoxy-2'-methyl-biphenyl-3-sulfonyl)-1H-indol-3-yl]-propionic acid (P-0101, MS(ESI) [M+H$^+$]$^+$=463.9), 3-[1-(Biphenyl-3-sulfonyl)-5-fluoro-1H-indol-3-yl]-propionic acid (P-0102, MS(ESI) [M+H$^+$]$^+$=423.9), 3-[1-(2',4'-Dichloro-biphenyl-3-sulfonyl)-5-fluoro-1H-indol-3-yl]-propionic acid (P-0103, MS(ESI) [M+H$^+$]$^+$=570.0 (+DMSO)), 3-[5-Fluoro-1-(4'-fluoro-2'-methyl-biphenyl-3-sulfonyl)-1H-indol-3-yl]-propionic acid (P-0104, MS(ESI) [M+H$^+$]$^+$=455.9), 3-[1-(2',3'-Dichloro-biphenyl-3-sulfonyl)-5-fluoro-1H-indol-3-yl]-propionic acid (P-0105, MS(ESI) [M+H$^+$]$^+$=492.3), 3-[1-(2',3'-Difluoro-biphenyl-3-sulfonyl)-5-fluoro-1H-indol-3-yl]-propionic acid (P-0106, MS(ESI) [M+H$^+$]$^+$=459.9), 3-[1-(2'-Chloro-4'-trifluoromethyl-biphenyl-3-sulfonyl)-5-fluoro -1H-indol-3-yl]-propionic acid (P-0107, MS(ESI) [M+H$^+$]$^+$=603.6 (+DMSO)), 3-[1-(4'-Chloro-2'-methyl-biphenyl-3-sulfonyl)-5-fluoro-1H-indol-3-yl]-propionic acid (P-0108, MS(ESI) [M+H$^+$]$^+$=472.3), 3-[1-(2'-Chloro-4'-ethoxy-biphenyl-3-sulfonyl)-5-fluoro-1H-indol-3-yl]-propionic acid (P-0109, MS(ESI) [M+H$^+$]$^+$=501.9), 3-[1-(2'-Chloro-3'-fluoro-biphenyl-3sulfonyl)-5-fluoro-1H-indol-3-yl]-propionic acid (P-0110, MS(ESI) [M+H$^+$]$^+$=476.3), 3-[1-(2'-Chloro-4'-fluoro-biphenyl-3-sulfonyl)-5-fluoro-1H-indol-3-yl]-propionic acid (P-0111, MS(ESI) [M+H$^+$]$^+$=476.7), 3-[1-(4'-Ethoxy-2'-methyl-biphenyl-3-sulfonyl)-5-fluoro-1H-indol-3-yl]-propionic acid (P-0112, MS(ESI) [M+H$^+$]$^+$=482.3), 3-[1-(Biphenyl-3-sulfonyl)-5-methoxy-1H-indol-3-yl]-propionic acid (P-0113, MS(ESI) [M+H$^+$]$^+$=436.6), 3-[1-(2',4'-Dichloro-biphenyl-3-sulfonyl)-5-methoxy-1H-indol-3-yl]-propionic acid (P-0114, MS(ESI) [M+H$^+$]$^+$=503.9), 3-[1-(4'-Fluoro-2'-methyl-biphenyl-3-sulfonyl)-5-methoxy-1H-indol-3-yl]-propionic acid (P-0115, MS(ESI) [M+H$^+$]$^+$=468.3), 3-[1-(2',3'-Dichloro-biphenyl-3-sulfonyl)-5-methoxy-1-indol-3-yl]-propionic acid (P-0116, MS(ESI) [M+H$^+$]$^+$=503.9), 3-[1-(2',3'-Difluoro-biphenyl-3-sulfonyl)-5-methoxy-1H-indol-3-yl]-propionic acid (P-0117, MS(ESI) [M+H$^+$]$^+$=472.3), 3-[1-(2'-Chloro-4'-trifluoromethyl-biphenyl-3-sulfonyl)-5-methoxy-1-indol-3-yl]-propionic acid (P-0118, MS(ESI) [M+H$^+$]$^+$=537.9), 3-[1-(4'-Chloro-2'-methyl-biphenyl-3-sulfonyl)-5-methoxy-1H-indol-3-yl]-propionic acid (P-0119, MS(ESI) [M+H$^+$]$^+$=483.9), 3-[1-(2'-Chloro-4'-ethoxy-biphenyl-3-sulfonyl)-5-methoxy-1H-indol-3-yl]-propionic acid (P-0120, MS(ESI) [M+H$^+$]$^+$=514.3), 3-[1-(2'-Chloro-3'-fluoro-biphenyl-3-sulfonyl)-5-methoxy-1-indol-3-yl]-propionic acid (P-0121, MS(ESI) [M+H$^+$]$^+$=487.9), 3-[1-(2'-Chloro-4'-fluoro-biphenyl-3-sulfonyl)-5-methoxy-1H-indol-3-yl]-propionic acid (P-0122, MS(ESI) [M+H$^+$]$^+$=487.9), 3-[1-(4'-Ethoxy-2'-methyl-biphenyl-3-sulfonyl)-5-methoxy-1H-indol-3-yl]-propionic acid (P-0123, MS(ESI) [M+H$^+$]$^+$=494.3), 3-[1-(Biphenyl-3-sulfonyl)-5-chloro-1H-indol-3-yl]-propionic acid (P-0124, MS(ESI) [M+H$^+$]$^+$=517.9 (+DMSO)), 3-[5-Chloro-1-(2',4'-dichloro-biphenyl-3-sulfonyl)-1H-indol-3-yl]-propionic acid (P-0125, MS(ESI) [M+H$^+$]$^+$=586.0 (+DMSO)), 3-[5-Chloro-1-(4'-fluoro-2'-methyl-biphenyl-3-sulfonyl)-1H-indol-3-yl]-propionic acid (P-0126, MS(ESI) [M+H$^+$]$^+$=550.3 (+DMSO)), 3-[5-Chloro-1-(2',3'-dichloro-biphenyl-3-sulfonyl)-1H-indol-3-yl]-propionic acid (P-0127, MS(ESI) [M+H$^+$]$^+$=586.0 (+DMSO)), 3-[5-Chloro-1-(2',3'-difluoro-biphenyl-3-sulfonyl)-1H-indol-3-yl]-propionic acid (P-0128, MS(ESI) [M+H$^+$]$^+$=554.0 (+DMSO)), 3-[5-Chloro-1-(2'-chloro-4'-trifluoromethyl-biphenyl-3-sulfonyl)-1H-indol-3-yl]-propionic acid (P-0129, MS(ESI) [M+H$^+$]$^+$=620.4 (+DMSO)), 3-[5-Chloro-1-(4'-chloro-2'-methyl-biphenyl-3-sulfonyl)-1H-indol-3-yl]-propionic acid (P-0130, MS(ESI) [M+H]$^+$=566.0 (+DMSO)), 3-[5-Chloro-1-(2'-chloro-4'-ethoxy-biphenyl-3-sulfonyl)-1H-indol-3-yl]-propionic acid (P-0131, MS(ESI) [M+H$^+$]$^+$=596.0 (+DMSO)), 3-[5-Chloro-1-(2'-chloro-3'-fluoro-biphenyl-3-sulfonyl)-1H-indol-3-yl]-propionic acid (P-0132, MS(ESI) [M+H$^+$]$^+$=570.0 (+DMSO)), 3-[5-Chloro-1-(2'-chloro-4'-fluoro-biphenyl-3-sulfonyl)-1H-indol-3-yl]-propionic acid (P-0133, MS(ESI) [M+H$^+$]$^+$=570.4 (+DMSO)), 3-[5-Chloro-1-(4'-ethoxy-2'-methyl-biphenyl-3-sulfonyl)-1H-indol-3-yl]-propionic acid (P-0134, MS(ESI) [M+H$^+$]$^+$=576.4 (+DMSO)), 3-[5-Fluoro-1-(2-methyl-4'-trifluoromethyl-biphenyl-3-sulfonyl)-1H-indol-3-yl]-propionic acid (P-0137, MS(ESI) [M−H$^+$]$^-$=504), 3-[1-(4'-Chloro-2-methyl-biphenyl-3-sulfonyl)-5-fluoro-1H-indol-3-yl]-propionic acid (P-0138, MS(ESI) [M−H$^+$]$^-$=470.0, 472.0), 3-[7-Methyl-1-(4'-trifluoromethoxy-biphenyl-3-sulfonyl)-1H-indol-3-yl]-propionic acid (P-0139, MS(ESI) [M−H$^+$]$^-$=502), 3-[7-Methyl-1-(4'-trifluoromethyl-biphenyl-3-sulfonyl)-1H-indol-3-yl]-propionic acid (P-0140, MS(ESI) [M−H$^+$]$^-$=486), 3-[7-Chloro-1-(2'-fluoro-4'-trifluoromethyl-biphenyl-3-sulfonyl)-1H-indol-3-yl]-propionic acid (P-0141, MS(ESI) [M−H$^+$]$^-$=524.0), 3-[1-(2-Methyl-4'-trifluoromethyl-biphenyl-3-sulfonyl)-1H-indol-3-yl]-propionic acid (P-0142, MS(ESI) [M+H$^+$]$^+$=488.1), 3-[1-(2-Methyl-4'-trifluoromethoxy-biphenyl-3-sulfonyl)-1H-indol-3-yl]-propionic acid (P-0143, MS(ESI) [M−H$^+$]$^-$=502.1), 3-[7-Chloro-1-(4'-trifluoromethyl-biphenyl-3-sulfonyl)-1H-indol-3-yl]-propionic acid (P-0144, MS(ESI) [M−H$^+$]$^-$=506.0), 3-[7-Chloro-1-(4'-trifluoromethoxy-biphenyl-3-sulfonyl)-1H-indol-3-yl]-propionic acid (P-0145, MS(ESI) [M−H$^+$]$^-$=522.0), 3-[5-Chloro-1-(2-methyl-4'-trifluoromethyl-biphenyl-3-sulfonyl)-1H-indol-3-yl]-propionic acid (P-0146, MS(ESI) [M−H$^+$]$^-$=520.0), 3-[5-Chloro-1-(2-methyl-4'-trifluoromethoxy-biphenyl-3-sulfonyl)-1H-indol-3-yl]-propionic acid (P-0147, MS(ESI) [M−H$^+$]$^-$=536.0), and all salts, prodrugs, tautomers, and isomers thereof.

The following Table 1 indicates the compound number in Column 1, the indole used in Step 1 in Column 2, the sulfonyl chloride used in Step 3 in Column 3, and the boronic acid used in Step 4 in Column 4, followed by Table 2, which provides the compound number in Column 1, the resulting compound structure in Column 2, the compound name in Column 3, and the calculated and experimental mass in Columns 4 and 5.

TABLE 1

| Compound number | Step 1 indole | Step 3 sulfonyl chloride | Step 4 boronic acid | Resulting compound |
| --- | --- | --- | --- | --- |
| P-0001* | 5-chloro-1H-indole-3-carbaldehyde | 3-bromobenzenesulfonyl chloride | 4-(trifluoromethyl)phenylboronic acid | methyl 3-(5-chloro-1-((4'-(trifluoromethyl)biphenyl-3-yl)sulfonyl)-1H-indol-3-yl)propanoate |
| P-0002 | 5-chloro-1H-indole-3-carbaldehyde | 3-bromobenzenesulfonyl chloride | 4-(trifluoromethyl)phenylboronic acid | 3-(5-chloro-1-((4'-(trifluoromethyl)biphenyl-3-yl)sulfonyl)-1H-indol-3-yl)propanoic acid |
| P-0003 | 5-chloro-1H-indole-3-carbaldehyde | 3-bromobenzenesulfonyl chloride | 3-chlorophenylboronic acid | 3-(5-chloro-1-((3'-chlorobiphenyl-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0004 | 5-chloro-1H-indole-3-carbaldehyde | 3-bromobenzenesulfonyl chloride | 4-chlorophenylboronic acid | 3-(5-chloro-1-((4'-chloro-[1,1'-biphenyl]-3-yl)sulfonyl)-1H-indol-3-yl)propanoic acid |
| P-0005 | 5-chloro-1H-indole-3-carbaldehyde | 3-bromobenzenesulfonyl chloride | 4-methoxyphenylboronic acid | 3-(5-chloro-1-((4'-methoxy-[1,1'-biphenyl]-3-yl)sulfonyl)-1H-indol-3-yl)propanoic acid |
| P-0006 | 5-chloro-1H-indole-3-carbaldehyde | 3-bromobenzenesulfonyl chloride | 4-fluorophenylboronic acid | 3-(5-chloro-1-((4'-fluoro-[1,1'-biphenyl]-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
| --- | --- | --- | --- | --- |
| P-0007 | 5-chloro-1H-indole-3-carbaldehyde | 3-bromobenzenesulfonyl chloride | 2,4-difluorophenylboronic acid | 3-(5-chloro-1-((2',4'-difluoro-[1,1'-biphenyl]-3-yl)sulfonyl)-1H-indol-3-yl)propanoic acid |
| P-0008 | 5-chloro-1H-indole-3-carbaldehyde | 3-bromobenzenesulfonyl chloride | 3-chloro-4-fluorophenylboronic acid | 3-(5-chloro-1-((3'-chloro-4'-fluoro-[1,1'-biphenyl]-3-yl)sulfonyl)-1H-indol-3-yl)propanoic acid |
| P-0009 | 5-chloro-1H-indole-3-carbaldehyde | 3-bromobenzenesulfonyl chloride | 4-ethoxyphenylboronic acid | 3-(5-chloro-1-((4'-ethoxy-[1,1'-biphenyl]-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0010 | 5-chloro-1H-indole-3-carbaldehyde | 3-bromobenzenesulfonyl chloride | 3-fluorophenylboronic acid | 3-[5-chloro-1-(3'-fluorobiphenyl-3-ylsulfonyl)-1H-indol-3-yl]propanoic acid |
| P-0011 | 5-chloro-1H-indole-3-carbaldehyde | 3-bromobenzenesulfonyl chloride | 2-fluorophenylboronic acid | 3-[5-chloro-1-(2'-fluorobiphenyl-3-ylsulfonyl)-1H-indol-3-yl]propanoic acid |
| P-0012 | 5-chloro-1H-indole-3-carbaldehyde | 3-bromobenzenesulfonyl chloride | 3-(trifluoromethoxy)phenylboronic acid | 3-[5-chloro-1-(3'-(trifluoromethoxy)biphenyl-3-ylsulfonyl)-1H-indol-3-yl]propanoic acid |

TABLE 1-continued

| Compound number | Step 1 indole | Step 3 sulfonyl chloride | Step 4 boronic acid | Resulting compound |
|---|---|---|---|---|
| P-0013 | | | | |
| P-0014 | | | | |
| P-0015 | | | | |

TABLE 1-continued
| Compound number | Step 1 indole | Step 3 sulfonyl chloride | Step 4 boronic acid | Resulting compound |
|---|---|---|---|---|
| P-0016 | 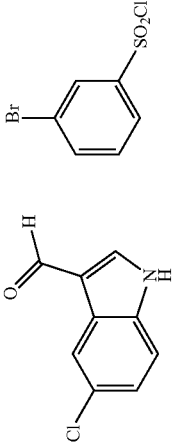 | 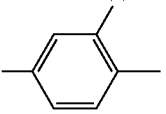 | 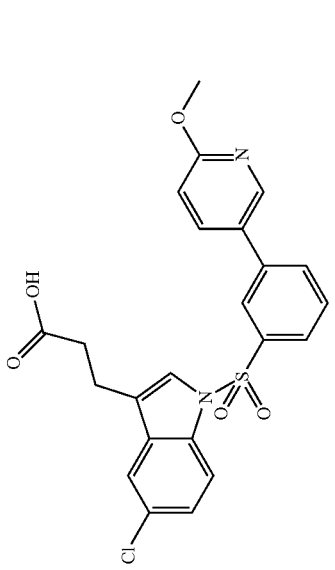 | 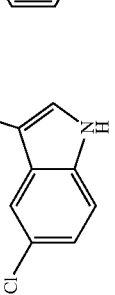 |
| P-0017 | 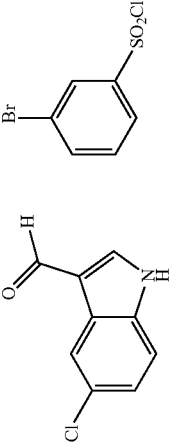 | 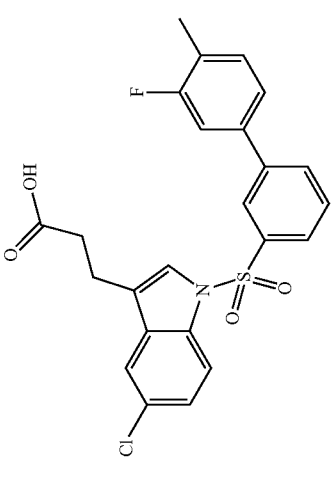 | 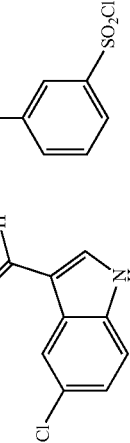 | 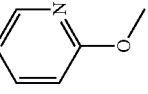 |
| P-0018 | 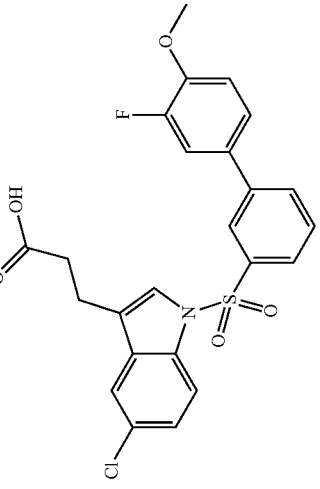 | 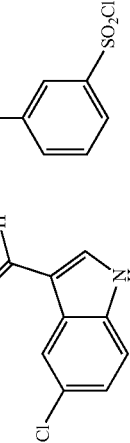 | 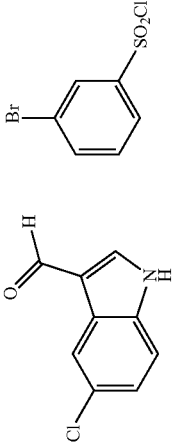 | 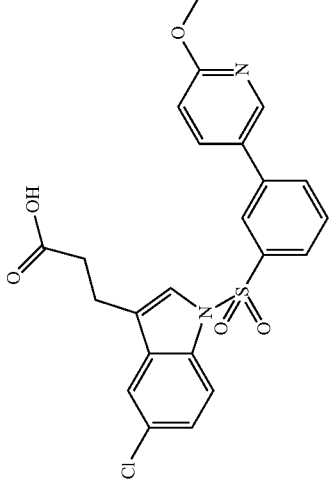 |

TABLE 1-continued

| Compound number | Step 1 indole | Step 3 sulfonyl chloride | Step 4 boronic acid | Resulting compound |
|---|---|---|---|---|
| P-0019 | 5-chloro-1H-indole-3-carbaldehyde | 3-bromobenzenesulfonyl chloride | 2-methoxypyrimidin-5-yl boronic acid | 3-(5-chloro-1-((3-(2-methoxypyrimidin-5-yl)phenyl)sulfonyl)-1H-indol-3-yl)propanoic acid |
| P-0020 | 5-chloro-1H-indole-3-carbaldehyde | 3-bromobenzenesulfonyl chloride | 2,4-dimethoxypyrimidin-5-yl boronic acid | 3-(5-chloro-1-((3-(2,4-dimethoxypyrimidin-5-yl)phenyl)sulfonyl)-1H-indol-3-yl)propanoic acid |
| P-0021 | 5-chloro-1H-indole-3-carbaldehyde | 3-bromobenzenesulfonyl chloride | 2-fluoro-4-(trifluoromethyl)phenyl boronic acid | 3-(5-chloro-1-((2'-fluoro-4'-(trifluoromethyl)-[1,1'-biphenyl]-3-yl)sulfonyl)-1H-indol-3-yl)propanoic acid |

TABLE 1-continued
| Compound number | Step 1 indole | Step 3 sulfonyl chloride | Step 4 boronic acid | Resulting compound |
|---|---|---|---|---|
| P-0022 | 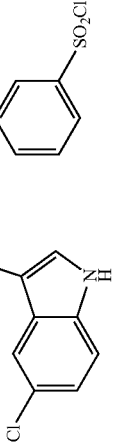 | 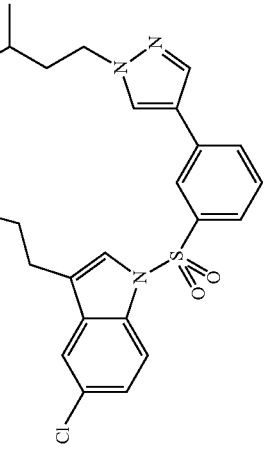 | 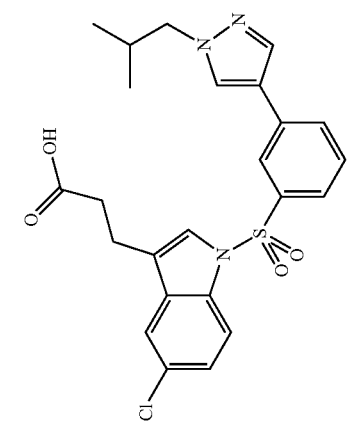 | 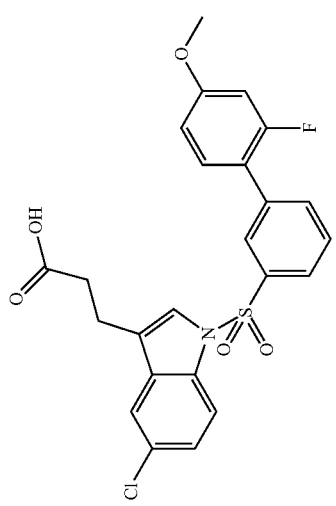 |
| P-0023 | 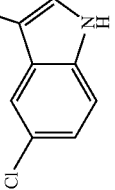 | 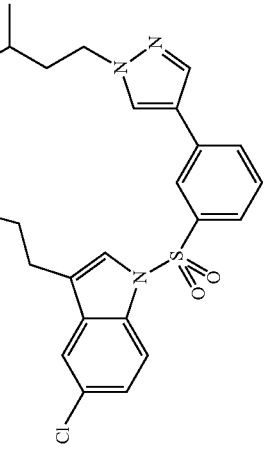 | 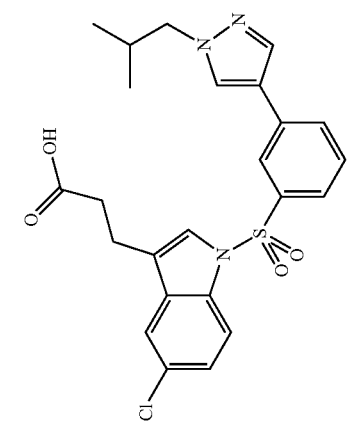 | 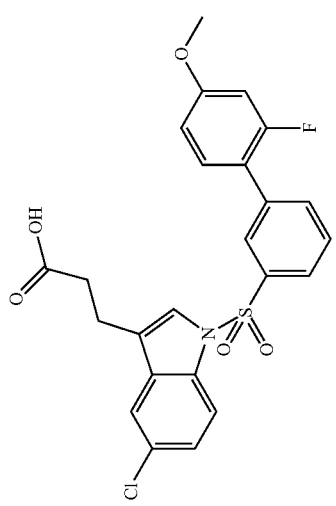 |
| P-0024 | 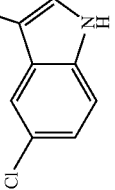 | 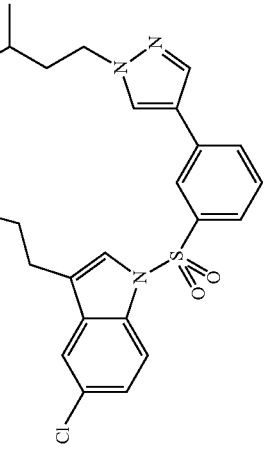 | 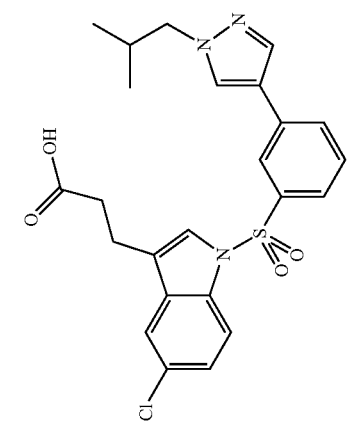 | 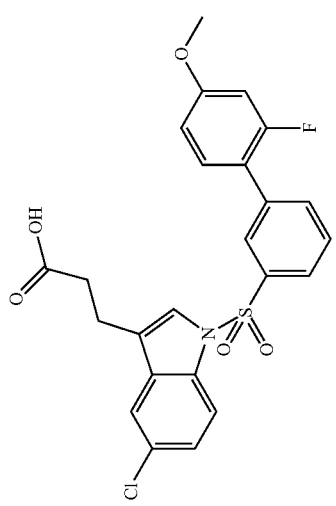 |

TABLE 1-continued

| Compound number | Step 1 indole | Step 3 sulfonyl chloride | Step 4 boronic acid | Resulting compound |
|---|---|---|---|---|
| P-0025 | 5-chloro-1H-indole-3-carbaldehyde | 3-bromobenzenesulfonyl chloride | 4-chloro-2-fluorophenylboronic acid | 3-(5-chloro-1-((4'-chloro-2'-fluorobiphenyl-3-yl)sulfonyl)-1H-indol-3-yl)propanoic acid |
| P-0026 | 5-fluoro-1H-indole-3-carbaldehyde | 3-bromobenzenesulfonyl chloride | 3-chlorophenylboronic acid | 3-(1-((3'-chlorobiphenyl-3-yl)sulfonyl)-5-fluoro-1H-indol-3-yl)propanoic acid |
| P-0027 | 5-fluoro-1H-indole-3-carbaldehyde | 3-bromobenzenesulfonyl chloride | 4-chlorophenylboronic acid | 3-(1-((4'-chlorobiphenyl-3-yl)sulfonyl)-5-fluoro-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0028 | 5-fluoro-1H-indole-3-carbaldehyde | 3-bromobenzenesulfonyl chloride | 4-methoxyphenylboronic acid | 3-[1-[(4'-methoxybiphenyl-3-yl)sulfonyl]-5-fluoro-1H-indol-3-yl]propanoic acid |
| P-0029 | 5-fluoro-1H-indole-3-carbaldehyde | 3-bromobenzenesulfonyl chloride | 4-fluorophenylboronic acid | 3-[1-[(4'-fluorobiphenyl-3-yl)sulfonyl]-5-fluoro-1H-indol-3-yl]propanoic acid |
| P-0030 | 5-fluoro-1H-indole-3-carbaldehyde | 3-bromobenzenesulfonyl chloride | 3-chloro-4-fluorophenylboronic acid | 3-[1-[(3'-chloro-4'-fluorobiphenyl-3-yl)sulfonyl]-5-fluoro-1H-indol-3-yl]propanoic acid |

TABLE 1-continued

| Compound number | Step 1 indole | Step 3 sulfonyl chloride | Step 4 boronic acid | Resulting compound |
| --- | --- | --- | --- | --- |
| P-0031 | 5-fluoro-1H-indole-3-carbaldehyde | 3-bromobenzenesulfonyl chloride | 3-fluorophenylboronic acid | 3-(1-((3'-fluoro-[1,1'-biphenyl]-3-yl)sulfonyl)-5-fluoro-1H-indol-3-yl)propanoic acid |
| P-0032 | 5-fluoro-1H-indole-3-carbaldehyde | 3-bromobenzenesulfonyl chloride | 2-fluorophenylboronic acid | 3-(1-((2'-fluoro-[1,1'-biphenyl]-3-yl)sulfonyl)-5-fluoro-1H-indol-3-yl)propanoic acid |
| P-0033 | 5-fluoro-1H-indole-3-carbaldehyde | 3-bromobenzenesulfonyl chloride | 3-(trifluoromethoxy)phenylboronic acid | 3-(5-fluoro-1-((3'-(trifluoromethoxy)-[1,1'-biphenyl]-3-yl)sulfonyl)-1H-indol-3-yl)propanoic acid |

TABLE 1-continued
| Compound number | Step 1 indole | Step 3 sulfonyl chloride | Step 4 boronic acid | Resulting compound |
|---|---|---|---|---|
| P-0034 | 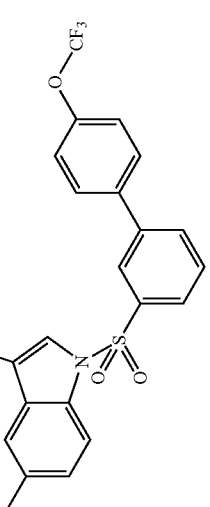 | 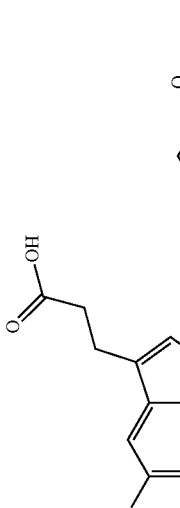 | 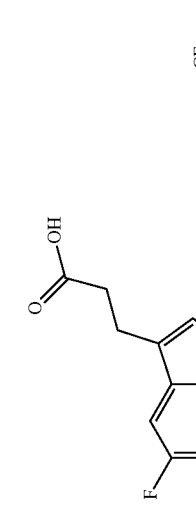 | 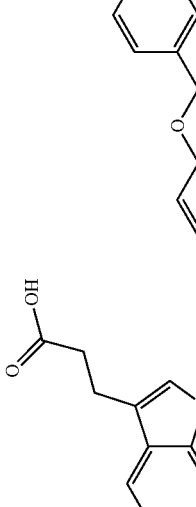 |
| P-0035 |  | 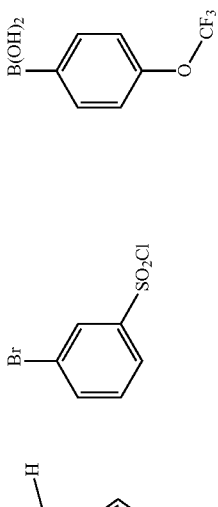 | 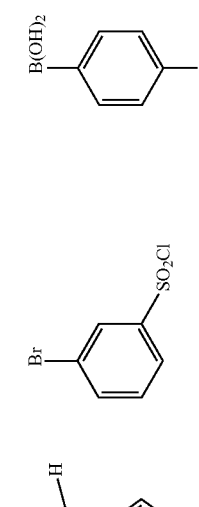 | 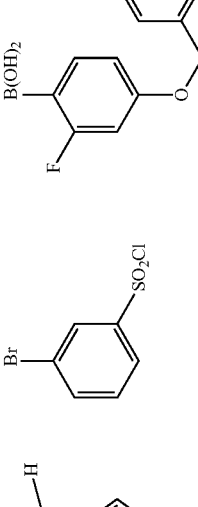 |
| P-0036 |  | 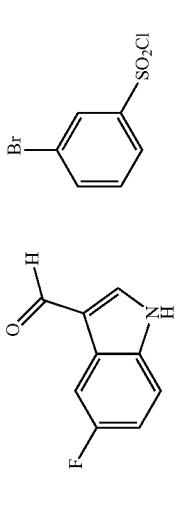 | 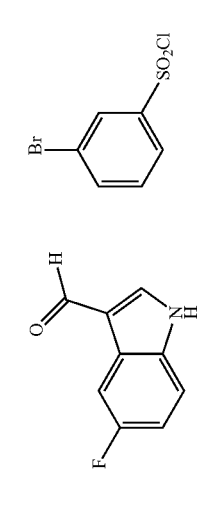 | 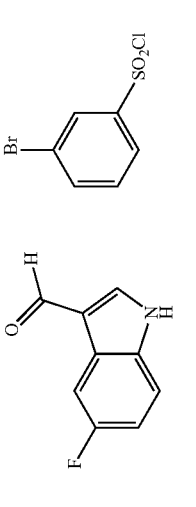 |

TABLE 1-continued

| Compound number | Step 1 indole | Step 3 sulfonyl chloride | Step 4 boronic acid | Resulting compound |
|---|---|---|---|---|
| P-0037 | 5-fluoro-1H-indole-3-carbaldehyde | 3-bromobenzenesulfonyl chloride | (6-methoxypyridin-3-yl)boronic acid | 3-(5-fluoro-1-((3-(6-methoxypyridin-3-yl)phenyl)sulfonyl)-1H-indol-3-yl)propanoic acid |
| P-0038 | 5-fluoro-1H-indole-3-carbaldehyde | 3-bromobenzenesulfonyl chloride | (3-fluoro-4-methoxyphenyl)boronic acid | 3-(5-fluoro-1-((3'-fluoro-4'-methoxy-[1,1'-biphenyl]-3-yl)sulfonyl)-1H-indol-3-yl)propanoic acid |
| P-0039 | 5-fluoro-1H-indole-3-carbaldehyde | 3-bromobenzenesulfonyl chloride | (2-methoxypyrimidin-5-yl)boronic acid | 3-(5-fluoro-1-((3-(2-methoxypyrimidin-5-yl)phenyl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0040 | 5-fluoro-1H-indole-3-carbaldehyde | 3-bromobenzenesulfonyl chloride | 2,4-dimethoxypyrimidin-5-yl boronic acid | 3-(1-((3-(2,4-dimethoxypyrimidin-5-yl)phenyl)sulfonyl)-5-fluoro-1H-indol-3-yl)propanoic acid |
| P-0041 | 5-fluoro-1H-indole-3-carbaldehyde | 3-bromobenzenesulfonyl chloride | 1-isopentyl-1H-pyrazol-4-yl boronic acid | 3-(5-fluoro-1-((3-(1-isopentyl-1H-pyrazol-4-yl)phenyl)sulfonyl)-1H-indol-3-yl)propanoic acid |
| P-0042 | 5-fluoro-1H-indole-3-carbaldehyde | 3-bromobenzenesulfonyl chloride | 1-isobutyl-1H-pyrazol-4-yl boronic acid | 3-(5-fluoro-1-((3-(1-isobutyl-1H-pyrazol-4-yl)phenyl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0043 | 5-fluoro-1H-indole-3-carbaldehyde | 3-bromobenzenesulfonyl chloride | 2-fluoro-4-methoxyphenylboronic acid | |
| P-0044 | 5-fluoro-1H-indole-3-carbaldehyde | 3-bromobenzenesulfonyl chloride | 4-chloro-2-fluorophenylboronic acid | |
| P-0045 | 5-methoxy-1H-indole-3-carbaldehyde | 3-bromobenzenesulfonyl chloride | 3-chlorophenylboronic acid | |

TABLE 1-continued

| Compound number | Step 1 indole | Step 3 sulfonyl chloride | Step 4 boronic acid | Resulting compound |
|---|---|---|---|---|
| P-0046 | 5-methoxy-1H-indole-3-carbaldehyde | 3-bromobenzenesulfonyl chloride | 4-chlorophenylboronic acid | 3-(1-((4'-chloro-[1,1'-biphenyl]-3-yl)sulfonyl)-5-methoxy-1H-indol-3-yl)propanoic acid |
| P-0047 | 5-methoxy-1H-indole-3-carbaldehyde | 3-bromobenzenesulfonyl chloride | 4-methoxyphenylboronic acid | 3-(5-methoxy-1-((4'-methoxy-[1,1'-biphenyl]-3-yl)sulfonyl)-1H-indol-3-yl)propanoic acid |
| P-0048 | 5-methoxy-1H-indole-3-carbaldehyde | 3-bromobenzenesulfonyl chloride | 4-fluorophenylboronic acid | 3-(1-((4'-fluoro-[1,1'-biphenyl]-3-yl)sulfonyl)-5-methoxy-1H-indol-3-yl)propanoic acid |

TABLE 1-continued
| Compound number | Step 1 indole | Step 3 sulfonyl chloride | Step 4 boronic acid | Resulting compound |
|---|---|---|---|---|
| P-0049 |  | 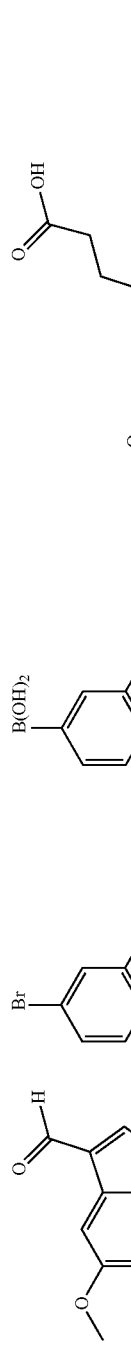 |  | 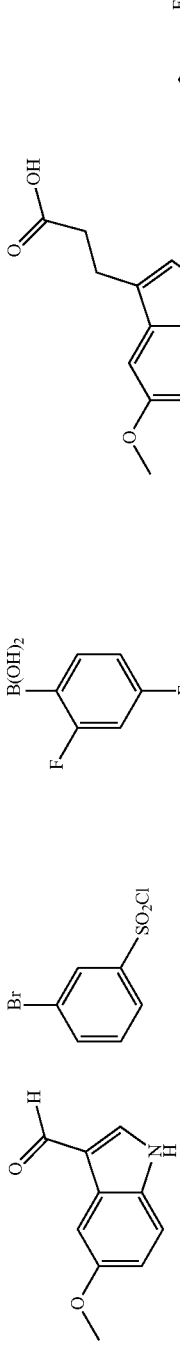 |
| P-0050 | 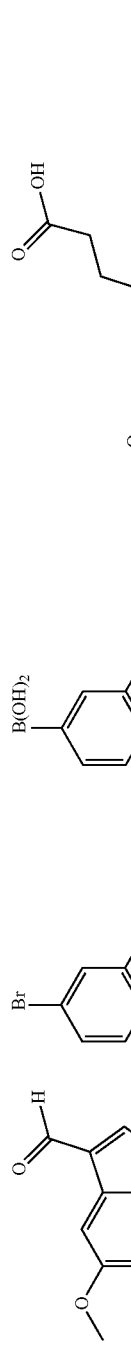 |  | 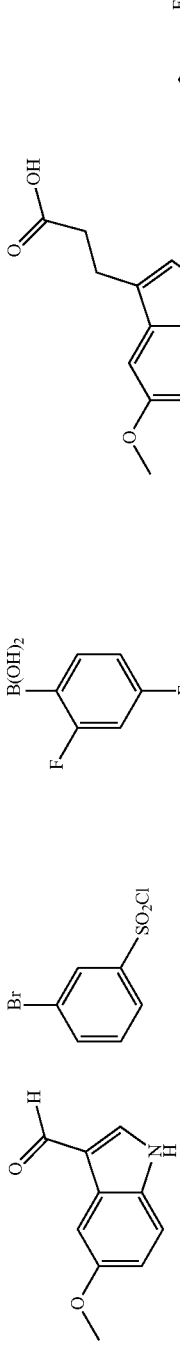 |  |
| P-0051 |  | 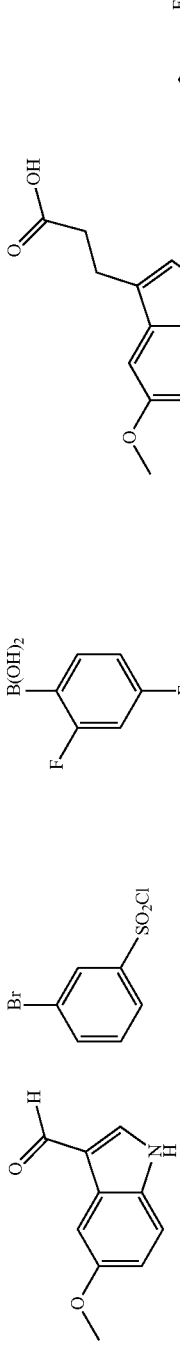 |  | 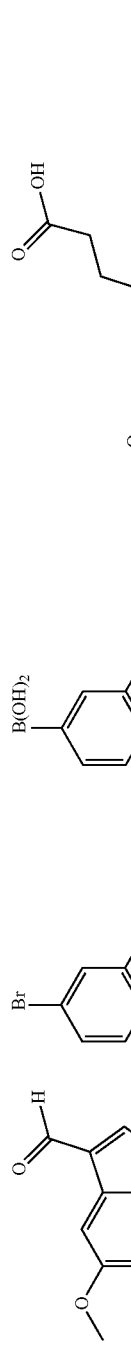 |

TABLE 1-continued
| Compound number | Step 1 indole | Step 3 sulfonyl chloride | Step 4 boronic acid | Resulting compound |
|---|---|---|---|---|
| P-0052 | 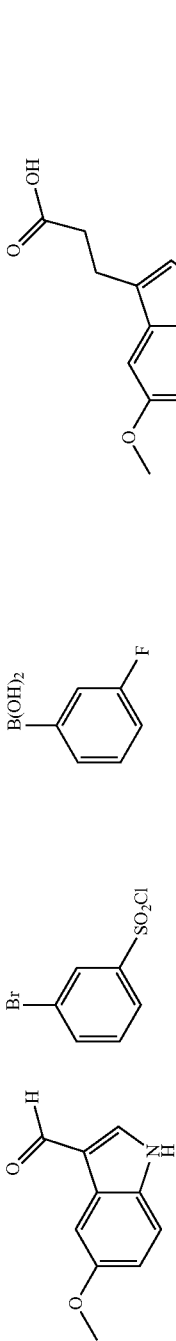 |  | 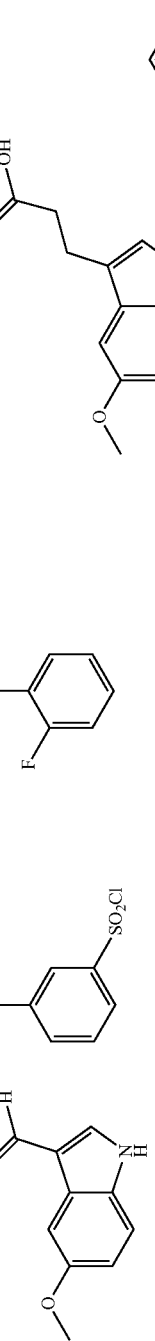 |  |
| P-0053 | 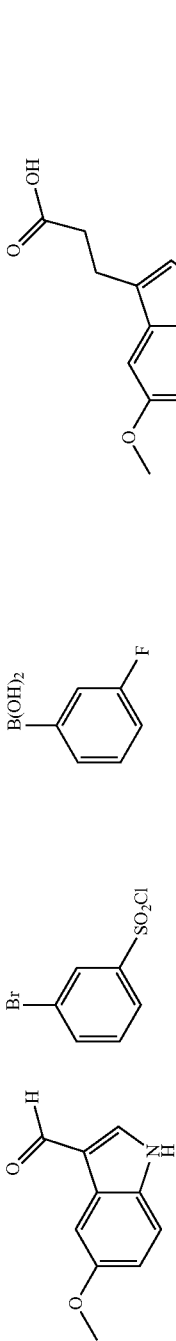 |  | 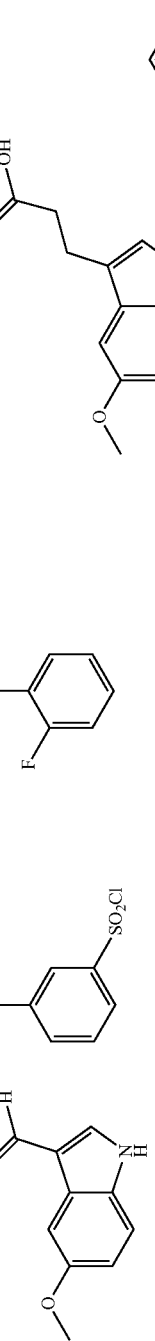 |  |
| P-0054 | 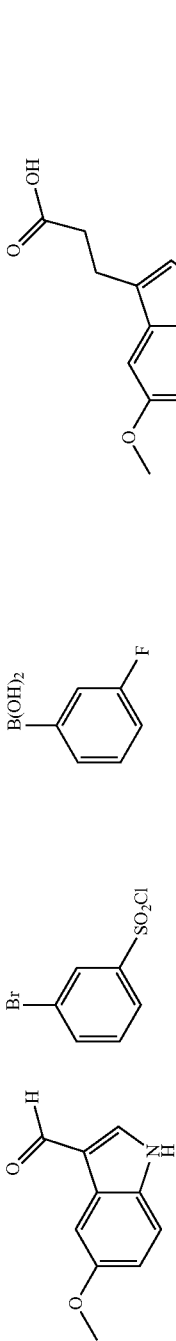 |  | 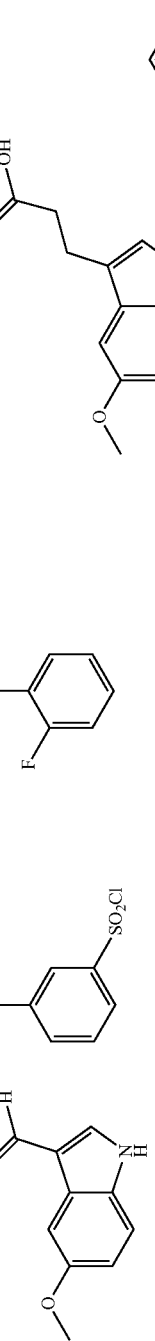 |  |

TABLE 1-continued
| Compound number | Step 1 indole | Step 3 sulfonyl chloride | Step 4 boronic acid | Resulting compound |
|---|---|---|---|---|
| P-0055 | 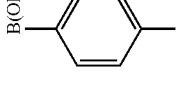 | 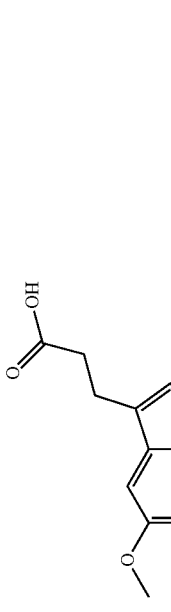 | 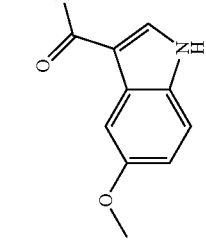 | 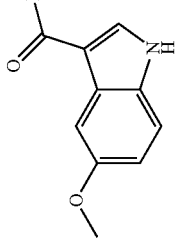 |
| P-0056 | 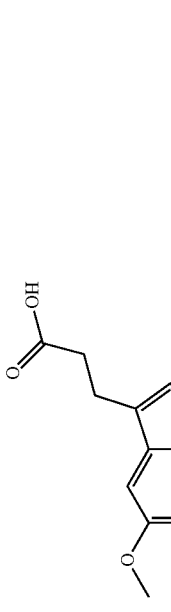 | 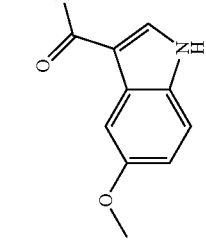 | 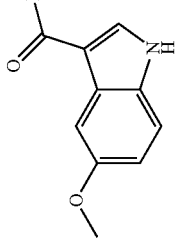 | 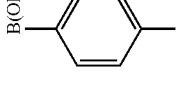 |
| P-0057 | 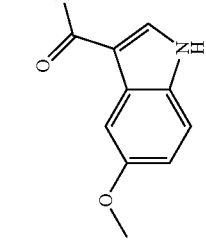 | 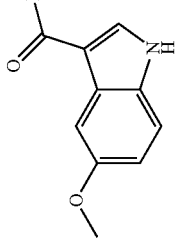 | 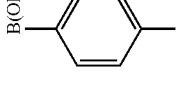 | 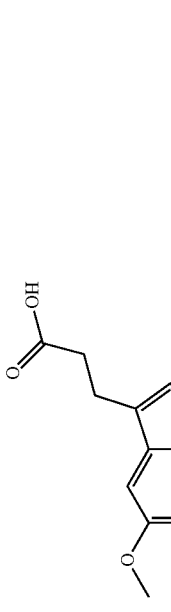 |

TABLE 1-continued

| Compound number | Step 1 indole | Step 3 sulfonyl chloride | Step 4 boronic acid | Resulting compound |
|---|---|---|---|---|
| P-0058 | 5-methoxy-1H-indole-3-carbaldehyde | 3-bromobenzenesulfonyl chloride | (6-methoxypyridin-3-yl)boronic acid | 3-(1-((3-(6-methoxypyridin-3-yl)phenyl)sulfonyl)-5-methoxy-1H-indol-3-yl)propanoic acid |
| P-0059 | 5-methoxy-1H-indole-3-carbaldehyde | 3-bromobenzenesulfonyl chloride | (3-fluoro-4-methylphenyl)boronic acid | 3-(1-((3'-fluoro-4'-methylbiphenyl-3-yl)sulfonyl)-5-methoxy-1H-indol-3-yl)propanoic acid |
| P-0060 | 5-methoxy-1H-indole-3-carbaldehyde | 3-bromobenzenesulfonyl chloride | (3-fluoro-4-methoxyphenyl)boronic acid | 3-(1-((3'-fluoro-4'-methoxybiphenyl-3-yl)sulfonyl)-5-methoxy-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0061 | 5-methoxy-1H-indole-3-carbaldehyde | 3-bromobenzenesulfonyl chloride | 2-methoxypyrimidine-5-boronic acid | 3-(1-((3-(2-methoxypyrimidin-5-yl)phenyl)sulfonyl)-5-methoxy-1H-indol-3-yl)propanoic acid |
| P-0062 | 5-methoxy-1H-indole-3-carbaldehyde | 3-bromobenzenesulfonyl chloride | 2,4-dimethoxypyrimidine-5-boronic acid | 3-(1-((3-(2,4-dimethoxypyrimidin-5-yl)phenyl)sulfonyl)-5-methoxy-1H-indol-3-yl)propanoic acid |
| P-0063 | 5-methoxy-1H-indole-3-carbaldehyde | 3-bromobenzenesulfonyl chloride | 2-fluoro-4-(trifluoromethyl)phenylboronic acid | 3-(1-((2'-fluoro-4'-(trifluoromethyl)-[1,1'-biphenyl]-3-yl)sulfonyl)-5-methoxy-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0064 | 5-methoxy-1H-indole-3-carbaldehyde | 3-bromobenzenesulfonyl chloride | 1-isobutyl-1H-pyrazol-4-yl boronic acid | 3-(1-(3-(1-isobutyl-1H-pyrazol-4-yl)phenylsulfonyl)-5-methoxy-1H-indol-3-yl)propanoic acid |
| P-0065 | 5-methoxy-1H-indole-3-carbaldehyde | 3-bromobenzenesulfonyl chloride | 1-isobutyl-1H-pyrazol-4-yl boronic acid | 3-(1-(3-(1-isobutyl-1H-pyrazol-4-yl)phenylsulfonyl)-5-methoxy-1H-indol-3-yl)propanoic acid |
| P-0066 | 5-methoxy-1H-indole-3-carbaldehyde | 3-bromobenzenesulfonyl chloride | 2-fluoro-4-methoxyphenylboronic acid | 3-(1-(2'-fluoro-4'-methoxybiphenyl-3-ylsulfonyl)-5-methoxy-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0067 | 5-methoxy-1H-indole-3-carbaldehyde | 3-bromobenzenesulfonyl chloride | 4-chloro-2-fluorophenylboronic acid | 3-(1-((4'-chloro-2'-fluorobiphenyl-3-yl)sulfonyl)-5-methoxy-1H-indol-3-yl)propanoic acid |
| P-0068 | 5-fluoro-1H-indole-3-carbaldehyde | 3-bromobenzenesulfonyl chloride | 2,4-difluorophenylboronic acid | 3-(1-((2',4'-difluorobiphenyl-3-yl)sulfonyl)-5-fluoro-1H-indol-3-yl)propanoic acid |
| P-0069 | 5-fluoro-1H-indole-3-carbaldehyde | 3-bromobenzenesulfonyl chloride | 2-fluoro-4-(trifluoromethyl)phenylboronic acid | 3-(1-((2'-fluoro-4'-(trifluoromethyl)biphenyl-3-yl)sulfonyl)-5-fluoro-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0070 | 1H-indole-3-carbaldehyde | 3-bromobenzenesulfonyl chloride | 3-chlorophenylboronic acid | 3-[1-(3'-chlorobiphenyl-3-ylsulfonyl)-1H-indol-3-yl]propanoic acid |
| P-0071 | 1H-indole-3-carbaldehyde | 3-bromobenzenesulfonyl chloride | 4-chlorophenylboronic acid | 3-[1-(4'-chlorobiphenyl-3-ylsulfonyl)-1H-indol-3-yl]propanoic acid |
| P-0072 | 1H-indole-3-carbaldehyde | 3-bromobenzenesulfonyl chloride | 4-methoxyphenylboronic acid | 3-[1-(4'-methoxybiphenyl-3-ylsulfonyl)-1H-indol-3-yl]propanoic acid |

TABLE 1-continued
| Compound number | Step 1 indole | Step 3 sulfonyl chloride | Step 4 boronic acid | Resulting compound |
|---|---|---|---|---|
| P-0073 | 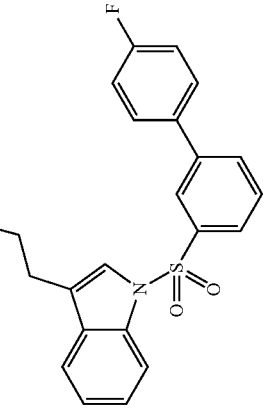 | 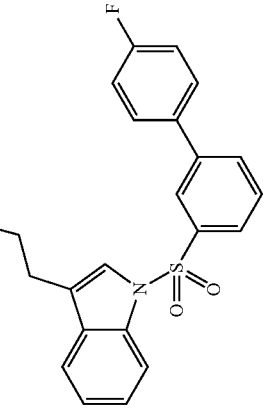 | 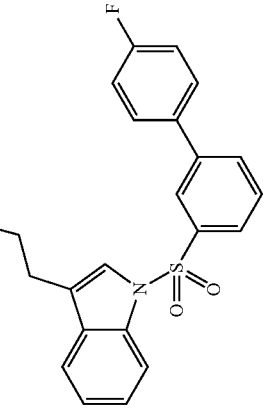 | 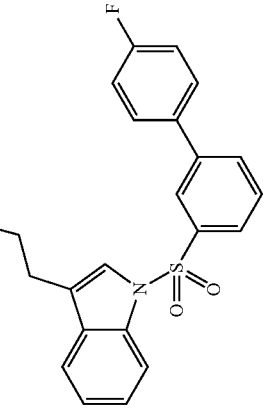 |
| P-0074 | 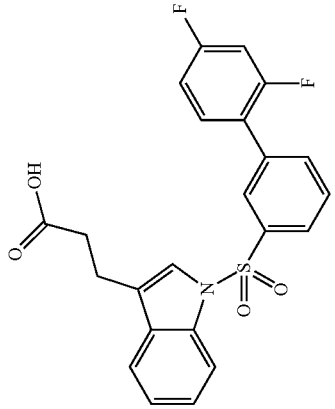 | 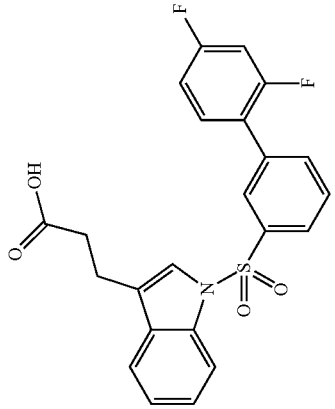 | 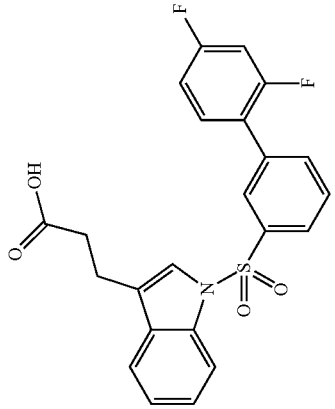 | 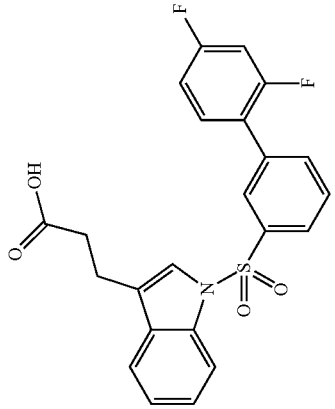 |
| P-0075 | 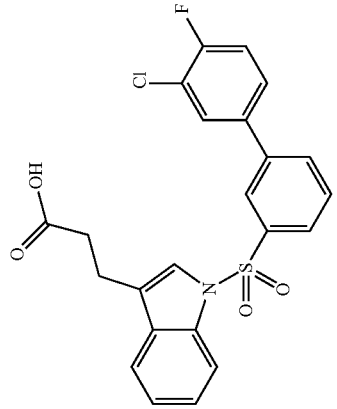 | 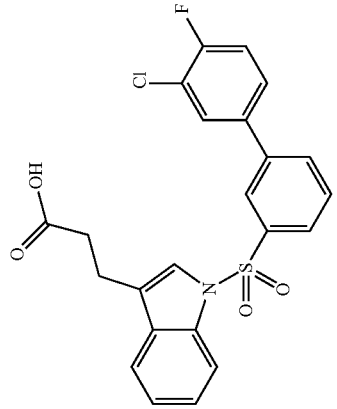 | 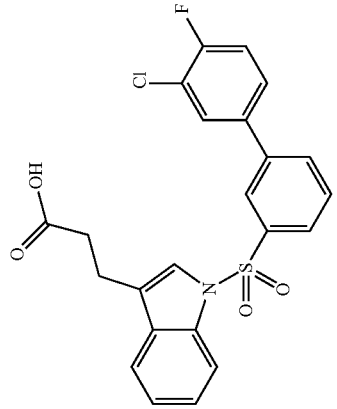 | 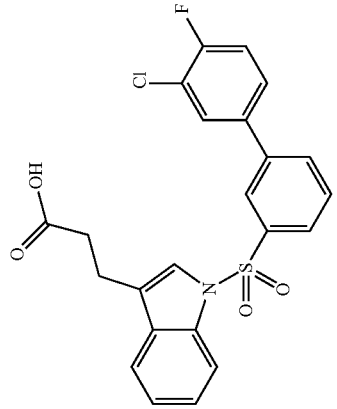 |

TABLE 1-continued
| Compound number | Step 1 indole | Step 3 sulfonyl chloride | Step 4 boronic acid | Resulting compound |
|---|---|---|---|---|
| P-0076 | 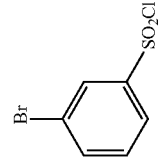 | 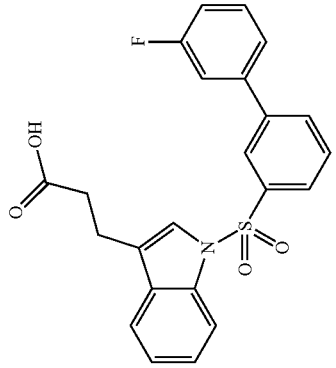 | 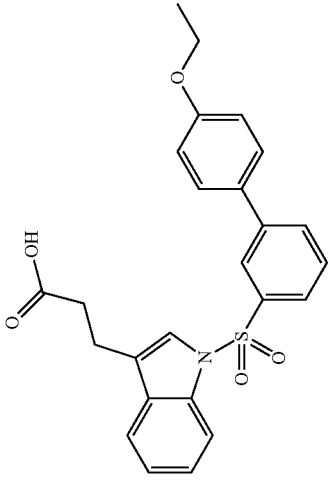 | 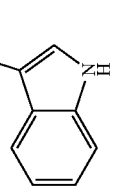 |
| P-0077 | 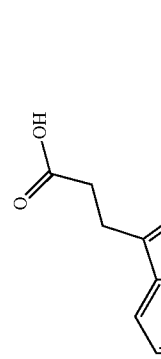 | 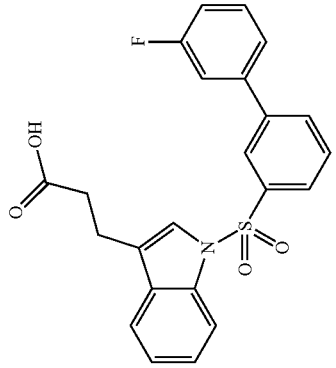 | 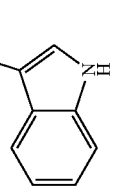 | 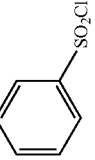 |
| P-0078 | 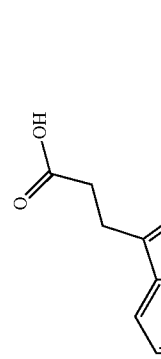 | 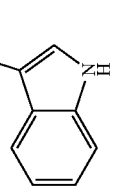 | 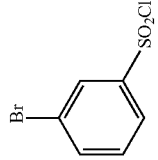 | 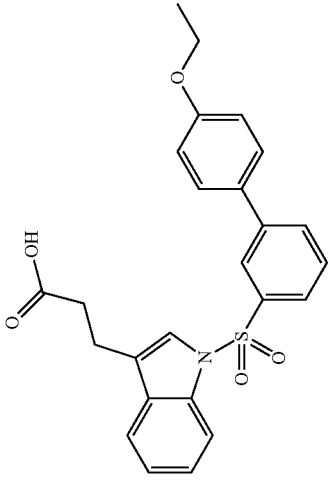 |

TABLE 1-continued
| Compound number | Step 1 indole | Step 3 sulfonyl chloride | Step 4 boronic acid | Resulting compound |
| --- | --- | --- | --- | --- |
| P-0079 | 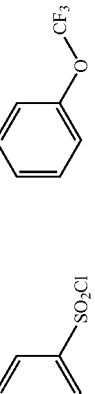 | 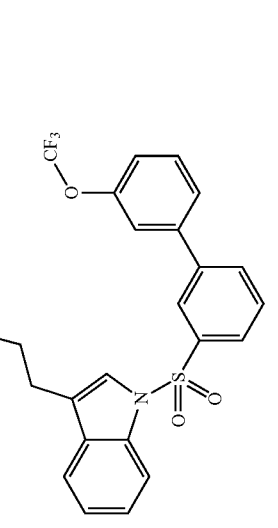 | 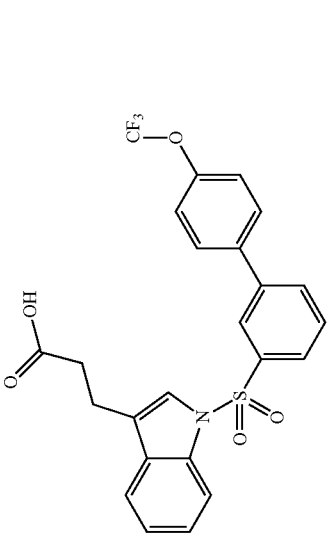 | 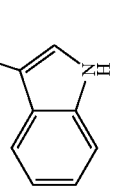 |
| P-0080 | 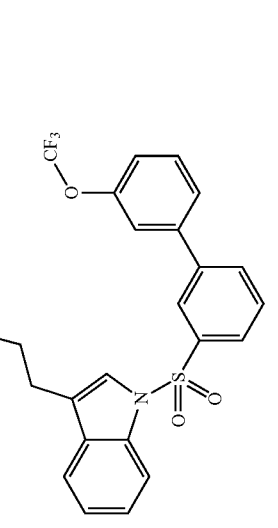 | 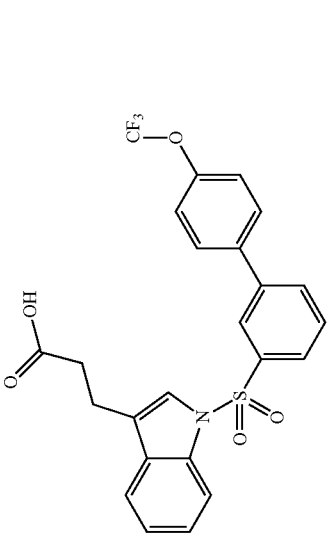 | 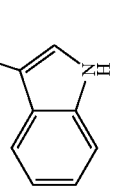 | 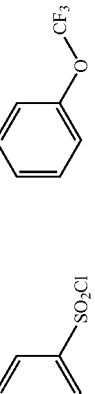 |
| P-0081 | 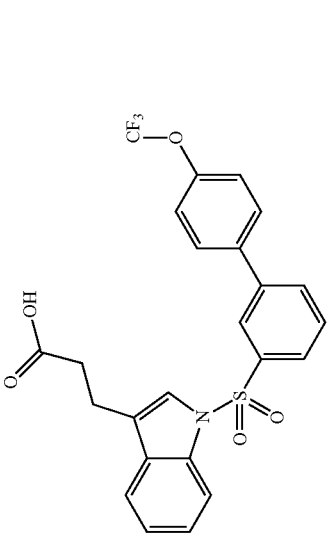 | 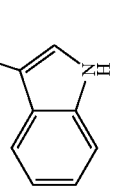 | 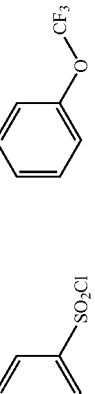 | 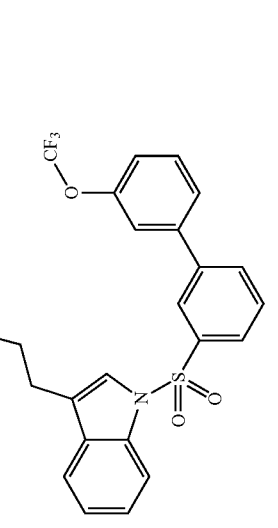 |

TABLE 1-continued

| Compound number | Step 1 indole | Step 3 sulfonyl chloride | Step 4 boronic acid | Resulting compound |
|---|---|---|---|---|
| P-0082 | 1H-indole-3-carbaldehyde | 3-bromobenzenesulfonyl chloride | 4-benzyloxy-2-fluorophenylboronic acid | 3-(1-((4'-(benzyloxy)-2'-fluoro-[1,1'-biphenyl]-3-yl)sulfonyl)-1H-indol-3-yl)propanoic acid |
| P-0083 | 1H-indole-3-carbaldehyde | 3-bromobenzenesulfonyl chloride | 6-methoxypyridine-3-boronic acid | 3-(1-((3-(6-methoxypyridin-3-yl)phenyl)sulfonyl)-1H-indol-3-yl)propanoic acid |
| P-0084 | 1H-indole-3-carbaldehyde | 3-bromobenzenesulfonyl chloride | 3-fluoro-4-methylphenylboronic acid | 3-(1-((3'-fluoro-4'-methyl-[1,1'-biphenyl]-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0085 | 1H-indole-3-carbaldehyde | 3-bromobenzenesulfonyl chloride | 3-fluoro-4-methoxyphenylboronic acid | 3-(1-((3'-fluoro-4'-methoxy-[1,1'-biphenyl]-3-yl)sulfonyl)-1H-indol-3-yl)propanoic acid |
| P-0086 | 1H-indole-3-carbaldehyde | 3-bromobenzenesulfonyl chloride | 2,4-dimethoxypyrimidin-5-ylboronic acid | 3-(1-((3-(2,4-dimethoxypyrimidin-5-yl)phenyl)sulfonyl)-1H-indol-3-yl)propanoic acid |
| P-0087 | 1H-indole-3-carbaldehyde | 3-bromobenzenesulfonyl chloride | 2-fluoro-4-(trifluoromethyl)phenylboronic acid | 3-(1-((2'-fluoro-4'-(trifluoromethyl)-[1,1'-biphenyl]-3-yl)sulfonyl)-1H-indol-3-yl)propanoic acid |

TABLE 1-continued
| Compound number | Step 1 indole | Step 3 sulfonyl chloride | Step 4 boronic acid | Resulting compound |
|---|---|---|---|---|
| P-0088 | 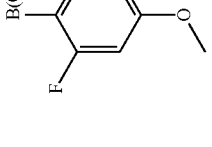 | 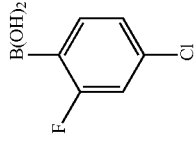 | 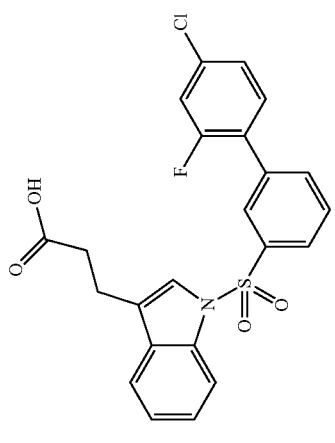 | 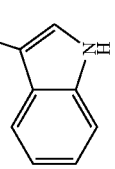 |
| P-0089 | 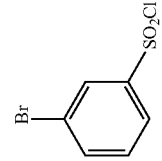 | 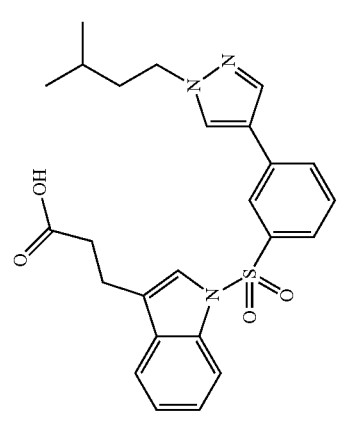 | 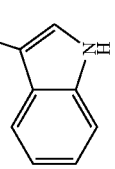 | 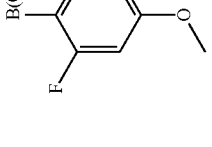 |
| P-0090 | 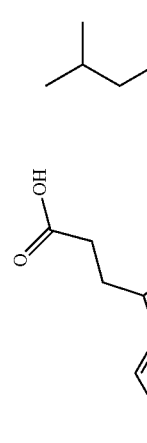 | 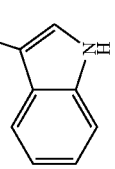 | 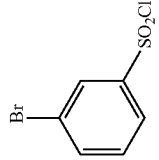 | 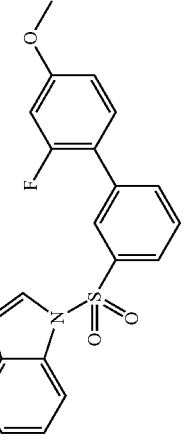 |

TABLE 1-continued

| Compound number | Step 1 indole | Step 3 sulfonyl chloride | Step 4 boronic acid | Resulting compound |
|---|---|---|---|---|
| P-0091 | 1H-indole-3-carbaldehyde | 3-bromobenzenesulfonyl chloride | 1-isobutyl-1H-pyrazol-4-yl boronic acid | |
| P-0092 | 1H-indole-3-carbaldehyde | 3-bromobenzenesulfonyl chloride | phenylboronic acid | |
| P-0093 | 1H-indole-3-carbaldehyde | 3-bromobenzenesulfonyl chloride | 2,4-dichlorophenylboronic acid | |

TABLE 1-continued

| Compound number | Step 1 indole | Step 3 sulfonyl chloride | Step 4 boronic acid | Resulting compound |
|---|---|---|---|---|
| P-0094 | 1H-indole-3-carbaldehyde | 3-bromobenzenesulfonyl chloride | 4-fluoro-2-methylphenylboronic acid | 3-(1-((4'-fluoro-2'-methylbiphenyl-3-yl)sulfonyl)-1H-indol-3-yl)propanoic acid |
| P-0095 | 1H-indole-3-carbaldehyde | 3-bromobenzenesulfonyl chloride | 2,3-dichlorophenylboronic acid | 3-(1-((2',3'-dichlorobiphenyl-3-yl)sulfonyl)-1H-indol-3-yl)propanoic acid |
| P-0096 | 1H-indole-3-carbaldehyde | 3-bromobenzenesulfonyl chloride | 2,3-difluorophenylboronic acid | 3-(1-((2',3'-difluorobiphenyl-3-yl)sulfonyl)-1H-indol-3-yl)propanoic acid |

TABLE 1-continued
| Compound number | Step 1 indole | Step 3 sulfonyl chloride | Step 4 boronic acid | Resulting compound |
|---|---|---|---|---|
| P-0097 | 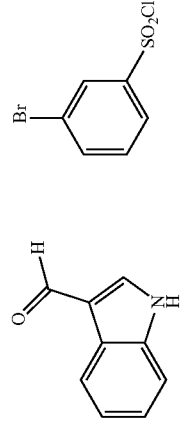 | 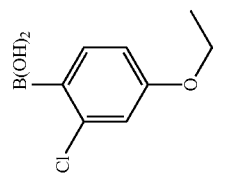 | 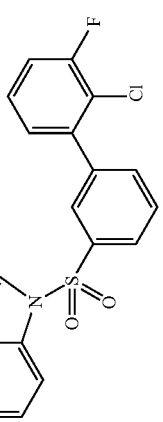 | 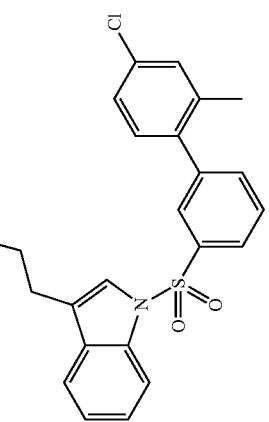 |
| P-0098 | 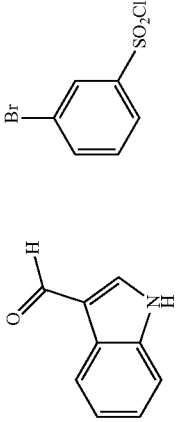 | 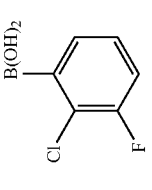 |  | 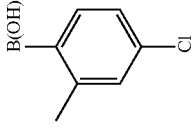 |
| P-0099 | 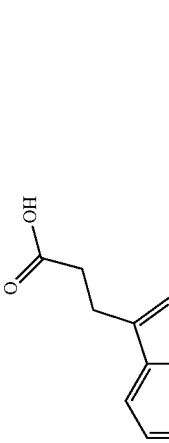 |  | 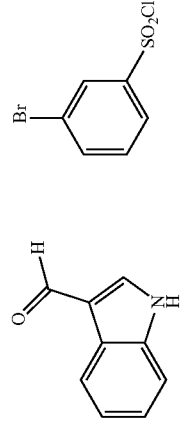 | 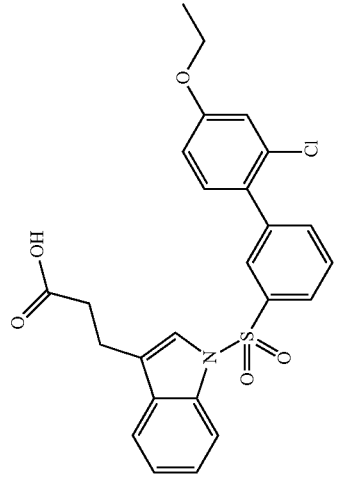 |

TABLE 1-continued
| Compound number | Step 1 indole | Step 3 sulfonyl chloride | Step 4 boronic acid | Resulting compound |
|---|---|---|---|---|
| P-0100 | 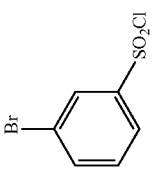 | 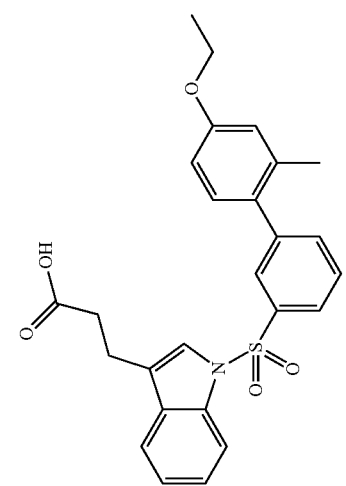 | 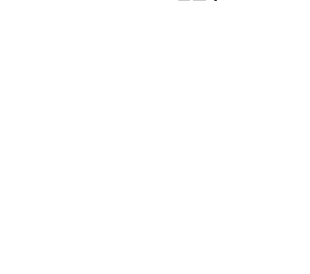 | 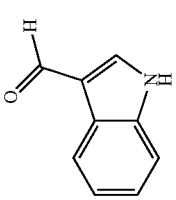 |
| P-0101 | 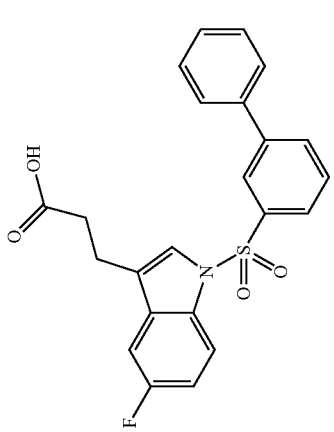 |  | 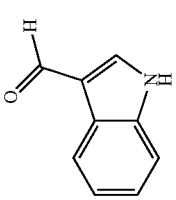 | 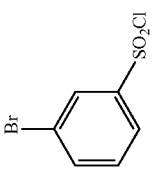 |
| P-0102 | 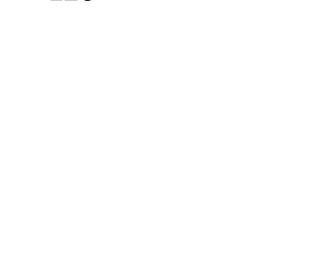 | 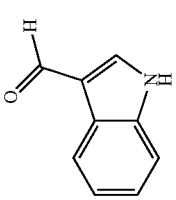 | 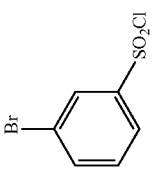 | 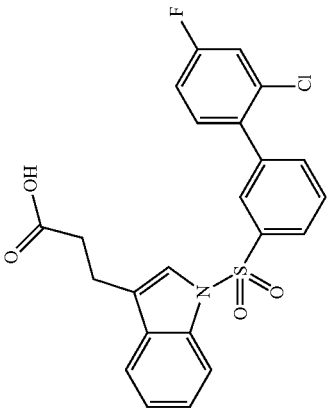 |

TABLE 1-continued

| Compound number | Step 1 indole | Step 3 sulfonyl chloride | Step 4 boronic acid | Resulting compound |
|---|---|---|---|---|
| P-0103 | 5-fluoro-1H-indole-3-carbaldehyde | 3-bromobenzenesulfonyl chloride | 2,4-dichlorophenylboronic acid | 3-(3-((2',4'-dichloro-[1,1'-biphenyl]-3-yl)sulfonyl)-6-fluoro-1H-indol-3-yl)propanoic acid |
| P-0104 | 5-fluoro-1H-indole-3-carbaldehyde | 3-bromobenzenesulfonyl chloride | 4-fluoro-2-methylphenylboronic acid | 3-(6-fluoro-3-((4'-fluoro-2'-methyl-[1,1'-biphenyl]-3-yl)sulfonyl)-1H-indol-3-yl)propanoic acid |
| P-0105 | 5-fluoro-1H-indole-3-carbaldehyde | 3-bromobenzenesulfonyl chloride | 2,3-dichlorophenylboronic acid | 3-(3-((2',3'-dichloro-[1,1'-biphenyl]-3-yl)sulfonyl)-6-fluoro-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0106 | 5-fluoro-1H-indole-3-carbaldehyde | 3-bromobenzenesulfonyl chloride | 2,3-difluorophenylboronic acid | 3-(5-fluoro-1-((2',3'-difluoro-[1,1'-biphenyl]-3-yl)sulfonyl)-1H-indol-3-yl)propanoic acid |
| P-0107 | 5-fluoro-1H-indole-3-carbaldehyde | 3-bromobenzenesulfonyl chloride | 2-chloro-4-(trifluoromethyl)phenylboronic acid | 3-(5-fluoro-1-((2'-chloro-4'-(trifluoromethyl)-[1,1'-biphenyl]-3-yl)sulfonyl)-1H-indol-3-yl)propanoic acid |
| P-0108 | 5-fluoro-1H-indole-3-carbaldehyde | 3-bromobenzenesulfonyl chloride | 4-chloro-2-methylphenylboronic acid | 3-(5-fluoro-1-((4'-chloro-2'-methyl-[1,1'-biphenyl]-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0109 | 5-fluoro-1H-indole-3-carbaldehyde | 3-bromobenzenesulfonyl chloride | 2-chloro-4-ethoxyphenylboronic acid | 3-{1-[(2'-chloro-4'-ethoxybiphenyl-3-yl)sulfonyl]-5-fluoro-1H-indol-3-yl}propanoic acid |
| P-0110 | 5-fluoro-1H-indole-3-carbaldehyde | 3-bromobenzenesulfonyl chloride | 2-chloro-3-fluorophenylboronic acid | 3-{1-[(2'-chloro-3'-fluorobiphenyl-3-yl)sulfonyl]-5-fluoro-1H-indol-3-yl}propanoic acid |
| P-0111 | 5-fluoro-1H-indole-3-carbaldehyde | 3-bromobenzenesulfonyl chloride | 2-chloro-4-fluorophenylboronic acid | 3-{1-[(2'-chloro-4'-fluorobiphenyl-3-yl)sulfonyl]-5-fluoro-1H-indol-3-yl}propanoic acid |

TABLE 1-continued
| Compound number | Step 1 indole | Step 3 sulfonyl chloride | Step 4 boronic acid | Resulting compound |
|---|---|---|---|---|
| P-0112 | 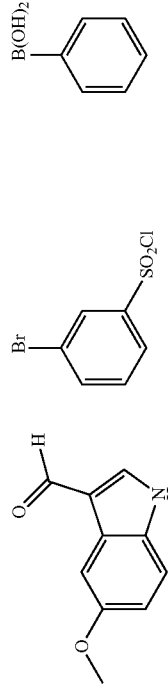 | 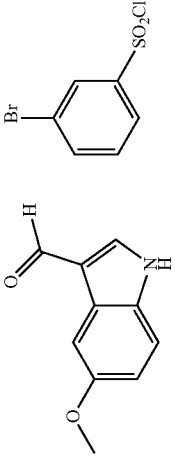 | 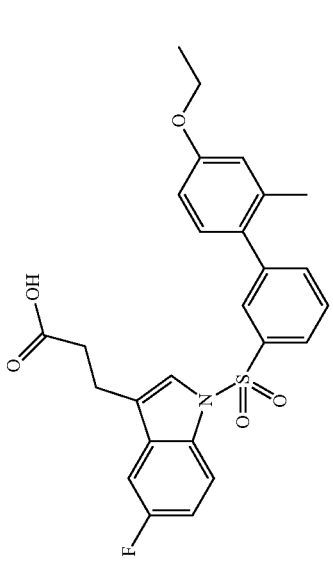 | 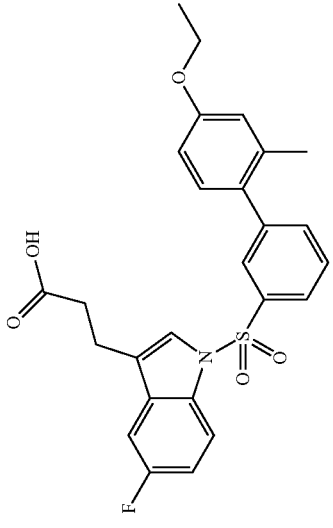 |
| P-0113 | 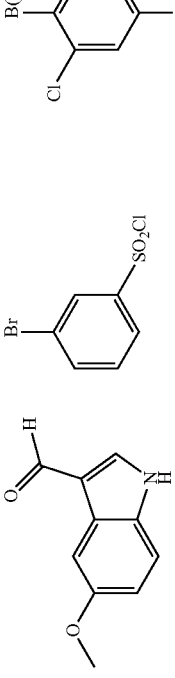 | 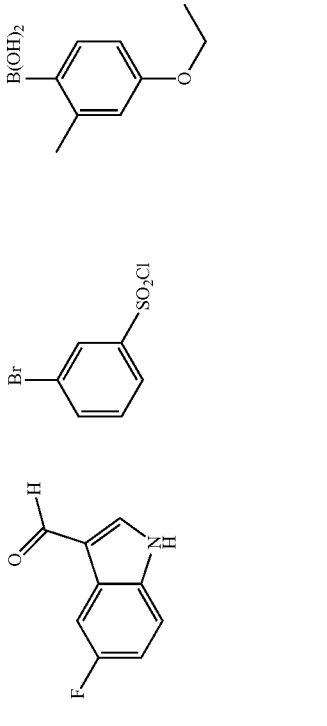 | 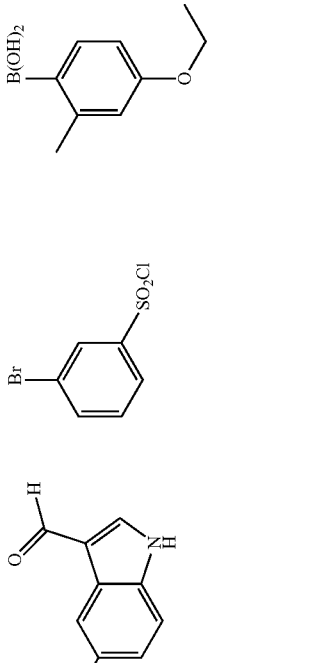 | 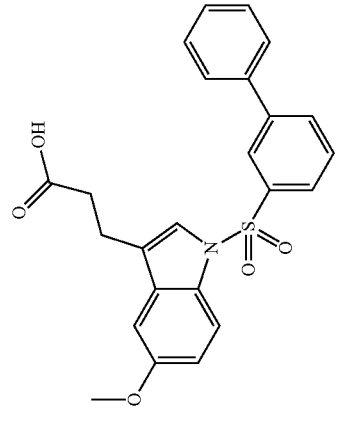 |
| P-0114 | 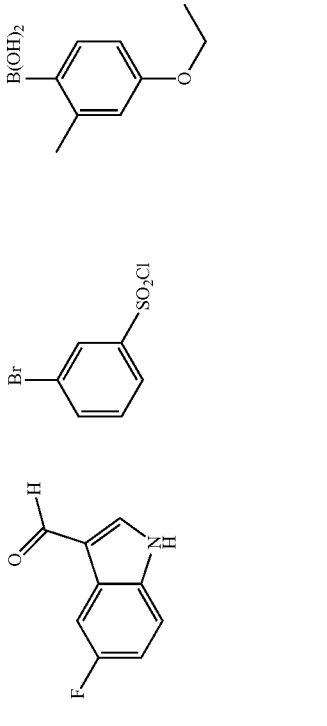 | 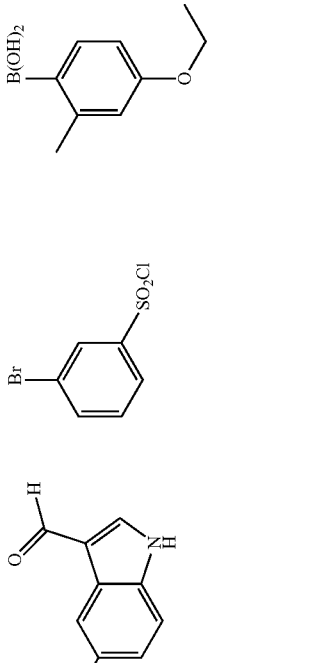 | 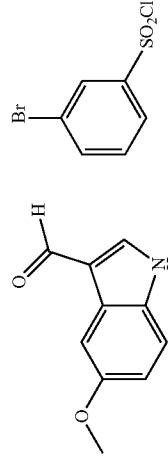 | 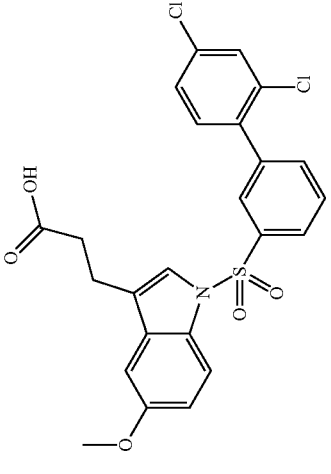 |

TABLE 1-continued
| Compound number | Step 1 indole | Step 3 sulfonyl chloride | Step 4 boronic acid | Resulting compound |
|---|---|---|---|---|
| P-0115 | 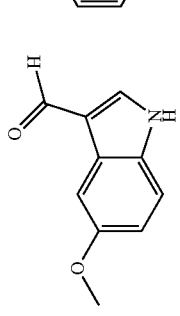 |  | 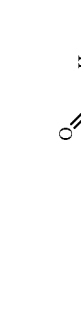 | 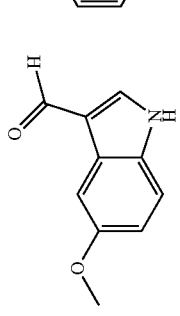 |
| P-0116 |  | 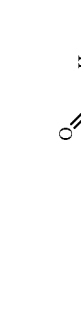 | 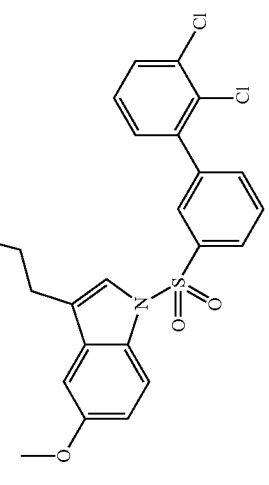 | 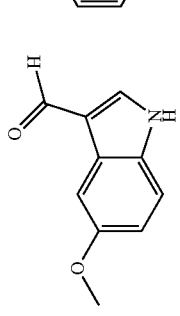 |
| P-0117 |  | 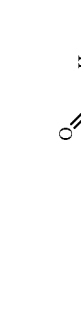 | 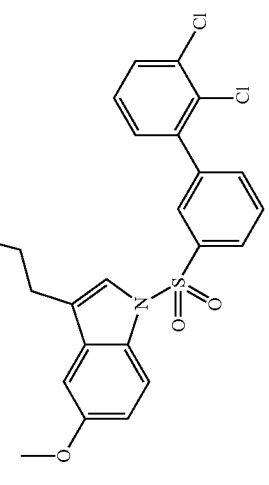 | |

TABLE 1-continued
| Compound number | Step 1 indole | Step 3 sulfonyl chloride | Step 4 boronic acid | Resulting compound |
|---|---|---|---|---|
| P-0118 | 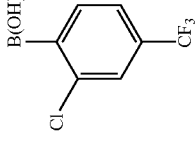 | 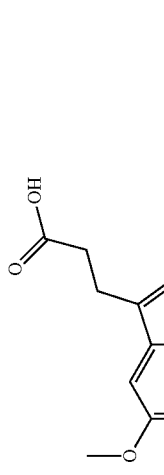 | 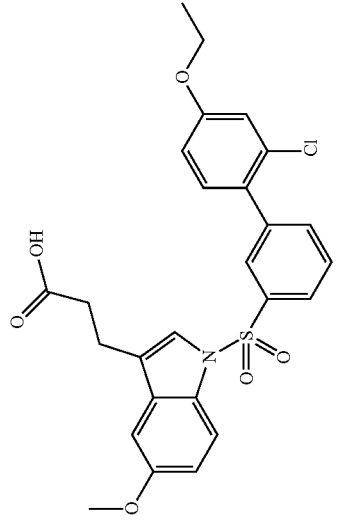 | 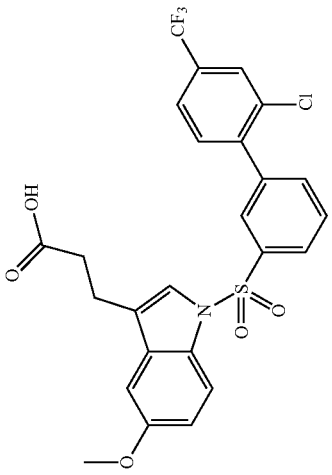 |
| P-0119 | 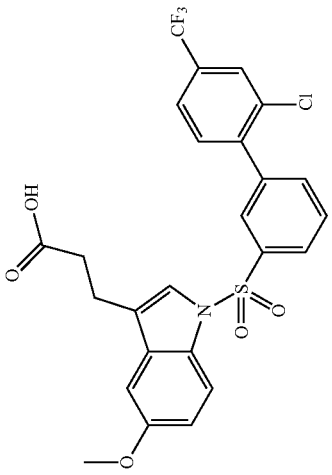 | 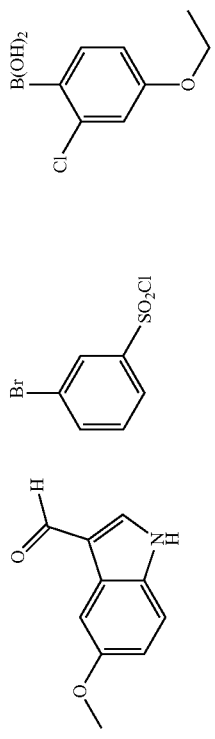 | 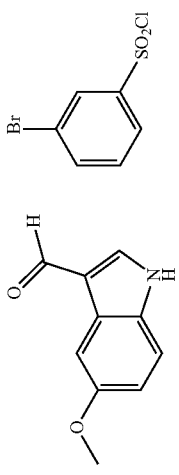 | 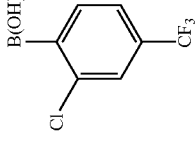 |
| P-0120 | 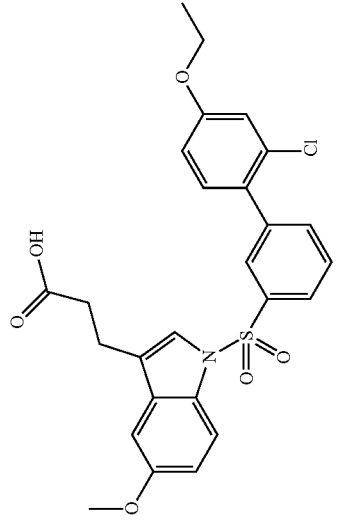 | 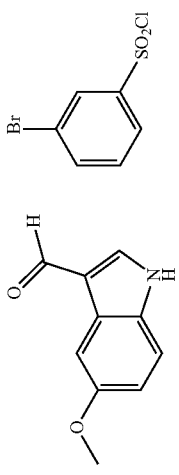 | 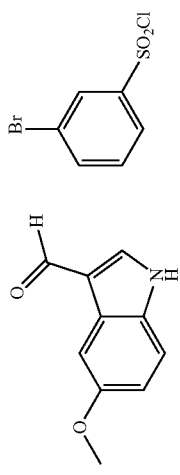 | 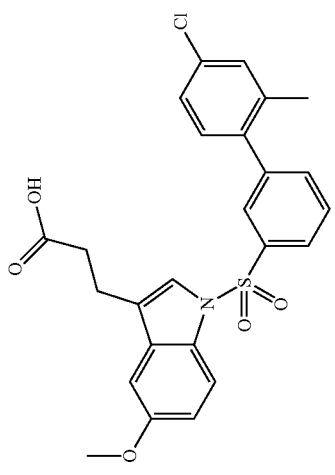 |

TABLE 1-continued

| Compound number | Step 1 indole | Step 3 sulfonyl chloride | Step 4 boronic acid | Resulting compound |
|---|---|---|---|---|
| P-0121 | 5-methoxy-1H-indole-3-carbaldehyde | 3-bromobenzenesulfonyl chloride | 2-chloro-3-fluorophenylboronic acid | 3-(1-((2'-chloro-3'-fluoro-[1,1'-biphenyl]-3-yl)sulfonyl)-5-methoxy-1H-indol-3-yl)propanoic acid |
| P-0122 | 5-methoxy-1H-indole-3-carbaldehyde | 3-bromobenzenesulfonyl chloride | 2-chloro-4-fluorophenylboronic acid | 3-(1-((2'-chloro-4'-fluoro-[1,1'-biphenyl]-3-yl)sulfonyl)-5-methoxy-1H-indol-3-yl)propanoic acid |
| P-0123 | 5-methoxy-1H-indole-3-carbaldehyde | 3-bromobenzenesulfonyl chloride | 4-ethoxy-2-methylphenylboronic acid | 3-(1-((4'-ethoxy-2'-methyl-[1,1'-biphenyl]-3-yl)sulfonyl)-5-methoxy-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0124 | 5-chloro-1H-indole-3-carbaldehyde | 3-bromobenzenesulfonyl chloride | phenylboronic acid | 3-(5-chloro-1-(biphenyl-3-ylsulfonyl)-1H-indol-3-yl)propanoic acid |
| P-0125 | 5-chloro-1H-indole-3-carbaldehyde | 3-bromobenzenesulfonyl chloride | 2,4-dichlorophenylboronic acid | 3-(5-chloro-1-(2',4'-dichlorobiphenyl-3-ylsulfonyl)-1H-indol-3-yl)propanoic acid |
| P-0126 | 5-chloro-1H-indole-3-carbaldehyde | 3-bromobenzenesulfonyl chloride | 4-fluoro-2-methylphenylboronic acid | 3-(5-chloro-1-(4'-fluoro-2'-methylbiphenyl-3-ylsulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0127 | 5-chloro-1H-indole-3-carbaldehyde | 3-bromobenzenesulfonyl chloride | 2,3-dichlorophenylboronic acid | 3-(5-chloro-1-((2',3'-dichloro-[1,1'-biphenyl]-3-yl)sulfonyl)-1H-indol-3-yl)propanoic acid |
| P-0128 | 5-chloro-1H-indole-3-carbaldehyde | 3-bromobenzenesulfonyl chloride | 2,3-difluorophenylboronic acid | 3-(5-chloro-1-((2',3'-difluoro-[1,1'-biphenyl]-3-yl)sulfonyl)-1H-indol-3-yl)propanoic acid |
| P-0129 | 5-chloro-1H-indole-3-carbaldehyde | 3-bromobenzenesulfonyl chloride | 2-chloro-4-(trifluoromethyl)phenylboronic acid | 3-(5-chloro-1-((2'-chloro-4'-(trifluoromethyl)-[1,1'-biphenyl]-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0130 | 5-chloro-1H-indole-3-carbaldehyde | 3-bromobenzenesulfonyl chloride | 4-chloro-2-methylphenylboronic acid | 3-(5-chloro-1-((4'-chloro-2'-methylbiphenyl-3-yl)sulfonyl)-1H-indol-3-yl)propanoic acid |
| P-0131 | 5-chloro-1H-indole-3-carbaldehyde | 3-bromobenzenesulfonyl chloride | 2-chloro-4-ethoxyphenylboronic acid | 3-(5-chloro-1-((2'-chloro-4'-ethoxybiphenyl-3-yl)sulfonyl)-1H-indol-3-yl)propanoic acid |
| P-0132 | 5-chloro-1H-indole-3-carbaldehyde | 3-bromobenzenesulfonyl chloride | 2-chloro-3-fluorophenylboronic acid | 3-(5-chloro-1-((2'-chloro-3'-fluorobiphenyl-3-yl)sulfonyl)-1H-indol-3-yl)propanoic acid |

TABLE 1-continued
| Compound number | Step 1 indole | Step 3 sulfonyl chloride | Step 4 boronic acid | Resulting compound |
|---|---|---|---|---|
| P-0133 | 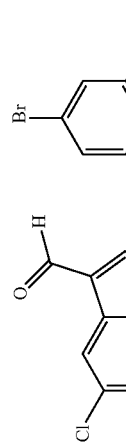 | 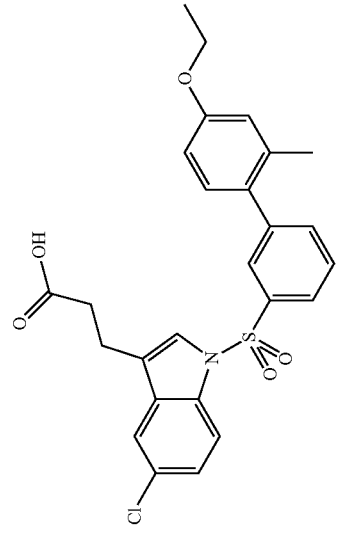 | 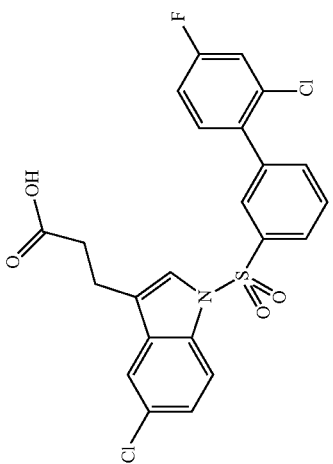 | 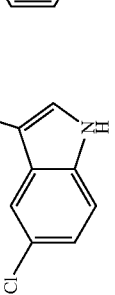 |
| P-0134 | 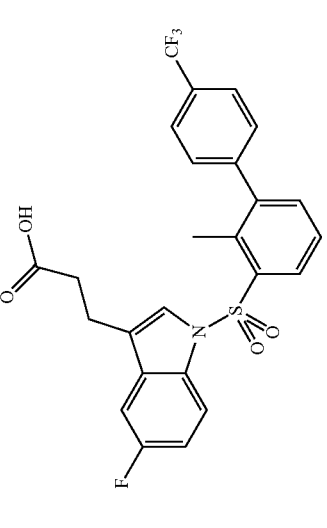 | 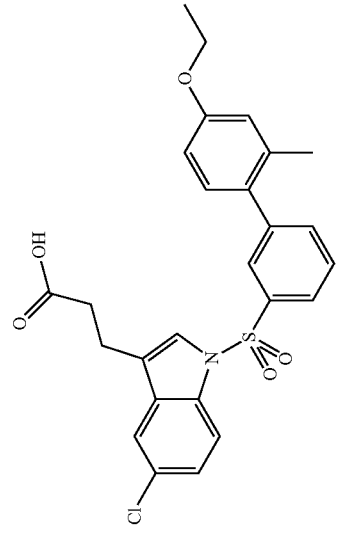 | 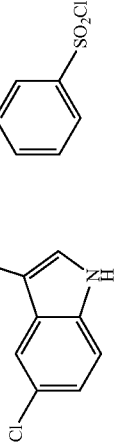 | 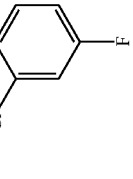 |
| P-0137 | 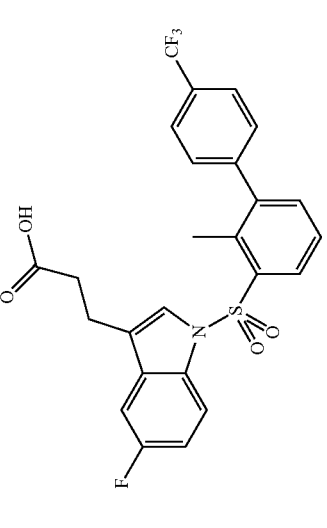 | 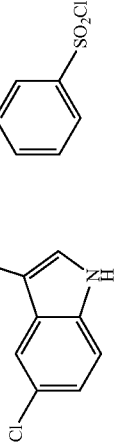 | 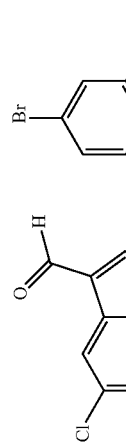 | 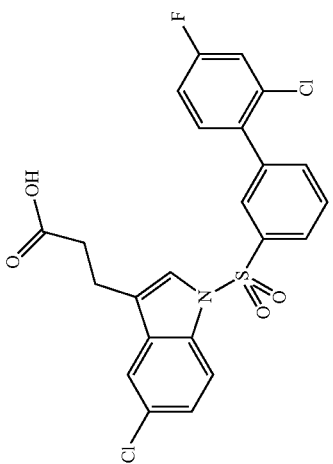 |

TABLE 1-continued

| Compound number | Step 1 indole | Step 3 sulfonyl chloride | Step 4 boronic acid | Resulting compound |
|---|---|---|---|---|
| P-0138 | 5-fluoro-1H-indole-3-carbaldehyde | 3-bromo-2-methylbenzenesulfonyl chloride | 4-chlorophenylboronic acid | |
| P-0139 | 7-methyl-1H-indole-3-carbaldehyde | 3-bromobenzenesulfonyl chloride | 4-trifluoromethoxyphenylboronic acid | |
| P-0140 | 7-methyl-1H-indole-3-carbaldehyde | 3-bromobenzenesulfonyl chloride | 4-trifluoromethylphenylboronic acid | |

TABLE 1-continued

| Compound number | Step 1 indole | Step 3 sulfonyl chloride | Step 4 boronic acid | Resulting compound |
|---|---|---|---|---|
| P-0141 | 7-chloro-1H-indole-3-carbaldehyde | 3-bromobenzenesulfonyl chloride | 2-fluoro-4-(trifluoromethyl)phenylboronic acid | 3-(7-chloro-1-((2'-fluoro-4'-(trifluoromethyl)biphenyl-3-yl)sulfonyl)-1H-indol-3-yl)propanoic acid |
| P-0142 | 1H-indole-3-carbaldehyde | 3-bromo-2-methylbenzenesulfonyl chloride | 4-(trifluoromethyl)phenylboronic acid | 3-(1-((2-methyl-4'-(trifluoromethyl)biphenyl-3-yl)sulfonyl)-1H-indol-3-yl)propanoic acid |
| P-0143 | 1H-indole-3-carbaldehyde | 3-bromo-2-methylbenzenesulfonyl chloride | 4-(trifluoromethoxy)phenylboronic acid | 3-(1-((2-methyl-4'-(trifluoromethoxy)biphenyl-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0144 | 7-chloro-1H-indole-3-carbaldehyde | 3-bromobenzenesulfonyl chloride | 4-(trifluoromethyl)phenylboronic acid | 3-(7-chloro-1-((4'-(trifluoromethyl)biphenyl-3-yl)sulfonyl)-1H-indol-3-yl)propanoic acid |
| P-0145 | 7-chloro-1H-indole-3-carbaldehyde | 3-bromobenzenesulfonyl chloride | 4-(trifluoromethoxy)phenylboronic acid | 3-(7-chloro-1-((4'-(trifluoromethoxy)biphenyl-3-yl)sulfonyl)-1H-indol-3-yl)propanoic acid |

TABLE 1-continued

| Compound number | Step 1 indole | Step 3 sulfonyl chloride | Step 4 boronic acid | Resulting compound |
|---|---|---|---|---|
| P-0146 | 7-chloro-1H-indole-3-carbaldehyde | 3-bromo-2-methylbenzenesulfonyl chloride | 4-(trifluoromethyl)phenylboronic acid | 3-(5-chloro-1-((2-methyl-4'-(trifluoromethyl)biphenyl-3-yl)sulfonyl)-1H-indol-3-yl)propanoic acid |
| P-0147 | 7-chloro-1H-indole-3-carbaldehyde | 3-bromo-2-methylbenzenesulfonyl chloride | 4-(trifluoromethoxy)phenylboronic acid | 3-(5-chloro-1-((2-methyl-4'-(trifluoromethoxy)biphenyl-3-yl)sulfonyl)-1H-indol-3-yl)propanoic acid |

*the methyl ester was isolated after Step 4

Example 3

Synthesis of 3-{5-Chloro-1-[5-(4-trifluoromethyl-phenyl)-pyridine-3-sulfonyl]-1H-indol-3-yl}-propionic acid P-0149

3-{5-Chloro-1-[5-(4-trifluoromethyl-phenyl)-pyridine-3-sulfonyl]-1H-indol-3-yl}-propionic acid P-0149 was synthesized in five steps from 5-chloro-1H-indole-3-carbaldehyde 7 as shown in Scheme 2.

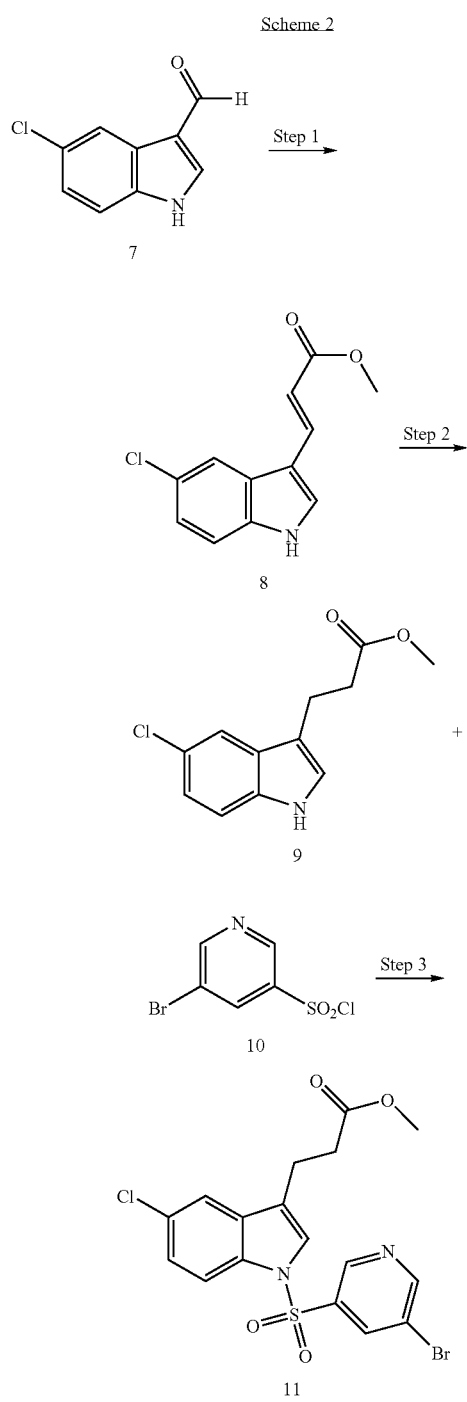

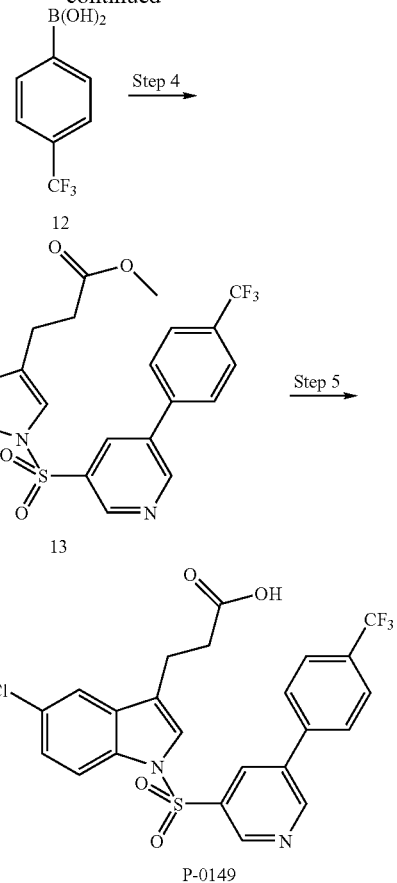

Step 1—Preparation of (E)-3-(5-chloro-1H-indol-3-yl)-acrylic acid methyl ester (8):

In a flask, methyl diethylphosphonoacetate (14 g, 0.067 mol) in 60 mL of tetrahydrofuran was cooled in an ice bath and sodium hydride (702 mg, 0.0292 mol) was added in portions over 20 minutes. After final addition of the sodium hydride, the mixture was stirred on the ice bath for 20 minutes, then removed from the ice bath with stirring for 20 minutes. In an oven dried three-neck round bottom flask under argon, 5-chloro-1H-indole-3-carbaldehyde (7, 5.0 g, 0.028 mol) was dissolved in 160 mL of tetrahydrofuran, and the phosphonate solution was added to this drop wise over 40 minutes. The reaction was heated at 60° C. overnight. TLC (20% ethyl acetate/hexane) showed a major product above the starting material. Methanol (4 mL) was added to the reaction and the reaction was stirred for 4 minutes. The solvent was removed under vacuum to provide an oil, which was dissolved in 270 mL of ethyl acetate, washed with 2×100 mL of water and 200 mL of brine. The organic layer was dried over $MgSO_4$, filtered and concentrated at reduced pressure, then filtered over a plug of silica using 20% ethyl acetate in hexanes to isolate the desired compound. $^1H$ NMR consistent with structure.

Step 2—Preparation of 3-(5-chloro-1H-indol-3-yl)-propionic acid methyl ester (9):

Into a flask, (E)-3-(5-chloro-1H-indol-3-yl)-acrylic acid methyl ester (8, 3.4 g, 0.014 mol) and 10% palladium on carbon were combined and 140 mL of ethyl acetate was added. Vacuum was applied and the flask was back filled with hydrogen, repeated application of vacuum and hydrogen back fill for total of three times. The reaction was capped with a hydrogen filled balloon and the reaction stirred overnight at room temperature. TLC (20% ethyl acetatethexane) indicated absence of starting material and a major new spot. The reaction was filtered through celite and the filter rinsed generously with a total of 250 mL of ethyl acetate. The yellow filtrate solution was roto-evaporated to near dryness, silica was added, and the solvent fully removed. Column chromatography was performed, eluting with 2 to 30% ethyl acetate/hexane, then flushing with 40% ethyl acetate/hexane to provide the desired compound. $^1$H NMR consistent with structure.

Step 3—Preparation of 3-[1-(5-bromo pyridine-3-sulfonyl)-5-chloro-1H-indol-3-yl]-propionic acid methyl ester (11):

Into a flask, 3-(5-chloro-1H-indol-3-yl)-propionic acid methyl ester (11, 150 mg, 0.00063 mol), and tetrabutyl ammonium hydrogen sulfate were dissolved in 20 mL of dichloromethane and 20 mL of 50% KOH solution was added. The solution was mixed vigorously and 5-bromo-pyridyl-3-sulfonyl chloride (10, 240 mg, 0.00095 mol) was slowly added to the reaction. After 5-6 minutes of vigorous stirring, precipitates began to form. An additional 3-4 mL of 50% KOH was added and the reaction was stirred overnight. TLC (30% ethyl acetate/hexane) showed that the starting material had disappeared. The reaction mixture was extracted with 3×50 mL of dichloromethane and the organic layers were combined and washed with water, brine, and dried over $MgSO_4$. The organic layer was filtered and roto evaporated to half its volume. Silica was added and the solvent completely removed. Chromatography was run using a gradient solvent condition of 0 to 20% ethyl acetate/hexane over 15 minutes, then 20 to 45% over 15 minutes. The desired compound was isolated. $^1$H NMR consistent with structure.

Step 4—Preparation of 3-{5-chloro-1-[5-(4-trifluoromethyl-phenyl)-pyridine-3-sulfonyl]-1H-indol-3-yl}-propionic acid methyl ester (13):

In a micro wave test tube, 3-[1-(5-bromo pyridine-3-sulfonyl)-5-chloro-1H-indol-3-yl]propionic acid methyl ester (11, 40 mg, 0.00009 mol), 4-(trifluoromethyl)-phenylboronic acid (12, 52 mg, 0.00027 mol), and tetrakis(triphenylphosphine) palladium(0) (4 mg, 0.000003 mol) were combined in 4 mL of 1,4-dioxane. The vessel was purged with argon for 2-3 minutes, then 0.1 mL of 1N $K_2CO_3$ was added. The vessel was microwaved at 108° C. for 40 minutes. TLC (20% ethyl acetate,/hexane) indicated a new spot and total disappearance of starting material. The crude mixture was transferred to a separatory funnel and extracted with 3×40 mL of ethyl acetate and washed with water, brine, and dried over $MgSO_4$. The solution was filtered and the filtrate roto evaporated to near dryness. Silica and 5 mL of ethyl acetate were added and the solvent removed. Chromatography was run using a gradient solvent condition of 0 to 20% ethyl acetate/hexane over 18 minutes, then 20 to 30% over 10 minutes to isolate the desired compound. $^1$H NMR consistent with structure.

Step 5—Synthesis of 3-{5-chloro-1-[5-(4-trifluoromethyl-phenyl)-pyridine-3-sulfonyl]-1H-indol-3-yl}-propionic acid (P-0149):

The 3-{5-chloro-1-[5-(4-trifluoromethyl-phenyl)-pyridine-3-sulfonyl]-1H-indol-3-yl}-propionic acid methyl ester 13 (20 mg, 0.00038 mol) was dissolved in 4 mL mixture of tetrahydrofuran:1N LiOH (4:1) and stirred vigorously overnight. TLC (20% ethyl acetate hexane) indicated absence of starting material and a new spot. The reaction was acidified by adding 1N HCl (pH 0-1 by pH paper) and extracted with 12 mL of ethyl acetate, which was dried over $MgSO_4$. A silica plate was carried out using 2% methanol/chloroform to isolate the desired compound. $^1$H NMR consistent with structure. MS(ESI) [M−H$^+$]$^−$=507.02 (calculated 508.90).

The following compounds were prepared following the protocol of Scheme 2, optionally replacing 5-chloro-1H-indole-3-carbaldehyde 7 with an appropriate 1H-indole-3-carbaldehyde compound in Step 1 and/or optionally replacing 4-trifluoromethyl-phenyl boronic acid 12 with an appropriate boronic acid in Step 4:

3-{5-Chloro-1-[5-(4-trifluoromethoxy-phenyl)-pyridine-3-sulfonyl]-1H-indol-3-yl}-propionic acid (P-0148), 3-{5-Fluoro-1-[5-(4-trifluoromethoxy-phenyl)-pyridine-3-sulfonyl]-1H-indol-3-yl}propionic acid methyl ester (P-0150), 3-{5-Fluoro-1-[5-(4-trifluoromethyl-phenyl)-pyridine-3-sulfonyl]-1H-indol-3-yl}-propionic acid methyl ester (P-0151), 3-{1-[5-(4-Chloro-phenyl)-pyridine-3-sulfonyl]-5-fluoro-1H-indol-3-yl}-propionic acid methyl ester (P-0152), 3-{5-Fluoro-1-[5-(2-fluoro-4-trifluoromethyl-phenyl)-pyridine-3-sulfonyl]-1H-indol-3yl}-propionic acid methyl ester (P-0153), 3-{5-Fluoro-1-[5-(4-trifluoromethoxy-phenyl)-pyridine-3-sulfonyl]-1H-indol-3-yl}-propionic acid (P-0154), 3-{5-Fluoro-1-[5-(4-trifluoromethyl-phenyl)-pyridine-3-sulfonyl]-1H-indol-3-yl}-propionic acid (P-0155), 3-{5-Chloro-1-[5-(4-ethoxy-2-methyl-phenyl)-pyridine-3-sulfonyl]-1H-indol-3-yl}-propionic acid (P-0156), 3-{5-Chloro-1-[5-(2-chloro-4-ethoxy-phenyl)-pyridine-3-sulfonyl]-1H-indol-3-yl}-propionic acid (P-0157), 3-{5-Chloro-1-[5-(2-fluoro-4-trifluoromethyl-phenyl)-pyridin-3-sulfonyl]-1H-indol-3-yl}-propionic acid (P-0158), 3-{5-Chloro-1-[5-(2-chloro-4-trifluoromethyl-phenyl)-pyridine-3-sulfonyl]-1H-indol-3-yl}-propionic acid (P-0159), 3-{5-Chloro-1-[5-(2-methyl-4-trifluoromethyl-phenyl)-pyridine-3-sulfonyl]-1H-indol-3-yl}-propionic acid (P-0160), 3-{-[5-(4-Ethoxy-2-methyl-phenyl)-pyridine-3-sulfonyl]-5-fluoro-H-indol-3-yl}-propionic acid (P-0161), 3-{1-[5-(2-Chloro-4-trifluoromethyl-phenyl)-pyridine-3-sulfonyl]-5-fluoro-1H -indol-3-yl}-propionic acid (P-0162), 3-{5-Fluoro-1-[5-(2-methyl -4-trifluoromethyl-phenyl)-pyridine-3-sulfonyl]-1H-indol-3yl}-propionic acid (P-0163), 3-{5-Fluoro-1-[5-(2-fluoro-4-trifluoromethyl-phenyl)-pyridine-3-sulfonyl]-1H-indol-3-yl}-propionic acid (P-0164), 3-{1-[5-(3-Chloro-4-fluoro-phenyl)-pyridine-3-sulfonyl]-5-methoxy-1H-indol-3-yl}-propionic acid (P-0165), and all salts, prodrugs, tautomers, and isomers thereof.

The following Table 2 indicates the compound number in Column 1, the structure of the indole used in Step 1 in Column 2 and the structure of the boronic acid used in Step 4 in Column 3. The resulting compound structure is provided in Column 4 and the experimental mass in Column 5.

TABLE 2

| Comp. number | Step 1 indole | Step 4 boronic acid | Resulting compound | Measured MS(ESI) [M + H+]+ |
|---|---|---|---|---|
| P-0148 | | | | 523.08 [M − H+]− |
| P-0150* | | | | 523.2 |
| P-0151* | | | | 507.3 |
| P-0152* | | | | 472.5  472.3 |
| P-0153* | | | | 525.2 |

TABLE 2-continued

| Comp. number | Step 1 indole | Step 4 boronic acid | Resulting compound | Measured MS(ESI) [M + H⁺]⁺ |
|---|---|---|---|---|
| P-0154 | | | | 507.2 [M − H⁺]⁻ |
| P-0155 | | | | 491.0 [M − H⁺]⁻ |
| P-0156 | | | | 498.95 |
| P-0157 | | | | 518.95 |
| P-0158 | | | | 526.90 |

TABLE 2-continued
| Comp. number | Step 1 indole | Step 4 boronic acid | Resulting compound | Measured MS(ESI) [M + H+]+ |
|---|---|---|---|---|
| P-0159 | 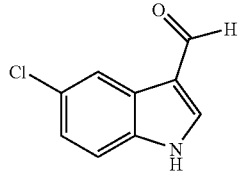 | 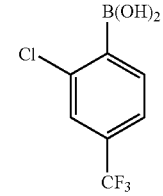 | 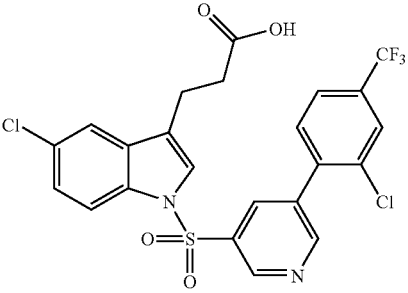 | 542.80 |
| P-0160 | 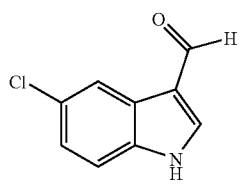 | 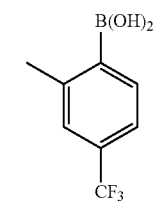 | 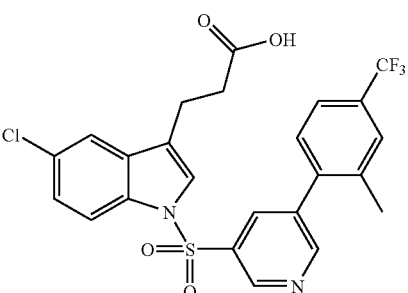 | 522.90 |
| P-0161 | 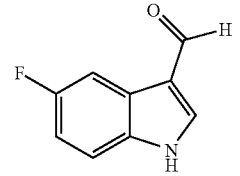 | 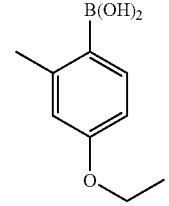 | 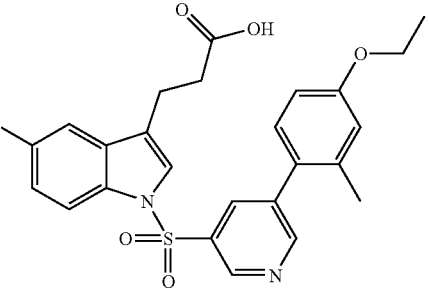 | 482.1 [M − H+]− |
| P-0162 | 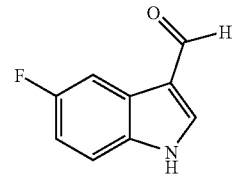 | 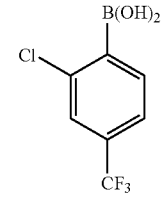 | 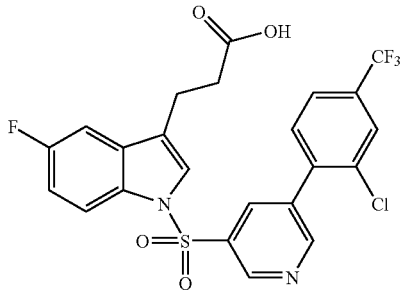 | 524.2 526.2 [M − H+]− |
| P-0163 | 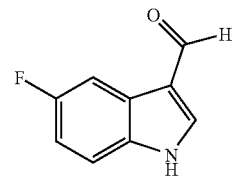 | 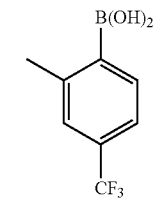 | 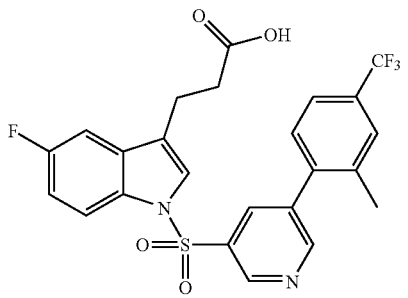 | 505.2 [M − H+]− |

TABLE 2-continued

| Comp. number | Step 1 indole | Step 4 boronic acid | Resulting compound | Measured MS(ESI) [M + H⁺]⁺ |
|---|---|---|---|---|
| P-0164 | (5-fluoro-indole-3-carbaldehyde) | (2-fluoro-4-trifluoromethylphenyl boronic acid) | (resulting compound structure) | 509.2 [M − H⁺]⁻ |
| P-0165 | (5-methoxy-indole-3-carbaldehyde) | (3-chloro-4-fluorophenyl boronic acid) | (resulting compound structure) | 489.23 |

*The methyl ester was isolated after Step 4.

Example 4

PPAR Activity Assays

Assays for the activity of PPARα, PPARγ and PPARδ are known in the art, for example, biochemical and cell based assays as described in US Patent Application Publication number US 2007/0072904, the disclosure of which is hereby incorporated by reference in its entirety. Compounds having $EC_{50}$ of less than or equal to 1 µM in at least one of these assays, or a similar assay, for at least one of PPARα, PPARγ and PPARδ are shown in Table 3.

TABLE 3

Compounds of the invention having $EC_{50}$ of less than or equal to 1 µM in at least one of PPARα, PPARγ, or PPARδ activity assays.

P-0002, P-0003, P-0004, P-0005, P-0006, P-0007, P-0008, P-0009, P-0010, P-0011, P-0012,
P-0013, P-0014, P-0015, P-0016, P-0017, P-0018, P-0019, P-0020, P-0021, P-0022, P-0023,
P-0024, P-0025, P-0026, P-0027, P-0029, P-0030, P-0031, P-0032, P-0034, P-0035, P-0036,
P-0037, P-0039, P-0040, P-0041, P-0042, P-0044, P-0045, P-0046, P-0047, P-0048, P-0049,
P-0050, P-0051, P-0052, P-0053, P-0054, P-0055, P-0056, P-0057, P-0058, P-0059, P-0060,
P-0061, P-0062, P-0063, P-0064, P-0065, P-0066, P-0067, P-0068, P-0069, P-0070, P-0071,
P-0072, P-0073, P-0074, P-0075, P-0076, P-0077, P-0078, P-0079, P-0080, P-0081, P-0082,
P-0083, P-0084, P-0085, P-0086, P-0087, P-0088, P-0089, P-0098, P-0101, P-0102, P-0103,
P-0104, P-0105, P-0106, P-0107, P-0108, P-0109, P-0110, P-0111, P-0112, P-0113, P-0114,
P-0115, P-0116, P-0117, P-0118, P-0119, P-0120, P-0121, P-0122, P-0123, P-0124, P-0125,
P-0126, P-0127, P-0128, P-0129, P-0130, P-0131, P-0132, P-0133, P-0134, P-0146, P-0147,
P-0148, P-0149, P-0153, P-0154, P-0155, P-0156, P-0157, P-0158, P-0159, P-0160, P-0161,
P-0162, P-0163, P-0164, P-0165.

Additional examples of certain methods contemplated by the present invention may be found in the following applications: U.S. Prov. App. No. 60/715,327, filed Sep. 7, 2005, and U.S. App. Ser. No. 11/517,573, filed Sep. 6, 2006, both of which are incorporated herein by reference in their entireties including all specifications, figures, and tables, and for all purposes.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, and defined by the scope of the claims.

It will be readily apparent to one skilled in the art that varying substitutions and modifications may be made to the invention disclosed herein without departing from the scope and spirit of the invention. For example, variations can be made to provide additional compounds of Formula I and/or various methods of administration can be used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:
1. A compound having the chemical structure

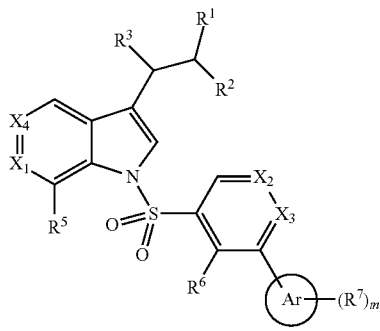

pharmaceutically acceptable salts, tautomers or isomers thereof,
wherein:
$X_2$ and $X_3$ are CH;
one of $X_1$ and $X_4$ is $CR^4$ and the other of $X_1$ and $X_4$ is CH;
Ar is aryl;
$R^1$ is selected from the group consisting of $-C(O)OR^8$, $-C(O)NR^9R^{10}$, and a carboxylic acid isostere;
$R^2$ and $R^3$ are each hydrogen, or $R^2$ and $R^3$ combine to form optionally substituted 3-7 membered monocyclic cycloalkyl;
$R^4$ is hydrogen, fluoro, chloro, methoxy or fluoro substituted methoxy;
$R^5$ is hydrogen, fluoro, chloro, $C_{1-3}$ alkyl, or fluoro substituted $C_{1-3}$ $R^6$ is hydrogen, fluoro, chloro, $C_{1-3}$ alkyl, or fluoro substituted $C_{1-3}$ alkyl;
$R^7$ at each occurence is independently selected from the group consisting of halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, $-NO_2$, $-CN$, $-OR^{11}$, $-NR^{11}R^{12}$, $-C(Z)NR^{11}R^{12}$, $-C(Z)R^{13}$, $-S(O)_2NR^{11}R^{12}$, $-S(O)_nR^{13}$, $-OC(Z)R^{13}$, $-C(Z)OR^{11}$, $-C(NH)NR^{14}R^{15}$, $-NR^{11}C(Z)R^{13}$, $-NR^{11}S(O)_2R^{13}$, $-NR^{11}C(Z)NR^{11}R^{12}$, and $-NR^{11}S(O)_2NR^{11}R^{12}$;
$R^8$ is selected from the group consisting of hydrogen, lower alkyl, phenyl, 5-7 membered monocyclic heteroaryl, 3-7 membered monocyclic cycloalkyl, and 5-7 membered monocylic heterocycloalkyl, wherein phenyl, monocyclic heteroaryl, monocyclic cycloalkyl and monocyclic heterocycloalkyl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, $-OH$, $-NH_2$, lower alkoxy, fluoro substituted lower alkoxy, lower alkylthio and fluoro substituted lower alkylthio, provided, however, that when $R^8$ is lower alkyl, any substitution on the lower alkyl carbon bound to the O of $OR^8$ is fluoro;
$R^9$ and $R^{10}$ are independently selected from the group consisting of hydrogen, lower alkyl, phenyl, 5-7 membered monocyclic heteroaryl, 3-7 membered monocyclic cycloalkyl, and 5-7 membered monocyclic heterocycloalkyl, wherein phenyl, monocyclic heteroaryl, monocyclic cycloalkyl and monocyclic heterocycloalkyl are optionally substituted with one or more substituents selected from the group consisting of halogen, $-OH$, $-NH_2$ lower alkyl, fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, $-OH$, $-NH_2$, lower alkoxy, fluoro substituted lower alkoxy, lower alkylthio and fluoro substituted lower alkylthio, provided, however, that when $R^9$ and/or $R^{10}$ is lower alkyl, any substitution on the lower alkyl carbon bound to the N of $NR^9R^{10}$ is fluoro; or
$R^9$ and $R^{10}$ together with the nitrogen to which they are attached form a 5-7 membered monocyclic heterocycloalkyl or a 5 or 7 membered nitrogen containing monocyclic heteroaryl, wherein the monocyclic heterocycloalkyl or monocyclic nitrogen containing heteroaryl is optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, and fluoro substituted lower alkylthio;

$R^{11}$, $R^{12}$, $R^{14}$, and $R^{15}$ at each occurrence are independently selected from the group consisting of hydrogen, optionally substituted lower alkyl, optionally substituted $C_{3-6}$ alkenyl, provided, however, that when $R^{11}$, $R^{12}$, $R^{14}$, or $R^{15}$ is optionally substituted $C_{3-6}$ alkenyl, no alkene carbon thereof is bound to the O of any $OR^{11}$ or N of any $NR^{11}$, $NR^{12}$, $NR^{14}$ or $NR^{15}$; optionally substituted $C_{3-6}$ alkynyl, provided, however, that when $R^{11}$, $R^{12}$, $R^{14}$, or $R^{15}$ is optionally substituted $C_{3-6}$ alkynyl, no alkyne carbon thereof is the O of any $OR^{11}$ or N of any $NR^{11}$, $NR^{12}$, $NR^{14}$ or $NR^{15}$; optionally substituted cycloalkyl, optionally substituted heterocycloalkyl, optionally substituted aryl, and optionally substituted heteroaryl, or $R^{14}$ and $R^{15}$ combine with the nitrogen to which they are attached to form a 5-7 membered optionally substituted heterocycloalkyl or a 5 or 7 membered optionally substituted nitrogen containing heteroaryl;

$R^{13}$ at each occurrence is independently selected from the group consisting of optionally substituted lower alkyl, optionally substituted $C_{3-6}$ alkenyl, provided, however, that when $R^{13}$ is optionally substituted $C_{3-6}$ alkenyl, no alkene carbon thereof is bound to the S of any $S(O)_n R^{13}$ or the C of any $C(Z)R^{13}$; optionally substituted $C_{3-6}$ alkynyl, provided, however, that when $R^{13}$ is optionally substituted $C_{3-6}$ alkynyl, no alkyne carbon thereof is bound to the S of any $S(O)_n R^{13}$ or the C of any $C(Z)R^{13}$; optionally substituted cycloalkyl, optionally substituted heterocycloalkyl, optionally substituted aryl, and optionally substituted heteroaryl;

Z is O or S;
n is 0, 1 or 2; and
m is 0, 1, 2, 3, 4, or 5, provided, however, that the compound is not

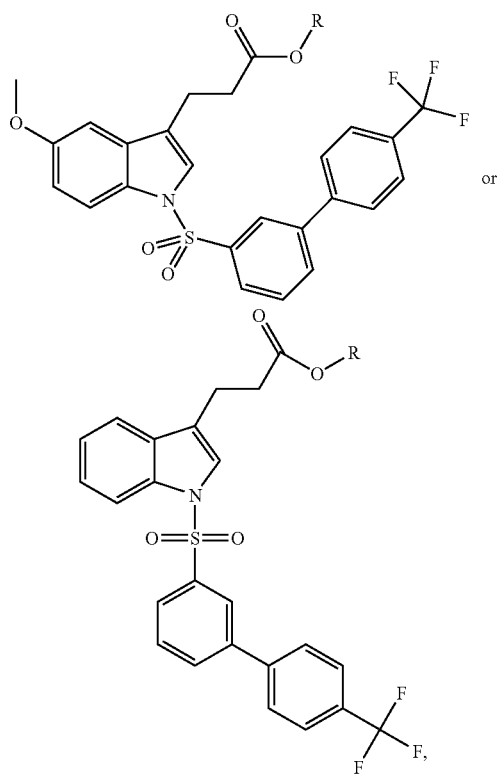

wherein R s H, methyl or ethyl.

2. The compound of claim 1, wherein Ar is phenyl.
3. The compound of claim 1, wherein $X_1$ is CH, $X_4$ is $CR^4$ and $R^5$ is hydrogen.
4. The compound of claim 3, wherein Ar is phenyl.
5. The compound of claim 1, wherein $X_1$ is CH and $X_4$ is CH.
6. The compound of claim 5, wherein Ar is phenyl.
7. The compound of claim 1, having the chemical structure

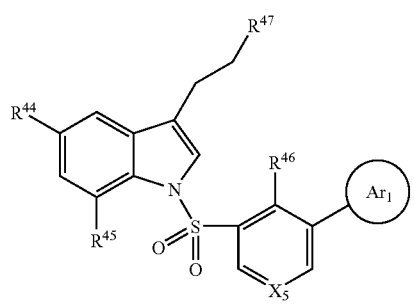

pharmaceutically acceptable salts, tautomers or isomers thereof,
wherein:
$X_5$ is CH;
$R^{44}$ is hydrogen, fluoro, chloro, or methoxy;
$R^{45}$ is hydrogen, chloro, or methyl;
$R^{46}$ is hydrogen or methyl;
$R^{47}$ is selected from the group consisting of —C(O)OR$^{48}$, —C(O)NR$^{49}$R$^{50}$, and a carboxylic acid isostere;
$R^{48}$ is selected from the group consisting of hydrogen, lower alkyl, phenyl, 5-7 membered monocyclic heteroaryl, 3-7 membered monocyclic cycloalkyl, and 5-7 membered monocylic heterocycloalkyl, wherein phenyl, monocyclic heteroaryl, monocyclic cycloalkyl and monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, —OH, —NH$_2$, lower alkoxy, fluoro substituted lower alkoxy, lower alkylthio and fluoro substituted lower alkylthio, provided, however, that when $R^{48}$ is lower alkyl, any substitution on the lower alkyl carbon bound to the O of OR$^{48}$ is fluoro;
$R^{49}$ and $R^{50}$ are independently selected from the group consisting of hydrogen, lower alkyl, phenyl, 5-7 membered monocyclic heteroaryl, 3-7 membered monocyclic cycloalkyl, and 5-7 membered monocylic heterocycloalkyl, wherein phenyl, monocyclic heteroaryl, monocyclic cycloalkyl and monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, and fluoro substituted lower alkylthio, and wherein lower alkyl is optionally substituted with one or more substituents selected from the group consisting of fluoro, —OH, —NH$_2$, lower alkoxy, fluoro substituted lower alkoxy, lower alkylthio and fluoro substituted lower alkylthio, provided, however, that when $R^{49}$ and/or $R^{50}$ is lower alkyl, any substitution on the lower alkyl carbon bound to the N of $NR^{49}R^{50}$ is fluoro; or $R^{49}$ and $R^{50}$ together with the nitrogen to which they are attached form a 5-7 membered monocyclic heterocycloalkyl or a 5 or 7 membered nitrogen containing monocyclic heteroaryl, wherein the monocyclic heterocycloalkyl or monocyclic nitrogen containing heteroaryl is optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, and fluoro substituted lower alkylthio;

$Ar_1$ is

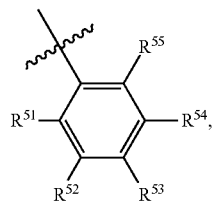

wherein

indicates the point of attachment of $Ar_1$ to the ring of Formula Ii;

$R^{51}$, $R^{52}$, $R^{53}$, $R^{54}$, $R^{55}$, $R^{58}$ and $R^{59}$ are independently selected from the group consisting of hydrogen, fluoro, chloro, $C_{1-3}$ alkyl, fluoro substituted $C_{1-3}$ alkyl, $C_{1-3}$ alkoxy, fluoro substituted $C_{1-3}$ alkoxy, and benzyloxy;

$R^{56}$, $R^{57}$, $R^{63}$ and $R^{65}$ are independently selected from the group consisting of hydrogen, fluoro, $C_{1-3}$ alkyl, fluoro substituted $C_{1-3}$ alkyl, $C_{1-3}$ alkoxy, fluoro substituted $C_{1-3}$ alkoxy, and benzyloxy;

$R^{60}$, $R^{61}$ and $R^{62}$ are independently selected from the group consisting of hydrogen, $C_{1-3}$ alkyl, fluoro substituted $C_{1-3}$ alkyl, $C_{1-3}$ alkoxy, fluoro substituted $C_{1-3}$ alkoxy, and benzyloxy; and $R^{64}$ is lower alkyl or fluoro substituted lower alkyl.

8. A composition comprising:
a pharmaceutically acceptable carrier; and
a compound according to claim 1.

* * * * *